US012527840B2

(12) United States Patent
Casanova

(10) Patent No.: US 12,527,840 B2
(45) Date of Patent: Jan. 20, 2026

(54) METHODS OF TREATING FULMINANT VIRAL HEPATITIS WITH AN IL-18 ANTAGONIST IN A PATIENT WITH AN IL-18BP VARIANT

(71) Applicant: The Rockefeller University, New York, NY (US)

(72) Inventor: Jean-Laurent Casanova, NY, NY (US)

(73) Assignee: THE ROCKEFELLER UNIVERSITY, New York, NY (US)

( * ) Notice: Subject to any disclaimer, the term of this patent is extended or adjusted under 35 U.S.C. 154(b) by 1080 days.

(21) Appl. No.: 17/615,900

(22) PCT Filed: Jun. 4, 2020

(86) PCT No.: PCT/US2020/036031
§ 371 (c)(1),
(2) Date: Dec. 2, 2021

(87) PCT Pub. No.: WO2020/247569
PCT Pub. Date: Dec. 10, 2020

(65) Prior Publication Data
US 2022/0323579 A1 Oct. 13, 2022

Related U.S. Application Data

(60) Provisional application No. 62/856,891, filed on Jun. 4, 2019.

(51) Int. Cl.
*A61P 1/16* (2006.01)
*A61K 38/17* (2006.01)
*A61P 31/12* (2006.01)
*G01N 33/576* (2006.01)
*A61K 39/00* (2006.01)
*A61K 39/395* (2006.01)
*A61K 48/00* (2006.01)
*C07K 14/54* (2006.01)
*C07K 14/715* (2006.01)

(52) U.S. Cl.
CPC ............ *A61K 38/1793* (2013.01); *A61P 1/16* (2018.01); *A61P 31/12* (2018.01); *G01N 33/576* (2013.01); *A61K 39/3955* (2013.01); *A61K 2039/507* (2013.01); *A61K 48/005* (2013.01); *C07K 14/54* (2013.01); *C07K 14/7155* (2013.01)

(58) Field of Classification Search
CPC ............ A61K 38/1793; C07K 14/7155; C07K 14/54; A61P 1/16; A61P 3/12
See application file for complete search history.

(56) References Cited

U.S. PATENT DOCUMENTS

2005/0064541 A1 3/2005 Novick et al.

OTHER PUBLICATIONS

Tokuriki et al, 2009, Current Opinion in Structural Biology. 19: 596-604.*
Bhattacharya et al, 2017. Plos One. 12(3): e0171355, pp. 1-22 as printed.*
Mazodier, et al. "Severe imbalance of IL-18/IL-18BP in patients with secondary hemophagocytic syndrome," Blood, 1 vol. 106, No. 10, pp. 3483-3489, (2015).
Cho et al., "Relevance of interleukin-10RB to chronic hepatitis B virus infection and biological activities of interferon-gamma and interleukin-22," Hepatol Int, vol. 7, No. 1, pp. 111-118, (2013).
Romporn et al., "Association of IFNAR2 and IL 1 ORB genes in chronic hepatitis B virus infection," Tissue Antigens, vol. 82, No. 1, pp. 21-25, (2013).
Belkaya et al., "Inherited IL-18BP deficiency in human fulminant viral hepatitis," Journal of Experimental Medicine, vol. 216, No. 8, pp. 1777-1790 (2019).
International Search Report corresponding to International Application No. PCT/US20/036031, dated Sep. 18, 2020.
Bachmann, M., J. Pfeilschifter, and H. Muhl, "A Prominent Role of Interleukin-18 in Acetaminophen-Induced Liver Injury Advocates Its Blockage for Therapy of Hepatic Necroinflammation," 2018, Frontiers in Immunology. 9:161, pp. 1-7.
Faggioni, R., R.C. Cattley, J. Guo, S. Flores, H. Brown, M. Qi, S. Yin, D. Hill, S. Scully, C. Chen, D. Brankow, J. Lewis, C. Baikalov, H. Yamane, T. Meng, F. Martin, S. Hu, T. Boone, and G. Senaldi. 2001. "IL-18-binding protein protects against lipopolysaccharide-induced lethality and prevents the development of Fas/Fas ligand-mediated models of liver disease in mice," Journal of immunology, 167:5913-5920.
Fantuzzi, G., N.K. Banda, C. Guthridge, A. Vondracek, S.H. Kim, B. Siegmund, T. Azam, J.A. Sennello, C.A. Dinarello, and W.P. Arend. 2003. "Generation and characterization of mice transgenic for human IL-18-binding protein isoform a," Journal of leukocyte biology 74:889-896.
Kim, J., D.Y. Chang, H.W. Lee, H. Lee, J.H. Kim, P.S. Sung, K.H. Kim, S.H. Hong, W. Kang, J. Lee, S.Y. Shin, H.T. Yu, S. You, Y.S. Choi, I. Oh, D.H. Lee, D.H. Lee, M.K. Jung, K.S. Suh, S. Hwang, W. Kim, S.H. Park, H.J. Kim, and E. C. Shin. 2018. "Innate-like Cytotoxic Function of Bystander-Activated CD8(+) T Cells Is Associated with Liver Injury in Acute Hepatitis A," Immunity 48:161-173 e165.
Shao, X., Y. Qian, C. Xu, B. Hong, W. Xu, L. Shen, C. Jin, Z. Wu, X. Tong, and H. Yao. 2013. "The protective effect of intrasplenic transplantation of Ad-IL-18BP/IL-4 gene-modified fetal hepatocytes on ConA-induced hepatitis in mice." PloS one 8:e58836.

(Continued)

*Primary Examiner* — Zachary C Howard
(74) *Attorney, Agent, or Firm* — Hoffmann & Baron LLP

(57) ABSTRACT

The invention relates to mutations and alterations in the inflammatory pathway, including IL-18BP and IL-10RB mutations, that are associated with the development of fulminant viral hepatitis following viral infection, such as following hepatitis virus infection. The invention relates to methods for treating or ameliorating viral hepatitis comprising administering IL-18BP, IL-18 antagonist, IFNγ antagonist or inhibitor, and/or IL-10RB or an IL-10 antagonist.

14 Claims, 40 Drawing Sheets

Specification includes a Sequence Listing.

(56) References Cited

OTHER PUBLICATIONS

Shinoda, M., G. Wakabayashi, M. Shimazu, H. Saito, K. Hoshino, M. Tanabe, Y. Morikawa, S. Endo, H. Ishii, and M. Kitajima. 2006. "Increased serum and hepatic tissue levels of interleukin-18 in patients with fulminant hepatic failure," Journal of gastroenterology and hepatology 21:1731-1736.
Yumoto, E., T. Higashi, K. Nouso, H. Nakatsukasa, K. Fujiwara, T. Hanafusa, Y. Yumoto, T. Tanimoto, M. Kurimoto, N. Tanaka, and T. Tsuji. 2002. "Serum gamma-interferon-inducing factor (IL-18) and IL-10 levels in patients with acute hepatitis and fulminant hepatic failure," Journal of gastroenterology and hepatology 17:285-294.

* cited by examiner

FIGURE 13-A
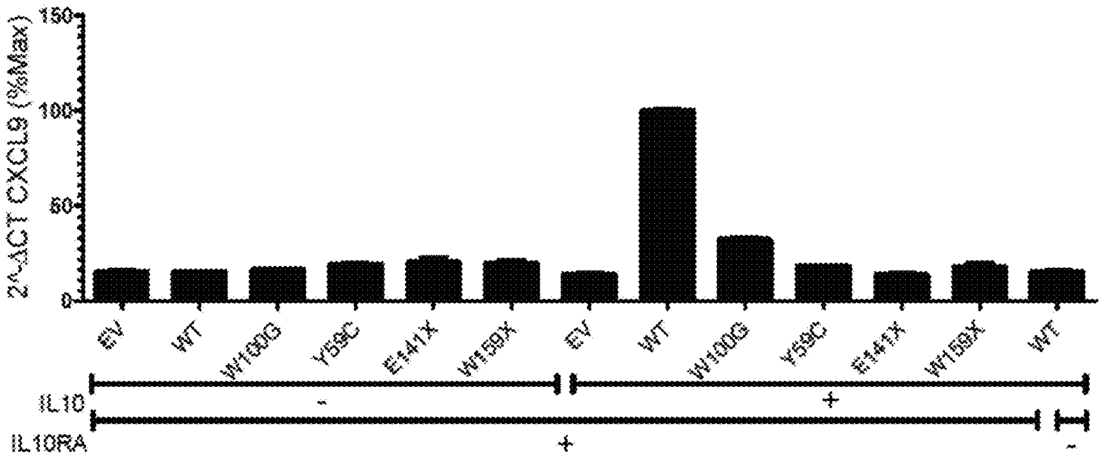
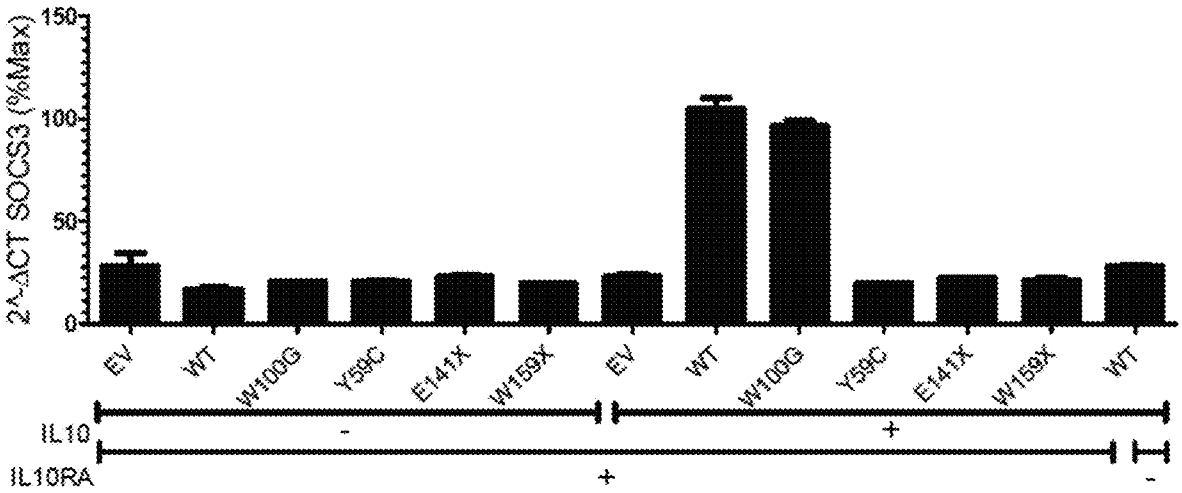

METHODS OF TREATING FULMINANT VIRAL HEPATITIS WITH AN IL-18 ANTAGONIST IN A PATIENT WITH AN IL-18BP VARIANT

CROSS REFERENCE TO RELATED APPLICATIONS

The present application is a national stage application, which claims priority from PCT Application No. PCT/US2020/036031, filed Jun. 4, 2020, which in turn, claims priority from U.S. Provisional Application Ser. No. 62/856,891 filed Jun. 4, 2019. Applicant claims the benefits of 35 U.S.C. § 120 as to the PCT application and priority under 35 U.S.C. § 119 as to the said U.S. Provisional application, and the entire disclosures of all applications are incorporated herein by reference in their entireties.

STATEMENT OF GOVERNMENT RIGHTS

This invention was made with government support under R01-AI091707 awarded by the National Institutes of Health (NIH). The government has certain rights in the invention.

FIELD OF THE INVENTION

The present invention relates generally to mutations and alterations in the inflammatory pathway that are associated with the development of fulminant viral hepatitis following viral infection, such as following hepatitis virus infection. The invention relates to methods for treating or ameliorating viral hepatitis comprising administering IL-18BP, IL-18 antagonist, IFNγ antagonist or inhibitor, and/or IL-10RB or an IL-10 antagonist.

BACKGROUND

Hepatitis A virus (HAV), hepatitis B virus (HBV), hepatitis C virus (HCV), and hepatitis E virus (HEV) are the most common liver-tropic viruses in humans. HAV and HEV typically cause an acute form of hepatitis, whereas HBV and HCV frequently cause chronic hepatitis, increasing the risk of cirrhosis and hepatocellular carcinoma (Guidotti and Chisari, 2006). HEV may also cause chronic infection (European Association for the Study of the Liver., 2017; Guidotti and Chisari, 2006). In rare cases, primary infections with these viruses, particularly for HAV, HBV, and HEV, can lead to fulminant viral hepatitis (FVH) (European Association for the Study of the Liver., 2017; Liu et al., 2001). FVH is defined as severe liver destruction in the absence of preexisting liver disease, leading to encephalopathy within eight weeks of the onset of the first symptoms (European Association for the Study of the Liver., 2017; Liu et al., 2001). It typically strikes children or young adults who are otherwise healthy, with normal immunity to other viruses, bacteria, fungi, and parasites. The actual prevalence and incidence of FVH worldwide are not precisely known, but previous studies have suggested that FVH develops in no more than 0.5% of individuals with symptomatic HAV infection (Lemon et al., 2018), with an estimated 1.5 million cases worldwide annually (Lemon et al., 2018). The global incidence of FVH due to HAV has therefore been estimated at about 1/1,000,000 per year, corresponding to a probable prevalence of 1/100,000. Patients with FVH have a very poor prognosis, with fewer than 25% surviving in the absence of liver transplantation. However, survival rates may reach 80% after liver transplantation (Lemon et al., 2018). FVH is typically sporadic, as opposed to epidemic, suggesting that it is not caused by a new more virulent viral strain (Ajmera et al., 2011; Fujiwara et al., 2001; Sasbon et al., 2010).

Therefore, there remains a need for improved methods of characterizing and treating fulminant viral hepatitis.

SUMMARY OF THE INVENTION

The present invention relates to methods of treating fulminant viral hepatitis. The invention relates generally to mutations and alterations in the inflammatory pathway that are associated with the development of fulminant viral hepatitis following viral infection, such as following hepatitis virus infection.

The invention identifies mutations in proteins binding IL-18 and the receptor for IL-10 which lead to fulminant viral hepatitis following hepatitis virus infection in individuals with these mutations. Alterations in the IL-18 pathway or in the IL-10 response pathway result in the development of FVH resulting from an altered viral response and inflammatory response with virus infection. Mutations in the IL-18BP protein and in the IL-10RB protein have been identified and characterized which result in FVH after hepatitis virus infection.

The invention relates to methods for treating or ameliorating viral hepatitis comprising administering IL-18BP, IL-18 antagonist, IFNγ antagonist or inhibitor, and/or IL-10RB or an IL-10 response modulator or mediator.

In one embodiment the invention includes a method of alleviating, treating or preventing fulminant viral hepatitis in a patient having a variant IL10RB gene or protein or a variant IL-18BP gene or protein. In an embodiment, the invention includes a method of treating fulminant viral hepatitis comprising administering an inhibitor or antagonist of IFNγ or a modulator or inhibitor of the IFN γ-mediated response in a patient in need thereof.

In an embodiment, a method of treating or ameliorating fulminant viral hepatitis is provided comprising administering to a patient with a hepatitis infection or a suspected hepatitis infection with one or more of IL-18BP, IL-18 antagonist, IFNγ antagonist or inhibitor, and/or IL-10RB or an IL-10 response mediator or modulator.

In an embodiment, a STAT1 activator is administered. In an embodiment, a STAT3 activator is administered. In an embodiment, a STAT1 activator and a STAT3 activator are administered. In an embodiment, IL-10RA is additionally administered or expressed.

In one embodiment, the invention includes a method of treating fulminant viral hepatitis in a patient having a variant IL18BP gene. In an embodiment, the invention includes a method of treating fulminant viral hepatitis in a patient having a variant IL18BP protein. This method includes the steps of administering IL-18BP or IL-18 antagonist to a patient in need thereof, or upregulating the expression of IL-18BP in a patient in need thereof.

The invention provides a method of treating or preventing fulminant viral hepatitis in a patient, said method comprising:

administering IL-18BP or IL-18 antagonist to a patient in need thereof, or upregulating the expression of IL-18BP in a patient in need thereof;

wherein the patient comprises cells having a IL-18BP gene variant.

In an embodiment, the IL-18BP variant results in loss of function of IL-18BP.

In an embodiment of the method, the IL-18BP gene variant comprises at least one of deletion of 10-25 nucleotides from the fourth and last intron, and deletion of 10-30 contiguous nucleotides from the fifth and last exon.

In an embodiment, the IL18BP gene variant comprises deletion of 19 nucleotides from the 4th and last intron, and deletion of 21 contiguous nucleotides from the 5th and last exon.

In one embodiment, the patient comprises the following IL-18BP gene variant: NG_029021.1:g.7854_7893del; NM_173042.2:c.508-19_528del.

In an embodiment, the patient is homozygous for the gene variant. In an embodiment, the patient is heterozygous for the gene variant.

In some embodiments, the patient cells further comprise at least one of the following: a missense mutation in the ADAMTS1 gene (NM_006988:p.Lys648Arg), a missense mutation in the SLC6A19 gene (NM_001003841.2: p.Val551Met), a missense mutation in the TM7SF2 gene (NM_003273.3:p.Ala36Gly), a missense mutation in the ZNF324 gene (NM_014347.2:p.Ile385Met), and a missense mutation in the ZNF814 gene (NM_001144989.1: p.His407Asp).

In some embodiments, the patient cells comprising the variant have at least 5%, 50%, or 75% more IL-18 as compared to cells from a person who is not suffering from fulminant viral hepatitis. In some embodiments, the patient cells comprising the variant have 10%-25%, 40%-60%, or 50-100% less IL-18BP as compared to cells from a person who is not suffering from fulminant viral hepatitis. In an embodiment, the patient cells comprising the variant have 50-100% less IL-18BP as compared to cells from a person who is not suffering from fulminant viral hepatitis.

In some embodiments, the patient cells comprising the variant have 10%-25%, 40%-60%, or 50-100% lower IL-18BP mRNA levels as compared to cells from a person who is not suffering from fulminant viral hepatitis.

In an embodiment of the invention, the cells are in the liver. In an embodiment of the invention, the cells are hepatocytes. In an embodiment, the cells comprise EBV-transformed B cells (EBV-B) from the patient. In an embodiment of the invention, liver cells or hepatocytes express or have genes encoding the mutant IL-18BP and/or IL-10RB.

In some embodiments of the method, IL-18 antagonist comprises a drug that interferes with IL-18 mediated NK cell activation.

In some embodiments of the method, upregulating IL-18BP expression comprises genetic engineering to increase expression of IL-18BP in the cells comprising the gene variant, wherein the increase is more than 10%, more than 25%, or more than 50% as compared to the level of expression of IL-18BP before the genetic engineering.

In one embodiment, the invention includes a method of treating, alleviating or preventing fulminant viral hepatitis in a patient having a variant IL10RB gene. In an embodiment, the invention includes a method of treating fulminant viral hepatitis in a patient having a variant IL-10RB protein. This method includes the steps of administering IL-10RB or IL-10 response mediator to a patient in need thereof, or upregulating the expression of IL-10RB in a patient in need thereof. In an embodiment, IL-10RA is additionally administered.

The invention provides a method of treating fulminant viral hepatitis in a patient, said method comprising:

administering IL-10RB or an IL-10 response mediator to a patient in need thereof, or upregulating the expression of IL-18BP in a patient in need thereof;

wherein the patient comprises cells having a IL-10RB gene or protein variant.

In an embodiment of the method, the IL10-RB gene variant encodes an IL-10RB protein variant or the IL-10RB protein variant comprises one or more amino acid substitution in the extracellular domain region of IL-10RB. In an embodiment, the IL10-RB gene variant encodes an IL-10 RB protein variant or the IL-10RB protein variant exhibits reduced or altered IL-10 response(s) or IL-10 mediated signaling.

In some embodiments, the patient has at least one of the following IL-10RB mutations: S31F, S58R, Y59C, C66Y, W100G, G193R, W204C. In some embodiments, the patient has at least one of the following IL-10RB mutations: S58R, Y59C, W100G. In an embodiment, the patient has the IL-10RB mutation W100G.

In an embodiment, the patient has a primary infection comprising a liver-tropic virus. In some embodiments, the patient has a primary infection selected from the group consisting of hepatitis A virus (HAV), hepatitis B virus (HBV), hepatitis C virus (HCV), and hepatitis E virus (HEV). In an embodiment, the patient has a primary infection selected from the group consisting of: HAV, HBV, and HEV. In an embodiment, the patient has a HAV primary infection.

In some embodiments of the methods of the invention, the method comprises further comprising administration of one or more antiviral therapies to the patient. In some embodiments, antiviral therapies include or may be selected from one or more of the agents entecavir (Baraclude), tenofovir (Viread), lamivudine (Epivir), adefovir (Hepsera), telbivudine (Tyzeka), sofosbuvir (Daklinza), voxilapresvir (Vosevi), and pibrentasvir (Mavyret).

In one embodiment, an antiviral agent such as an agent capable of reducing viral infection, inhibiting viral replication, reducing viral load, inhibiting hepatitis virus is further or additionally administered. In one embodiment, an inflammatory mediator is additionally administered. In one embodiment, an anti-inflammatory agent is additionally administered.

In some embodiments, the methods described herein include co-administration of one or more antiviral therapies to the patient. Antiviral therapies include entecavir (Baraclude), tenofovir (Viread), lamivudine (Epivir), adefovir (Hepsera), telbivudine (Tyzeka), sofosbuvir (Daklinza), voxilapresvir (Vosevi), and pibrentasvir (Mavyret).

In some embodiments of the method(s) provided herein, the patient is under the age of 30, 25, 20, 15, 10, or 5 years. In some embodiments, the patient is between the age of 5 and 25, 1 and 10, 10 and 20, or 10 and 15.

The invention provides a method for evaluating the IL-18BP and/or IL-10RB gene or encoded protein in a patient suspected of or determined to be suffering from a liver tropic virus infection. In some embodiments, the method further comprises administering to the patient, particularly wherein the patient is determined to have an altered gene or protein of IL-18BP and/or IL-10RB, such as or included as provided and described herein, one or more of IL-18BP or an IL-18 antagonist, an IFNγ antagonist or blocking agent, or IL-10RB or an IL-10 signaling mediator. In some embodiments, the method includes wherein the patient is determined to be at risk of fulminant viral hepatitis. In some embodiments, a method is provided for evaluating and treating a patient with a liver tropic virus infection so as to alleviate, treat or prevent fulminant viral hepatitis comprising assessing the gene encoding IL-18BP and/or IL-10RB in the patient, or assessing the IL-18BP and/or IL-10RB in the patient to determine whether IL-18BP is mutated to prevent IL-18 binding or result in loss of function of IL-18BP and/or to determine whether IL-10RB encoded protein is altered by substitution of one or more amino acids in the extracellular domain of IL-10RB such that response to IL-10 signaling is altered, the method further comprising administering to the patient one or more of IL-18BP or an IL-18 antagonist, an IFNγ antagonist or blocking agent, or IL-10RB or an IL-10 signaling mediator, whereby fulminant viral hepatitis is alleviated, treated or prevented in the patient.

In some embodiments, the IL-18 antagonist is an IL-18 antibody, or an agent, peptide, compound that blocks or interferes with IL-18 signaling. In some embodiments, the IL-10 signaling mediator is a compound, agent, small molecule, peptide, antibody or peptide mimetic which is capable of mediating IL-10 signaling or invoking an IL-10 response. In embodiments, the IL-10 signaling mediator is a compound, agent, small molecule, peptide, antibody or peptide mimetic which is capable of activating or phosphorylating STAT1. In embodiments, the IL-10 signaling mediator is a compound, agent, small molecule, peptide, antibody or peptide mimetic which is capable of activating or phosphorylating STAT3. In some embodiments, the IFNγ antagonist or agent is an IFNγ antibody, particularly a neutralizing IFNγ antibody. In some embodiments, the IFNγ antagonist or agent is an IFNγ antibody, or an active fragment thereof, particularly an IFNγ binding antibody fragment.

In some embodiments, the method comprises further comprising administration of one or more antiviral therapies to the patient, including wherein the patient is determined to be at risk of FVH, including by virtue of a mutant IL-18BP and/or a mutant IL-10RB. In some embodiments, antiviral therapies include or may be selected from one or more of the agents entecavir (Baraclude), tenofovir (Viread), lamivudine (Epivir), adefovir (Hepsera), telbivudine (Tyzeka), sofosbuvir (Daklinza), voxilapresvir (Vosevi), and pibrentasvir (Mavyret).

DESCRIPTION OF THE FIGURES

FIG. 12A to FIG. 12L Functional characterization of missense mutations reported in IL10RB in response to IL-10, IL-22, and IL-29 stimulation in overexpression system. (A) IL10RB mRNA measurement by qPCR in patient, a IL10RB-deficient patient and control cells. (B) IL-10RB surface expression by flow cytometry on patient cells, a IL10RB-deficient patient and controls. (C-E) depict representative western blot showing IL-10 stimulated patient and control cells stably transduced with IL10RA (C), and complemented with IL10RB-WT (D) in term of pSTAT1 and pSTAT3. Quantification of pSTAT1 and pSTAT3 (E). (F-G) depict representative western blot showing IL-22 stimulated patient and control cells stably transduced with IL10RA (F), and complemented with IL10RB-WT (G). (H-I) depict representative western blot showing IL-29 stimulated patient and control cells stably transduced with IFNLR1 (H), and complemented with IL10RB-WT (I). All stimulation experiments were carried out for 30 minutes. C=control, Pt=patient, EV=empty vector and p=phosphorylated.

FIG. 13A to FIG. 13C. Transcription levels of CXCL9 and SOCS3 or of CXCL9, assessed by qRT-PCR on IL10RB$^{KO}$ cells transfected with the different mutated alleles of IL10RB as noted and treated with (A) IL10, (B) IL22 or (C) IL29.

DETAILED DESCRIPTION

Figure 1A:
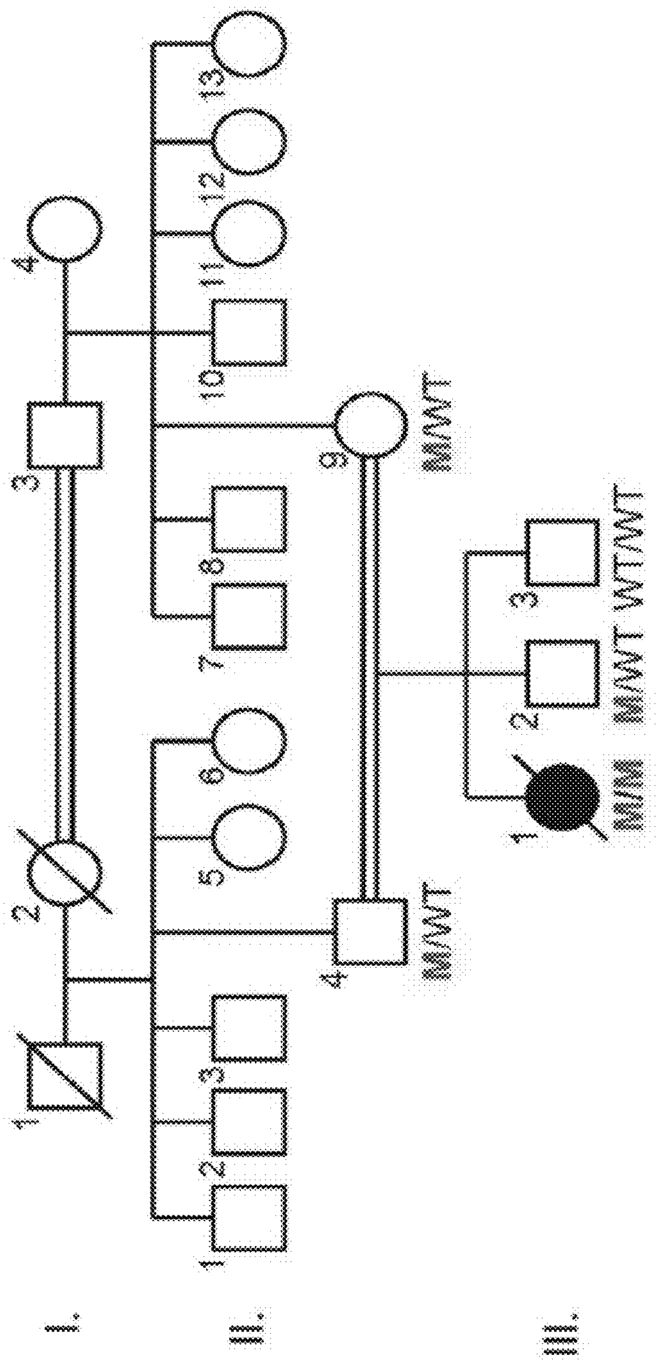
FIG. 1A to FIG. 1D. Homozygous 40-nucleotide deletion in IL18BP. A. Pedigree of the family affected by FVH due to HAV. The patient is shown in black, whereas healthy individuals are shown in white. Where available, IL18BP mutation (c.508-19_528del) status is indicated in red. WT=wild type; M=mutant. B. Familial segregation of the mutation and its homozygous state in the patient were confirmed by Sanger sequencing. C. Graph showing the predicted CADD scores and global allele frequencies of the mutation found in the patient with FVH (red circle) and missense variants of IL18BP (blue circles) for which homozygotes were reported in GnomAD. The CADD-MSC score and 90% confidence interval for IL18BP are indicated by a dashed line. D. The upper panel shows the exons (1-5) of the canonical IL18BP transcript; the bottom panel shows a diagram for IL-18BP. The signal peptide is highlighted in blue; the Ig domain is shown in red. Start and stop codons are indicated by an arrow and an asterisk, respectively. The c.508-19_528del is shown as a dashed box on the mRNA. The locations of IL18BP alleles from GnomAD are also shown on the protein diagram.

The present invention relates generally to methods of treating, alleviating or preventing fulminant viral hepatitis (FVH). The invention provides methods of treating. alleviating or preventing fulminant viral hepatitis (FVH), particularly in an individual or patient altered in the immune response or inflammatory response pathway. In embodiments of the method, an individual or patient may be altered in the expression, function, activity of IL-18BP, IL-10RB and/or or the IFNγ pathway. The invention provides mutations and alterations in the inflammatory pathway that are associated with the development of fulminant viral hepatitis following viral infection, such as following hepatitis virus infection. The invention provides mutations in the IL-18BP gene or protein and in the IL-10RB gene or protein which are associated with the occurrence of FVH in an individual or patient infected with a liver tropic virus, such as hepatitis virus, including hepatitis A virus. The invention provides approaches to assess an individual's or patient's susceptibility to or prevalence for FVH in the event of or upon infection with a liver tropic virus, such as hepatitis.

Fulminant viral hepatitis (FVH) is a rapid and severe impairment of liver functions (acute liver failure) with hepatic encephalopathy developing less than 8 weeks after the onset of jaundice, secondary to viral hepatitis. Clinically, FVH is observed as mainly due to hepatitis B virus (HBV), but also to hepatitis A virus (HAV). The present invention relates to methods of treating or preventing fulminant viral hepatitis in patients having a primary infection with a liver-tropic virus. Hepatitis A virus (HAV), hepatitis B virus (HBV), hepatitis C virus (HCV), and hepatitis E virus (HEV) are the most common liver-tropic viruses in humans. There is also the liver tropic hepatitis virus hepatitis D virus (HDV). A majority of the adeno-associated virus (AAV) serotype vectors exhibit liver tropism. Other viruses may cause fulminant hepatitis, for example Epstein-Barr virus (EBV) or herpes simplex virus. In addition, it is notable that coinfection of HBV/HCV with human immunodeficiency virus (HIV) infection and in AIDS patients is common. Estimated numbers of HBV and HCV infected subjects worldwide are significant (370 and 130 million subjects respectively) and of the 40 million known HIV positive subjects, 3 million are co-infected with HBV and 4.5 million with HCV (Williams R (2006) Hepatology 44:521-526).

Individuals or patients developing FVH upon or after or following or with viral infection, such as hepatitis virus infection, may be altered in the liver's anti-viral response pathway such that the virus and inflammatory response to the virus is not effective and significant liver pathology results, leading to FVH.

In embodiments of the invention, mutations in the IL-18BP gene or protein and mutations in the IL-10RB gene or protein are associated with FVH following hepatitis infection, such as hepatitis A virus infection. The IL-18BP mutations alter or block IL-18BP activity or IL-10RB activity. In some embodiments, IL-18BP is altered so that the mutant IL-18BP protein does not bind IL-18. In an embodiment, a deletion mutation in IL-18BP results in loss-of-function of IL-18BP. The IL-18BP mutations can result in uncontrolled IFNγ production and IFNγ-mediated pro-inflammatory activity. In some embodiments, IL-10RB mutations alter the ability of IL-10RB to bind as a receptor component to IL-10. In some embodiments, IL-10RB mutations alter the extracellular domain of IL-10RB. In some embodiments, IL-10 mediated response(s) are altered with IL-10RB mutation(s). In an embodiment, response to IL-10 is altered and response to IL-22 and IL-29 is not altered. In an embodiment, IL-10 mediated response(s) are altered such that FVH results with virus infection. IN an embodiment, IL-10 responses are altered such that IFNγ production and/or IFNγ-mediated activity and inflammation are not properly controlled or mediated.

Interleukin 18 (IL-18) is a strong inducer of Th-1 responses, interferon γ (IFN-γ) production, and stimulation of macrophages and natural killer (NK) cells. In fact, IL-18 was originally termed IFN-γ inducing factor. IL-18 binding protein (IL-18BP) is a natural secreted inhibitor of IL-18, has high-affinity binding for IL-18 and neutralizes the biologic activity of mature IL-18. This protein binds to and neutralizes IL-18, prevents the binding of IL-18 to its receptor, and thus inhibits IL-18-induced IFN-gamma production, resulting in reduced T-helper type 1 immune responses. IL-18BP is constitutively expressed and secreted in mononuclear cells and expression of IL-18BP can be enhanced by TFN-gamma.

Interleukin 10 receptor, beta subunit (IL-10 RB) is a subunit for the interleukin-10 receptor, also designated IL-10 Receptor subunit 2 (IL10R2) and cluster differentiation antigen CD Ag CDw210b. IL-10RB has the GeneID 3588 and UnitprotKB/SwissProt identifier Q08334. IL-10RB protein amino acid sequence (SEQ ID NO:2) is provided herein. The IL-10RB protein belongs to the cytokine receptor family and is an accessory chain essential for the active interleukin 10 receptor complex. Coexpression of IL-10RB and IL-10 receptor subunit 1 protein (also denoted IL-10RA) is required for IL10-induced signal transduction.

Interleukin-10 (IL-10) is a potent immunoregulatory cytokine that inhibits undesirable innate and acquired immune responses (Couper K N et al (2008) J Immunol 180: 5771-7; Moore K W et al (2001) Annu Rev Immunol 19: 683-765). Interleukin-10 is responsible for the limitation and eventual termination of inflammatory responses, which reduces the damage of self tissues in the process of pathogen eradication. In addition, IL-10 plays an important role in immune tolerance to protect self organs from autoimmunity. IL-10 antagonizes Th1 responses by inhibiting the production of IFN-γ. Interleukin-10 inhibits IFN-γ-induced monocyte/macrophage activation, subsequent cytokine production and the upregulation of costimulatory molecules.

IL-10 has emerged as a key immunoregulator during infection with viruses, bacteria, fungi, protozoa, ameliorating the excessive Th1 and CD8+ T cell responses (typified by overproduction of IFN-γ and TNF-α.) that are responsible for much of the immunopathology associated with infections including *Toxoplasma gondii, Trypanosoma* spp., *Plasmodium* spp., *Mycobacterium* spp., and HSV. Thus, ablation of IL-10 signaling results in the onset of severe, often fatal immunopathology in a number of infections (reviewed in Couper K N et al (2008) J Immunol 180: 5771-7). IL-10 is the founding member of the so-called IL-10 family (including IL-10, IL-19, IL-20, IL-22, IL-24 and IL-26). Interaction of IL-10 with its receptor leads to the activation of STAT transcription factors, including STAT3, the transcription factor downstream of IL-10.

In the context of the acute inflammatory response (AIR), IL-10 binding to IL-10R activates the IL-10/JAK1/STAT3 cascade, where phosphorylated STAT3 homodimers translocate to the nucleus within seconds to activate the expression of target genes In fact, upon IL-10 treatment multiple Stat proteins become simultaneously activated, including STAT1 and STAT3.

IFN-gamma (IFNγ), or type II interferon, is a cytokine that is critical for innate and adaptive immunity against viral, some bacterial and protozoal infections. IFNγ has long been recognized as a signature proinflammatory cytokine that plays a central role in inflammation and autoimmune disease. IFNγ is an important activator of macrophages and inducer of Class II major histocompatibility complex (MHC) molecule expression. Aberrant IFNγ expression is associated with a number of autoinflammatory and autoimmune diseases. The importance of IFNγ in the immune system stems in part from its ability to inhibit viral replication directly, and also from its immunostimulatory and immunomodulatory effects.

The present invention relates to methods of treating or preventing fulminant viral hepatitis in patients having a primary infection with a liver-tropic virus and an IL-18BP gene variant. In an embodiment, the invention relates to methods of treating or preventing fulminant viral hepatitis in patients having a primary infection with a liver-tropic virus and an IL-18BP gene or protein variant which results in IL-18BP loss of function.

Methods to treat, alleviate or prevent FVH may include administering IL-18BP or otherwise expressing functional IL-18BP. Methods may include administering an IL-18 inhibitor or antagonist, or agent that blocks IL-18 expression or activity. In some embodiments, the invention includes a method of treating fulminant viral hepatitis in a patient by administering IL-18BP or IL-18 antagonist to a patient in need thereof, or upregulating the expression of IL-18BP in a patient in need thereof; wherein the patient cells have a IL-18BP gene variant.

As used herein, fulminant viral hepatitis is characterized as a rapid and severe impairment of liver functions (acute liver failure) in a patient having a liver-tropic viral primary infection. This may develop less than 1, 2, 3, 4, 5, 6, 7, 8, 9, 10, 20 weeks after the onset of jaundice. In some instances, the rapid and severe impairment of liver functions (acute liver failure) develops between 1 and 20 weeks, 1 and 10 weeks, or 5 and 15 weeks after the onset of jaundice.

Without wishing to be bound by theory, it is believed that the activity of IL-18 is balanced by the presence of a high affinity, naturally occurring IL-18 binding protein (IL-18BP). In humans, increased disease severity can be associated with an imbalance of IL-18 to IL-18BP such that the levels of free IL-18 are elevated in the circulation. The loss of control or modulation of IL-18 via IL-18BP can thus result in uncontrolled IL-18 mediated activity and response, and can thus result in increased IFNγ productions, expression, activity or unregulated IFNγ.

The IL18BP gene encodes for the IL-18BP protein. The human wild type IL-18BP gene includes NC_000011.9 (71709955 . . . 71713965), on chromosome 11. (11 q13.4), based on human genome assembly GRCh37.p13.

Human IL-18BP is a 194 amino acid protein and has a Gene ID of 10068. Human IL-18BP sequence is known such as provided in NP_001034748.1, as indicated below (SEQ ID NO: 1):

```
  1 mtmrhnwtpd lsplwvlllc ahvvtllvra
    tpvsqtttaa tasvrstkdp cpsqppvfpa
 61 akqcpalevt wpevevplng tlslscvacs
    rfpnfsilyw lgngsfiehl pgrlwegsts
121 rergstgtql ckalvleqlt palhstnfsc
    vlvdpeqvvq rhvvlaqlwa glratlpptq
181 ealpsshssp qqqg
```

The IL18BP gene variant includes deletions in at least one region of the IL18BP gene. In some embodiments, this variant includes deletions in at least two regions of the IL18BP gene. In some embodiments, this variant includes deletions in three regions of the IL18BP gene. These regions include fourth intron, fifth exon, last exon, and last intron. As used herein, "IL18BP gene variant", "IL18BP variant", "IL-18BP gene variant", "IL-18BP variant", "gene variant", and "variant" are used interchangeable, unless otherwise specified.

The IL-18BP variant includes nucleotide deletions or amino acid deletions in the protein such that encoded IL-18BP or IL-18BP protein is not functional and is thus a loss of function variant or mutation. In an embodiment, the IL-18BP variant is incapable of binding, successfully interacting with, or modulating IL-18. In an embodiment, the IL-18BP variant is a nucleotide deletion such that expression of IL-18BP is lost at the mRNA level, or such that an altered form of IL-18BP mRNA is generated and is unstable or is rapidly or effectively degraded. The IL-18BP variant includes less than 100 nt deletions or less than 50 nt deletions. In some embodiments, the deletions include 2-100, 30-50, 35-45, or 25-55 nucleotides. In some embodiments the deletion includes nucleotides of the fourth and last intron and also nucleotides of the fifth and last exon such that normal splicing does not occur.

In some embodiments, the variant includes at least one of: deletion of 10-25 nucleotides from the fourth and last intron, and deletion of 10-30 contiguous nucleotides from the fifth and last exon. In some embodiments, the variant includes deletion of 10-25 nucleotides from the fourth intron and last intron, and deletion of 10-30 contiguous nucleotides from the fifth exon and last exon.

In some embodiments, the variant includes at least one of deletion of 19 nucleotides from the fourth intron and last intron, and deletion of 21 contiguous nucleotides from the 5 exon and last exon.

In some embodiments, the variant includes 40-nucleotide deletion including deletion of 19 nucleotides from the fourth intron and last intron, and deletion of 21 contiguous nucleotides from the 5 exon and last exon.

In some embodiments, the variant includes a deletion of 20-40, 30-40, or 40 nucleotides from 71712811-71712850, of NC_000011.9.

In some embodiments, the variant includes NG_029021.1:g.7854_7893del and/or NM_173042.2:c.508-19_528del.

In a preferred embodiment, the patient is homozygous for the IL18BP gene variant. In some embodiments the patient is heterozygous for the IL18BP gene variant.

In some embodiments, the patient has at least one of the following mutations: a missense mutation in the ADAMTS1 gene (NM_006988:p.Lys648Arg), a missense mutation in the SLC6A19 gene (NM_001003841.2:p.Val551Met), a missense mutation in the TM7SF2 gene (NM_003273.3:p.Ala36Gly), a missense mutation in the ZNF324 gene (NM_014347.2:p.Ile385Met), and a missense mutation in the ZNF814 gene (NM_001144989.1:p.His407Asp).

In some embodiments, the cells of the patient suffering from FVH have at least 25%, 50%, or 75% more IL-18 as compared to cells from a person who is not suffering from fulminant viral hepatitis.

In some embodiments, the cells of the patient suffering from FVH have 10%-25%, 40%-60%, or 50-100% less IL-18BP as compared to cells from a person who is not suffering from fulminant viral hepatitis.

In some embodiments, the cells of the patient suffering from FVH have 50-100% less IL-18BP as compared to cells from a person who is not suffering from fulminant viral hepatitis.

In some embodiments, the cells of the patient suffering from FVH have IL18BP mRNA levels that are 10%-25%, 40%-60%, or 50-100% lower as compared to cells from a person who is not suffering from fulminant viral hepatitis.

Without wishing to be bound by theory, it is believed that the IL18BP gene and protein variants described herein result in loss of expression and/or loss of function in IL-18BP, and therefore, result in increased IL-18 in patients having this variant.

Treatment of patients having a FVH as described herein include administering a therapeutically effective amount of IL-18BP or IL-18 antagonist to a patient in need thereof. Recombinant human IL-18BP may be used. An example of recombinant human IL-18BP includes Tadekinig Alfa, AB2 Bio Ltd, Switzerland. As used herein, IL-18 antagonists include any protein or small molecule or agent or compound, including a chemical compound or peptide mimetic, that inhibits IL-18 mediated activation of NK cells. IL-18 antagonists include any protein or small molecule or agent or compound, including a chemical compound or peptide mimetic, that inhibits IL-18 mediated induction of IFNγ production, expression or activity.

In an embodiment, anti-IFNγ agent such as an agent, compound, molecule, peptide, peptide mimetic capable of blocking IFNγ or interfering with IFNγ-mediated signaling is administered. Anti-IFNγ agents or compounds, such as IFNγ antibodies, including blocking or neutralizing antibodies are known and available in the art. Anti-IFNγ antibodies have been shown to potentiate or enhance the immunogenicity of recombinant adenovirus vector vaccine immunization (Jackson S S et al (2011) Clin Vaccine Immunology 18(11):1969-1978). Blocking anti-IFNγ antibodies have been shown to affect disease pathogenesis in some experimental model systems, including in experimental allergic encephalomyelitis (EAE), diabetes, malaria, lung tumors and Trypanosome infections (Billiau, A H et al (1988) J Immunol 140:1506-1510; Billiau, A H et al (1987) Eur J Immunol 17:1851-1854; Debray-Sachs, M et al (1991) J Autoimmun 4:237-248; Grau, G E et al (1989) Proc Natl Acad Sci U.S.A 86:5572-5574; Matthys, P et al (1991) Eur J Cancer 27:182-187; Torrico, F et al (1991) J Immunol 146:3626-3632; Uzonna, J E et al (1998) J Immunol 161:5507-5515).

IFNγ antibodies have been tested in several autoimmune diseases, including RA, MS, uveitis, Type I diabetes and various autoimmune skin diseases (alopecia areata, psoriasis vulgaris, vitiligo) (reviewed in Skurkovich B (2003) Curr Opin Mol Ther 5(1):52-57; Miller C H T et al (2009) Ann NY Acad Sci 1182:69-79). XMG1.2, a rat anti-mouse IFN-IgG1, was described by Cherwinski et al. (Cherwinski, H M et al (1987) J. Exp. Med. 166:1229-1244) and has been used extensively in vivo in mice with various dosing regimens (Uzonna, J E et al (1998) J Immunol 161:5507-5515). Other IFNγ antibodies that have been evaluated and are known include Fontolizumab (HuZAF) a humanized anti IFNγ antibody, and AMG811 (Amgen), a fully human IFNγ antibody.

In some embodiments, the treatment described herein is initiated to a patient having a primary liver-tropic viral infection within 1, 2, 3, 4, 5, 6, 7, 8, 9, 10, 20 weeks of the onset of jaundice. In some embodiments, the treatment described herein is initiated in a patient having a primary liver-tropic viral infection and between 1 and 20 weeks, 1 and 10 weeks, or 5 and 15 weeks after the onset of jaundice.

In some embodiments, a patient having a primary infection including a liver-tropic virus and an IL18BP gene variant is administered IL-18BP or IL-18 antagonist in the absence of the onset of jaundice. Liver function or liver enzymes may be monitored so as to determine the appropriate timing or amount of administration. Monitoring of liver function is well known and within the capability of one skilled in the art or in clinical practice.

In some embodiments, a treatment for a patient having a primary infection including a liver-tropic virus and an IL18BP gene variant includes upregulating the expression of IL-18BP. Upregulating the expression of IL-18BP in the cells include increasing the expression of IL-18BP more than 10%, more than 25%, or more than 50% as compared to the level of expression of IL-18BP before increasing the expression.

Upregulating the expression of IL-18BP may be accomplished by genetic engineering. As used herein, "genetic engineering" includes transcription, or transcription and translation, of exogenously supplied nucleic acid to prevent, palliate and/or cure a disease or diseases.

In some embodiments, the invention includes inhibiting or preventing the development of FVH in a patient having the IL18BP gene variant described herein by administering IL-18BP or IL-18 antagonist to a patient in need thereof, or upregulating the expression of IL-18BP in a patient in need thereof.

An IL-18 antagonist may include an IL-18 antibody such as a neutralizing antibody, or an agent, compound, peptide, small molecule, peptide mimetic that inhibits IL-18 activity, expression or IL-18 binding to IL-18BP. Some exemplary small molecule inhibitors of IL-18 have been identifies and are known. For example, three compounds (NSC201631, NSC80734, and NSC61610) have been identified that disrupt hIL-18 binding to the ectromelia virus IL-18BP (Krumm B et al (2017) Scientific Reports 7:483). Through cell-based bioassay, it was shown that NSC80734 inhibits IL-18-induced production of IFN-γ in a dose-dependent manner. GSK 1070803 (GlaxoSmithKline) is a humanized monoclonal antibody that blocks IL-18 (McKie E A et al (2016) PLoSOne 11(3):e0150018, doi:10.1371/journal-.pone.0150018).

The present invention relates to methods of treating or preventing fulminant viral hepatitis in patients having a primary infection with a liver-tropic virus and an IL10-RB gene or protein variant. In an embodiment, the invention relates to methods of treating or preventing fulminant viral hepatitis in patients having a primary infection with a liver-tropic virus and an IL-10RB gene or protein variant which results in an amino acid substitution in the extracellular domain of IL-10RB such that IL-10 mediated response is altered. In an embodiment, with the IL-10RB gene or protein variant, binding to IL-10 is altered. In an embodiment, response to IL-10 is altered and is hypomorphic, such that a partial loss of gene function, such as through reduced protein or RNA expression or reduced functional performance, but not a complete loss results. In one embodiment, some IL-10 mediated response but reduced response is demonstrated. In one embodiment, response to IL-10 is altered, but response to IL-22 and to IL-29 interleukins is normal or about the same as for a wild type IL-10RB protein. In one embodiment an IL-10RB mutation, such as a single amino acid substitution or a missense mutation is present whereby the IL-10RB mutant or variant does not respond to IL-10 but does respond to IL-22 and IL-29.

in an embodiment, the IL-10RB mutation is a substitution mutation of amino acid 100 of IL-10RB. In an embodiment, the IL-10RB mutation is a substitution mutation of the tryptophan amino acid 100 of IL-10RB. In an embodiment, the tryptophan is substituted with glycine, alanine, leucine, isoleucine or methionine. In an embodiment, the tryptophan is substituted with glycine or alanine. In an embodiment, the tryptophan is substituted with glycine. In an embodiment, the IL-10RB mutation corresponds to that of designated IL-10RB W100G or W100 and is a missense mutation resulting in a Tryptophan to Glycine single amino acid substitution mutation at amino acid 100 in the IL-10RB protein. The IL-10RB protein sequence is provided herein and as SEQ ID NO:2.

In an embodiment, the IL-10RB mutation is an extracellular domain missense mutation such that response to IL-10 is altered or absent. In an embodiment, the IL-10RB mutation is an extracellular domain missense mutation selected from S58R and Y59C. In an embodiment, the IL-10RB mutation is an extracellular domain missense mutation selected from S58R and Y59C, wherein the IL-10RB alleles do not respond to IL-10 but do respond to IL-22 and IL-29.

Methods to treat, alleviate or prevent FVH may include administering IL-10RB or otherwise expressing functional IL-10RB. Methods may include administering an IL-10 binding agent or agent that mediates IL-10 activity. Methods may include administering, expressing or increasing expression of the other IL-10 receptor subunit IL-10RA. Methods may include administering an IL-10 binding agent or agent that mediates IL-10 phosphorylation of STAT1. Methods may include administering an agent that mediates IL-10 phosphorylation of STAT1. Methods may include administering an agent that mediates IL-10 phosphorylation of STAT3. Methods may include administering an agent that mediates IL-10 phosphorylation of STAT1 and STAT3. Methods may include administering an agent that mediates activation of STAT1. Methods may include administering an agent that mediates activation of STAT3. Methods may include administering an agent that mediates activation of STAT1 and STAT3. Methods may include administering an agent that mediates IL-10 stimulation or IL-10 mediated stimulation of CXCL9. Methods may include administering an agent that stimulates CXCL9 expression or activity. In some embodiments, the invention includes a method of treating fulminant viral hepatitis in a patient by administering IL-10RB or IL-10 binding agent or IL-10 mediator to a patient in need thereof, or upregulating the expression of IL-10RB wild type or expressing IL-10RB wild type protein in a patient in need thereof; wherein the patient cells have a IL-10RB gene variant.

Without wishing to be bound by theory, it is believed that the activity of IL-10 is balanced by the presence of the IL-10 receptor subunits IL-10RB and IL-10RA which bind IL-10 and can mediate IL-10 activity and response. In humans, increased disease severity can be associated with an imbalance of IL-10 to IL-10RB such that the levels of free IL-10 are elevated in the circulation or such that IL-10 mediated signaling is altered or reduced. This can result in uncontrolled or alteration of control and mediation of other signaling pathways such as the IFNγ-mediated pathway and viral response and inflammatory response. The loss of control or modulation of IL-10 via IL-10RB can thus result in lack of IL-10 mediated controls or responses or altered IL-10 mediated response(s) and/or in uncontrolled IFNγ mediated activity and response, and can thus result in increased IFNγ productions, expression, activity or unregulated IFNγ.

The IL10RB gene and protein variant includes one or more substitution(s) or missense mutation(s) in at least one region of the IL-10RB, such as in the extracellular domain of IL-10RB. In some embodiments, this variant includes at least one substitution or missense mutation in at least one region of the IL-10RB, such as in the extracellular domain of IL-10RB. In some embodiments, this variant includes at least one substitution or missense mutation in the extracellular domain of IL-10RB. In some embodiments, the variant includes one or more amino acid substitution in the extracellular domain of IL-10RB such that IL-10 binding and/or IL-10 mediated response is altered. In some embodiments, the variant includes one or more amino acid substitution in the extracellular domain of IL-10RB such that IL-10 binding and/or IL-10 mediated response is altered or blocked, including wherein IL-22 and IL-29 response is maintained or close to that mediated by wild type IL-10RB. As used herein, "IL10RB gene variant", "IL10RB variant", "IL-10RB gene variant", "IL-10RB variant", "gene variant", and "variant" are used interchangeable, unless otherwise specified.

In a preferred embodiment, the patient is homozygous for the IL10RB gene variant and expresses only altered IL-10RB protein, such as having an amino acid substitution in IL-10RB. In some embodiments the patient is heterozygous for the IL10RB gene variant.

In some embodiments, the patient has at least one of the following mutations: S31F, S58R, Y59C, C66Y, W100G, G193R, W204C. In some embodiments, the patient has at least one of the following mutations: S58R, Y59C, W100G. In an embodiment, the patient has the mutation W100G.

Treatment of patients having a FVH as described herein include administering a therapeutically effective amount of IL-10RB or an IL-10 binding agent or an IL-10 mediator to a patient in need thereof. Recombinant human IL-10RB may be used. Treatment of patients having a FVH as described herein include administering a therapeutically effective amount of IL-10RB and IL-10RA or an IL-10 binding agent to a patient in need thereof. Recombinant human IL-10RB may be used. A gene therapy vector, such as a liver tropic vector such as AAV may be utilized expressing IL-10RB. In an embodiment, a gene therapy vector, such as a liver tropic vector such as AAV may also be utilized expressing IL-10RA.

In some embodiments, the treatment described herein is initiated to a patient having a primary liver-tropic viral infection within 1, 2, 3, 4, 5, 6, 7, 8, 9, 10, 20 weeks of the onset of jaundice. In some embodiments, the treatment described herein is initiated in a patient having a primary liver-tropic viral infection and between 1 and 20 weeks, 1 and 10 weeks, or 5 and 15 weeks after the onset of jaundice.

In some embodiments, a patient having a primary infection including a liver-tropic virus and an IL10RB gene variant is administered IL-10RB or an IL-10 binding agent or an IL-10 mediator in the absence of the onset of jaundice. Liver function or liver enzymes may be monitored so as to determine the appropriate timing or amount of administration.

In some embodiments, a treatment for a patient having a primary infection including a liver-tropic virus and an IL10RB gene variant includes upregulating the expression or activity of IL-10RB. Upregulating the expression of IL-10RB in the cells include increasing the expression of IL-10RB more than 10%, more than 25%, or more than 50% as compared to the level of expression of IL-10RB before increasing the expression. In an embodiment, expression or activity of IL-10RA is also or concomitantly upregulated so as to mediate IL-10 binding and IL-10 mediated signaling.

Upregulating the expression of IL-10RB or expression of a wild type IL-10RB may be accomplished by genetic engineering. As used herein, "genetic engineering" includes transcription, or transcription and translation, of exogenously supplied nucleic acid to prevent, palliate and/or cure a disease or diseases.

In an embodiment, anti-IFNγ agent such as an agent, compound, molecule, peptide, peptide mimetic capable of blocking IFNγ or interfering with IFNγ-mediated signaling is administered. Anti-IFNγ agents or compounds, such as IFNγ antibodies, including blocking or neutralizing antibodies are known and available in the art, including as described herein.

As used herein, "inhibiting the development of", "reducing the risk of", "prevent", "preventing", and the like refer to reducing the probability of developing a FVH in a patient who may not have a primary liver-tropic viral infection, but may have a genetic predisposition to developing FVH. As used herein, "at risk", "susceptible to", or "having a genetic predisposition to", refers to having a propensity to develop FVH. For example, a patient having the IL18BP gene variant described herein has increased risk (e.g., "higher predisposition") of developing the FVH relative to a control patient having a "lower predisposition" (e.g., a patient without the IL18BP gene variant described herein).

In certain embodiments, the patient is a human 0 to 6 months old, 6 to 12 months old, 1 to 5 years old, 5 to 10 years old, 5 to 12 years old, 10 to 15 years old, 15 to 20 years old, 13 to 19 years old, 20 to 25 years old, 25 to 30 years old, 20 to 65 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old.

In certain embodiments, the patient is under the age of 30, 25, 20, 15, 10, or 5 years.

In certain embodiments, the patient is between the age of 5 and 25, 1 and 10, 10 and 20, or 10 and 15.

In some embodiments, the invention is directed to a method of treating FVH in a patient having an HAV, HBV, HCV, or HEV primary infection. In some embodiments, the invention includes a method of treating FVH in a patient having an HAV, HBV, or HEV primary infection. In some embodiments, the invention includes a method of treating FVH in a patient having an HAV, HBV, or HCV primary infection. In some embodiments, the invention includes a method of treating FVH in a patient having a HBV or HCV primary infection. In some embodiments, the invention includes a method of treating FVH in a patient having a HBV and HCV primary infection. In some embodiments, the invention includes a method of treating FVH in a patient having an HAV primary infection.

In some embodiments, the method described herein include co-administration of one or more antiviral therapies to the patient. Antiviral therapies include entecavir (Baraclude), tenofovir (Viread), lamivudine (Epivir), adefovir (Hepsera), telbivudine (Tyzeka), sofosbuvir (Daklinza), voxilapresvir (Vosevi), and pibrentasvir (Mavyret).

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

As used herein, administering includes administering a therapeutically effective dose. As used herein, the phrase "therapeutically effective dose" or "therapeutically effective amount" refers to a dose or amount of an agent that provides for an improvement in either the onset of symptoms or the progression of symptoms associated FVH in comparison to a patient that has not received the agent.

Undesirable effects, e.g. side effects, are sometimes manifested along with the desired therapeutic effect; hence, a practitioner balances the potential benefits against the potential risks in determining what an appropriate "effective amount" is. The exact amount required will vary from patient to patient, depending on the species, age and general condition of the patient, mode of administration and the like. Thus, it may not be possible to specify an exact "effective amount". However, an appropriate "effective amount" in any individual case may be determined by one of ordinary skill in the art using only routine experimentation.

As used herein the terms treatment, treat, or treating refer to a method of reducing the effects of FVH or symptom of FVH. Thus in the disclosed method, treatment can refer to a 10%, 20%, 30%, 40%, 50%, 60%, 70%, 80%, 90%, or 100% reduction in the severity of an FVH or symptom of FVH. For example, a method for treating FVH is considered to be a treatment if there is a 10% reduction in one or more symptoms of FVH in a patient as compared to a control. Thus the reduction can be a 10%, 20%, 30%, 40%, 50%, 60%, 70%, 80%, 90%, 100%, or any percent reduction in between 10% and 100/6 as compared to native or control levels. It is understood that treatment does not necessarily refer to a cure or complete ablation of the infection, condition, or symptoms of the infection or condition.

As used herein, the terms prevent, preventing, and prevention of a FVH refer to an action, for example, administration of a compound described herein, that occurs before or at about the same time a patient begins to show one or more symptoms of FVH, which inhibits or delays onset or exacerbation of one or more symptoms of the disease or disorder. As used herein, references to decreasing, reducing, or inhibiting include a change of 10%, 20%, 30%, 40%, 50%, 60%, 70%, 80%, 90% or greater as compared to a control level. Such terms can include but do not necessarily include complete elimination.

The term "antibody" describes an immunoglobulin whether natural or partly or wholly synthetically produced. The term also covers any polypeptide or protein having a binding domain which is, or is homologous to, an antibody binding domain. CDR grafted antibodies are also contemplated by this term. An "antibody" is any immunoglobulin, including antibodies and fragments thereof, that binds a specific epitope. The term encompasses polyclonal, monoclonal, and chimeric antibodies. The term "antibody(ies)" includes a wild type immunoglobulin (Ig) molecule, generally comprising four full length polypeptide chains, two heavy (H) chains and two light (L) chains, or an equivalent Ig homologue thereof (e.g., a camelid nanobody, which comprises only a heavy chain); including full length functional mutants, variants, or derivatives thereof, which retain the essential epitope binding features of an Ig molecule, and including dual specific, bispecific, multispecific, and dual variable domain antibodies; Immunoglobulin molecules can be of any class (e.g., IgG, IgE, IgM, IgD, IgA, and IgY), or subclass (e.g., IgG1, IgG2, IgG3, IgG4, IgA1, and IgA2). Also included within the meaning of the term "antibody" are any "antibody fragment". As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic.

An "antibody fragment" refers to and includes a molecule comprising at least one polypeptide chain that is not full length, including (i) a Fab fragment, which is a monovalent fragment consisting of the variable light (VL), variable heavy (VH), constant light (CL) and constant heavy 1 (CH1) domains; (ii) a F(ab')2 fragment, which is a bivalent fragment comprising two Fab fragments linked by a disulfide bridge at the hinge region; (iii) a heavy chain portion of an Fab (Fd) fragment, which consists of the VH and CH1 domains; (iv) a variable fragment (Fv), which consists of the VL and VH domains of a single arm of an antibody, (v) a domain antibody (dAb) fragment, which comprises a single variable domain (Ward, E. S. et al., Nature 341, 544-546 (1989)); (vi) a camelid antibody; (vii) an isolated complementarity determining region (CDR); (viii) a Single Chain Fv Fragment wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (ix) a diabody, which is a bivalent, bispecific antibody in which VH and VL domains are expressed on a single polypeptide chain, but using a linker that is too short to allow for pairing between the two domains on the same chain, thereby forcing the domains to pair with the complementarity domains of another chain and creating two antigen binding sites (WO94/13804; P. Holliger et al Proc. Natl. Acad. Sci. USA 90 6444-6448, (1993)); and (x) a linear antibody, which comprises a pair of tandem Fv segments (VH-CH1-VH-CH1) which, together with complementarity light chain polypeptides, form a pair of antigen binding regions; (xi) multivalent antibody fragments (scFv dimers, trimers and/or tetramers (Power and Hudson, J Immunol. Methods 242: 193-204 9 (2000)); (xii) a minibody, which is a bivalent molecule comprised of scFv fused to constant immunoglobulin domains, CH3 or CH4, wherein the constant CH3 or CH4 domains serve as dimerization domains (Olafsen T et al (2004) Prot Eng Des Sel 17(4):315-323; Hollinger P and Hudson P J (2005) Nature Biotech 23(9):

1126-1136); and (xiii) other non-full length portions of heavy and/or light chains, or mutants, variants, or derivatives thereof, alone or in any combination.

Exemplary antibody molecules are intact immunoglobulin molecules, substantially intact immunoglobulin molecules and those portions of an immunoglobulin molecule that contains the paratope, including those portions known in the art as Fab, Fab', $F(ab')_2$ and F(v), which portions are preferred for use in the therapeutic methods described herein.

Antibodies may also be bispecific, wherein one binding domain of the antibody recognizes a target of reference in the invention, and the other binding domain has a different specificity, e.g. to recruit an effector function or the like. Bispecific antibodies of use in the present invention include wherein one binding domain of the antibody recognizes a target of reference in the invention, including a fragment thereof, and the other binding domain is a distinct antibody or fragment thereof, including that of a distinct pathway antibody, immunomodulatory antibody, or viral antibody. The other binding domain may be an antibody that recognizes or targets a particular cell type, as in a liver cell.

Further, unless expressly stated to the contrary, "or" refers to an inclusive "or" and not to an exclusive "or". For example, a condition A or B is satisfied by any one of the following: A is true (or present) and B is false (or not present), A is false (or not present) and B is true (or present), and both A and B are true (or present).

Throughout this specification, quantities are defined by ranges, and by lower and upper boundaries of ranges. Each lower boundary can be combined with each upper boundary to define a range. The lower and upper boundaries should each be taken as a separate element.

As used herein, the term "patient" and "subject" may be used interchangeably. In a preferred embodiment, the subject or patient is a human.

As used herein, a "patient in need thereof" includes a patient having a primary liver-tropic viral infection.

Additionally, any examples or illustrations given herein are not to be regarded in any way as restrictions on, limits to, or express definitions of any term or terms with which they are utilized. Instead, these examples or illustrations are to be regarded as being described with respect to one particular embodiment and as being illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such nonlimiting examples and illustrations includes, but is not limited to: "for example," "for instance," "e.g.," and "in one embodiment."

In this specification, groups of various parameters containing multiple members are described. Within a group of parameters, each member may be combined with any one or more of the other members to make additional sub-groups. For example, if the members of a group are a, b, c, d, and e, additional sub-groups specifically contemplated include any one, two, three, or four of the members, e.g., a and c; a, d, and e; b, c, d, and e; etc.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

Example 1

Inherited IL-18BP Deficiency in Human Fulminant Viral Hepatitis

Fulminant viral hepatitis (FVH) is a devastating and unexplained condition that strikes otherwise healthy individuals during primary infection with common liver-tropic viruses. We report a child who died of FVH upon infection with hepatitis A virus (HAV) at age 11 yr and who was homozygous for a private 40-nucleotide deletion in IL18BP, which encodes the IL-18 binding protein (IL-18BP). This mutation is loss-of-function, unlike the variants found in a homozygous state in public databases. We show that human IL-18 and IL-18BP are both secreted mostly by hepatocytes and macrophages in the liver. Moreover, in the absence of IL-18BP, excessive NK cell activation by IL-18 results in uncontrolled killing of human hepatocytes in vitro. Inherited human IL-18BP deficiency thus underlies fulminant HAV hepatitis by unleashing IL-18. These findings provide proof of principle that FVH can be caused by single-gene inborn errors that selectively disrupt liver-specific immunity. They also show that human IL-18 is toxic to the liver and that IL-18BP is its antidote.

Rare familial cases of FVH have been reported, including two young siblings from a Turkish family, three young brothers from an Iranian family, and two elderly brothers from a Japa-nese family who developed FVH within weeks of each other following primary HAV infections in their siblings (Durst et al., 2001; Yalniz et al., 2005; Yoshida et al., 2017). In all three families, several relatives of the patients had presented viral hepatitis with a benign course. Inbred strains of mice display differences in susceptibility to mouse hepatitis virus 3 (MHV3; Wege et al., 1982). Upon infection with MHV3, fully susceptible strains (e.g., C57B1/6J) die from FVH, semisusceptible strains (e.g., C3H/St) develop acute and then chronic hepatitis, and fully resistant strains (e.g., A/J) display no signs of liver disease (MacPhee et al., 1985). These observations suggest that host genetic factors may underlie FVH. The lack of FVH in patients with any of the >350 known primary immunodeficiencies (Picard et al., 2018) suggests that FVH is unlikely to result from inborn errors that broadly disrupt innate and/or adaptive immunity. Instead, previous discoveries that other severe viral diseases striking otherwise healthy individuals, such as epidermodysplasia verruciformis, fulminant EBV disease, herpes simplex encephalitis, severe pulmonary influenza, severe rhi-novirus respiratory disease, and severe varicella zoster virus disease, can result from single-gene inborn errors of protective immunity to specific viruses in specific cell types or tissues (Casanova, 2015a,b; Casanova and Abel, 2018) suggest that FVH may result from inborn errors selectively disrupting immunity to hepatitis viruses in the liver. We tested this hypothesis by searching for genetic etiologies of FVH by whole-exome sequencing (WES) in a small cohort of patients.

RESULTS

A Private IL18BP Variation in a Patient with Fulminant Viral Hepatitis

We performed whole-exome sequencing (WES) on leukocyte genomic DNA (gDNA) from three siblings born to Algerian parents living in France: a girl who died from FVH due to HAV at 11 years of age with no signs of previous chronic or acute liver disease of any type, and her two brothers, who had experienced benign HAV infections (Materials and Methods). WES revealed a high rate of homozygosity among the siblings (5.60 to 6.51%), indicating that this family was consanguineous. We therefore hypothesized that a genetic etiology for FVH in this family would display autosomal recessive (AR) inheritance with complete penetrance. We thus searched for very rare (Minor allele frequency (MAF)<0.001) homozygous non-synonymous variants present in the patient, but not in her two siblings (Table 1). Six genes had variants meeting these criteria (Table 2). We prioritized candidate genes for further studies based on (i) the known function of the gene in the liver and/or immunity and (ii) the predicted deleteriousness of the variations. IL18BP, encoding the interleukin-18 binding protein, was the most plausible disease-causing gene, as (i) it encodes a constitutively secreted, naturally circulating neutralizer of the cytokine IL-18 (Aizawa et al., 1999; Novick et al., 1999), the mouse ortholog of which is known to be toxic to the liver (Okamura et al., 1995), and (ii) the patient carried a 40-nucleotide (nt) homozygous deletion centered on an intron-exon boundary within this gene.

None of the other five variants identified, all of which were missense, had ever been associated with the liver or with immunity (Table 3). Moreover, the IL18BP variant (NG_029021.1:g.7854_7893del; NM_73042.2:c.508-19_528del) was not found in any public database (1000 Genomes, dbSNP, GnomAD, and Bravo) or in our in-house database of more than 4,000 exomes, including 65 from unrelated Algerians and at least 1,000 from North Africans (as confirmed by principal component analysis, as in our patient).

Homozygosity for a 40-Nucleotide Deletion in IL18BP Segregates with Disease

Figure 1B:
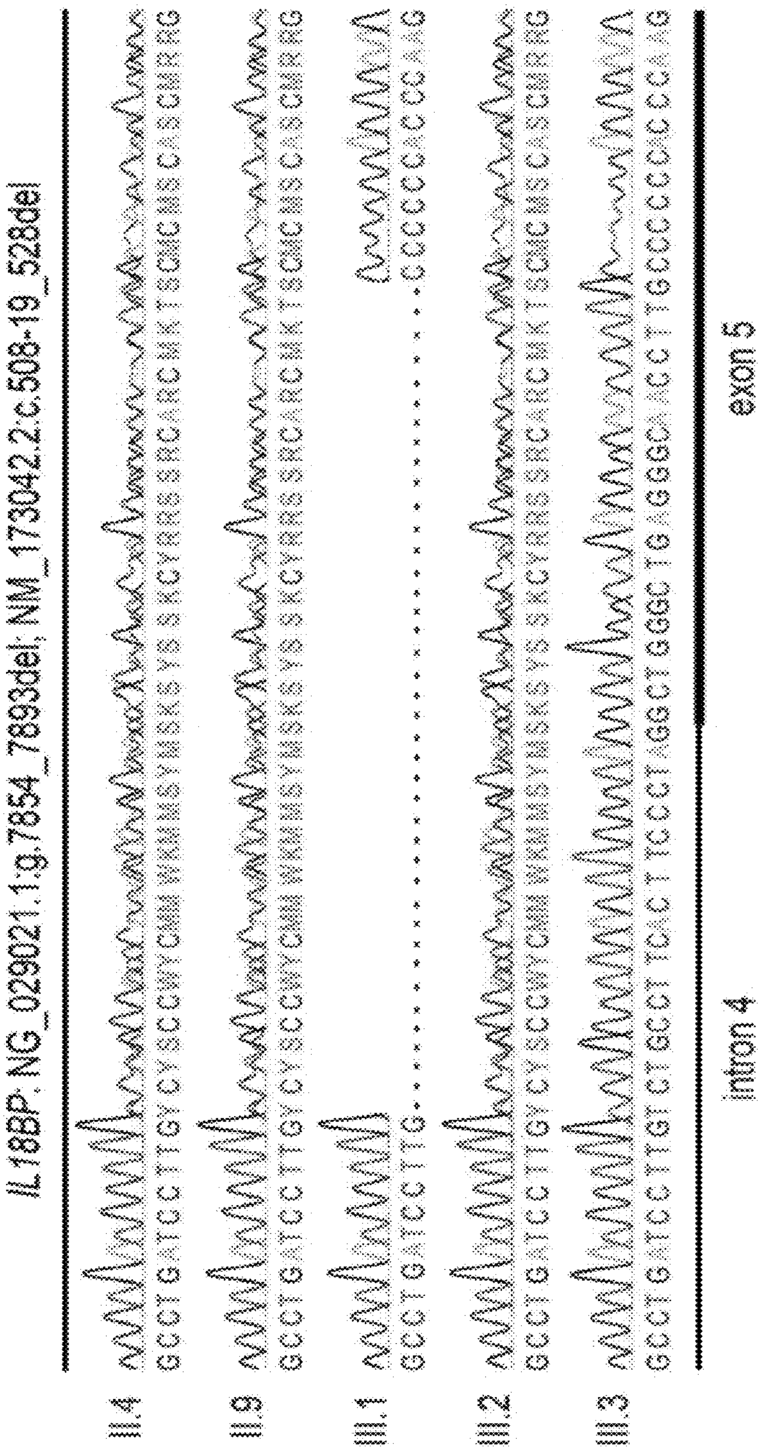
Figure 1C:
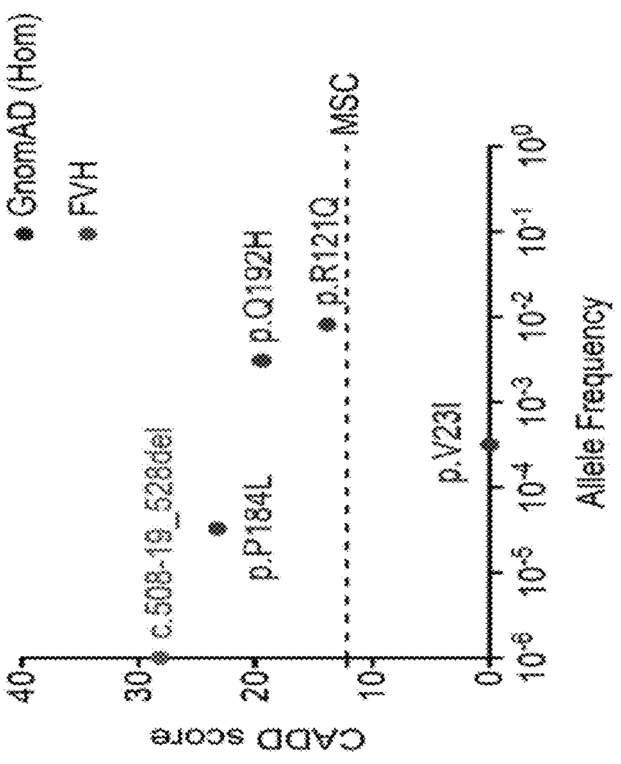

We confirmed, by Sanger sequencing, that the familial segregation of the mutant IL18BP allele was consistent with an AR mode of inheritance with complete penetrance, as both parents and one of the healthy siblings were heterozygous for the mutation, whereas the other sibling did not carry the mutation (FIG. 1A-B). This mutation, c.508-19_528del, deletes 19 nt from the 4th and last intron and 21 contiguous nt from the 5th and last exon. It is predicted, in silico, to be highly deleterious, with a combined annotation-dependent depletion (CADD) score of 28.2, which is above the mutation significance cutoff (MSC) score of 12.2 for IL18BP (FIG. 1C). IL18BP has a gene damage index (GDI) of 2.05, indicating a moderate level of accumulation of non-synonymous mutations in the general population. Indeed, GnomAD includes only four missense variants (p.V23I, p.R121Q, p.P184L, and p.Q192H) in the homozygous state. Their CADD scores range from 0.001 to 23.3 (FIG. 1C). Two substitutions, p.R121Q and p.Q192H, are common among Africans, with a MAF of 8.23% and 3.11%, respectively, and the patient was also found to be homozygous for p.R121Q. The other two missense variants, p.V23I and p.P184L, have a global MAF<0.1% (Figure C). Finally, none of the databases included copy number variations (CNVs) encompassing IL18BP in the homozygous state. Collectively, these findings suggested that homozygosity for the private and probably deleterious c.508-19_528del allele in IL18BP may be the underlying cause of FVH in this patient.

Mutation c.508-19_528Del Causes Aberrant IL18BP mRNA Splicing

Figure 1D:
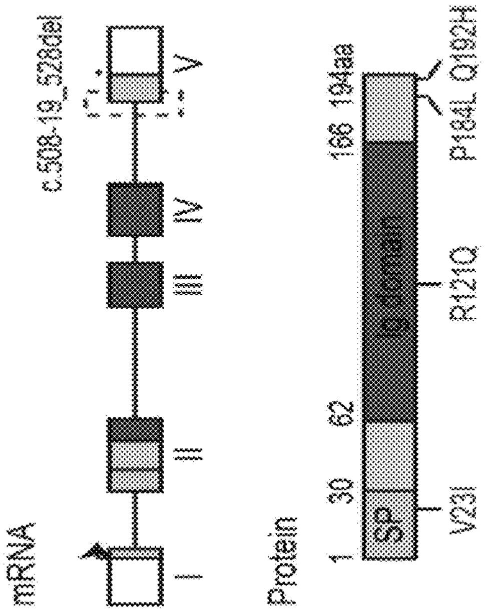
Figure 2B:
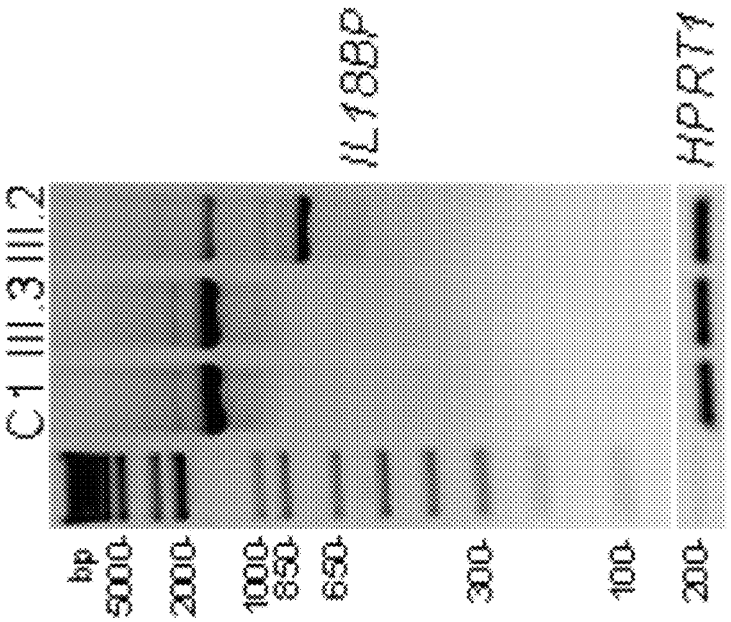
FIG. 2A to FIG. 2G. Impact of the IL18BP:c.508-19_528del on gene expression and function. A. RT-qPCR showing IL18BP levels normalized against endogenous GAPDH expression in EBV-B cell lines from six healthy controls (black), the WT sibling (III.3, purple), and heterozygous family members: brother (III.2, red), father (II.4, blue) and mother (I1.9, green). Relative IL18BP expression was determined by normalization against the mean value for WT cells, set to 1 (indicated by a dashed line). The values shown are the means of two independent experiments performed in duplicate. B. Agarose gel electrophoresis showing aberrant splicing of the IL18BP mRNA in 3' RACE on EBV-B cells from the heterozygous sibling (III.2), relative to a control cell line (C1) and the WT sibling (III.3). HPRT1 was used as the housekeeping gene control. C. The nested PCR products from FIG. 2B were cloned and colonies were sequenced. Diagram (left) and percentages (right) of WT (gray) and mutant (M1 in blue, M2 in red and M3 in green) splice variants of the IL18BP transcript are shown. The start codon is located at position 1, and the stop codon is at 585, shown by an asterisk, on the WT transcript. The polyadenylation site is at position 1252 and indicated by ($A_n$). D. Expression levels of each splice variant (WT in gray, M1 in blue, M2 in red and M3 in green) were determined and normalized against endogenous GAPDH expression levels by RT-qPCR on EBV-B cells from two healthy controls (C2-C3) and family members. Graph shows the copy numbers of the mutant splice variants relative to the mean copy number for the WT allele in EBV-B cells from C2, C3 and III.3, which was set to 1 (indicated by a dashed line). The values are the means SEM of two independent experiments performed in duplicate. E-F. Representative immunoblot images showing levels of the WT and mutant IL-18BP alleles, M1-M3 (E.) and four missense alleles from GnomAD (F.) in concentrated supernatants from transiently transfected COS7 cells. Immunoblotting was performed with the His tag antibody (top), and the membrane was then stripped and probed with the IL-18BP antibody (bottom). G. IL-18BP bioassay: IFN-γ production was measured in NK-92 cells stimulated with recombinant human IL-12 (100 pg/mL), IL-18 (10 ng/mL) and/or concentrated supernatants (100 μg/mL of total protein) of COS7 cells transiently transfected with either empty vector or the constructs expressing indicated IL-18BP variants. Graph is presented on a logarithmic scale with base of 10. The data are the means±SEM of two independent experiments performed in duplicate using the supernatants shown in FIGS. 2E-F and SI F-G.
Figure 2A:
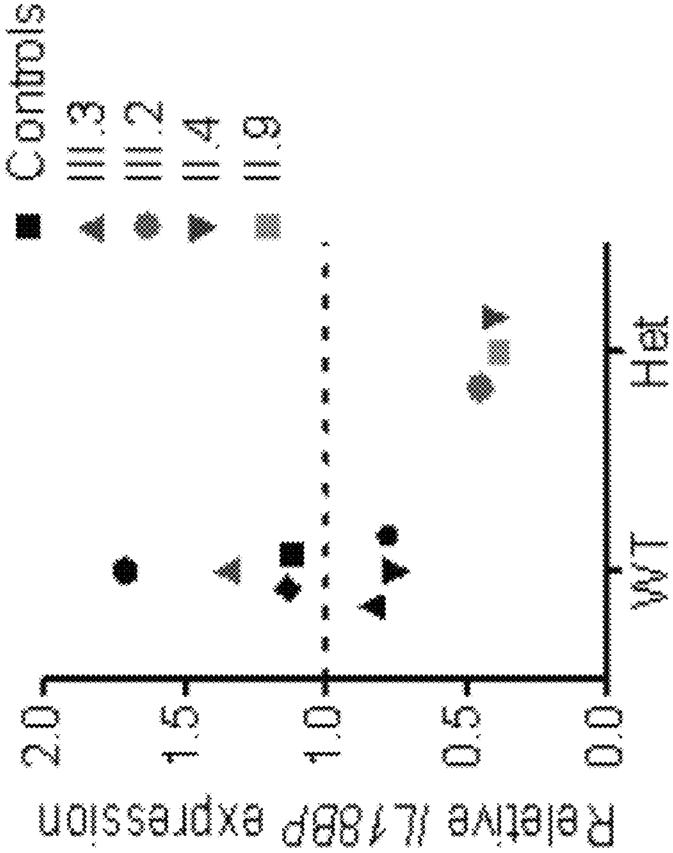
Figure 2C:
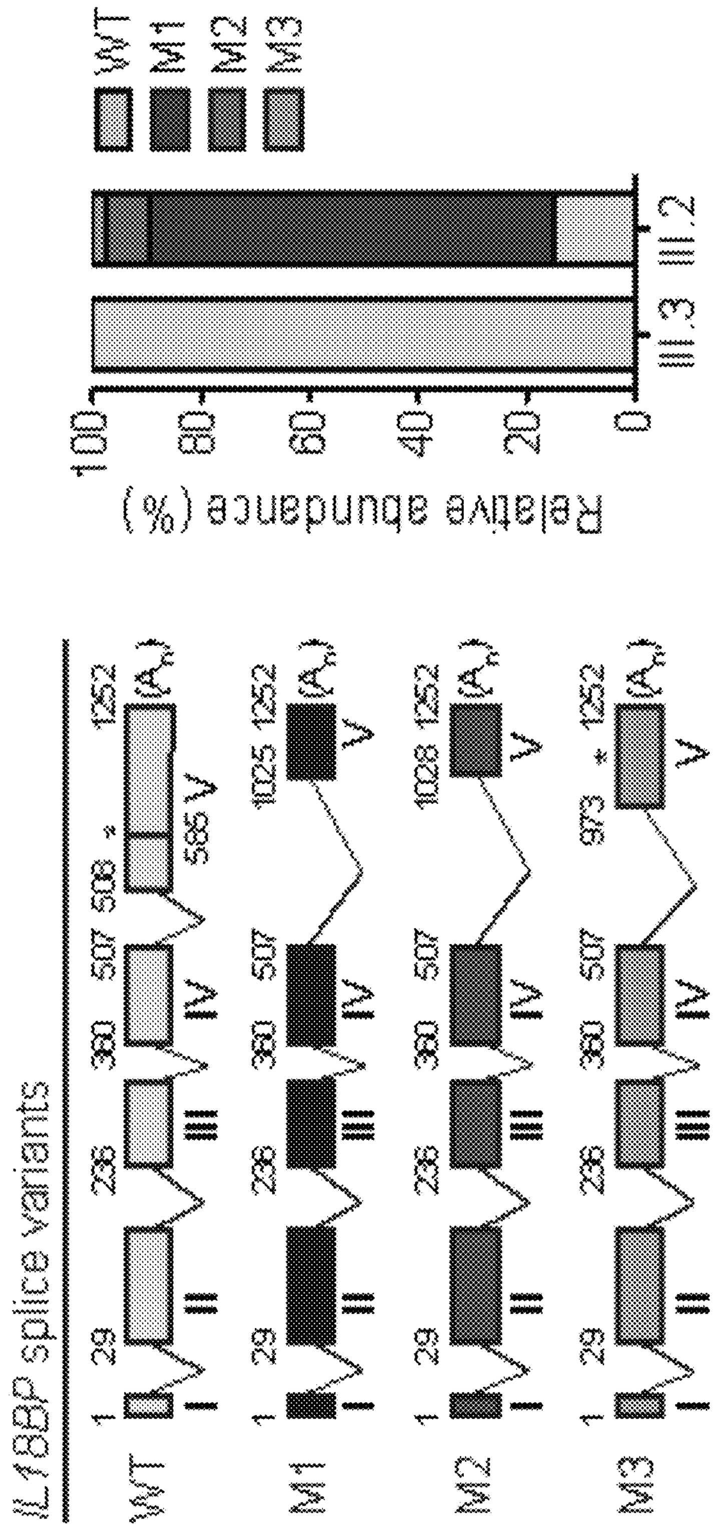
Figure 2G:
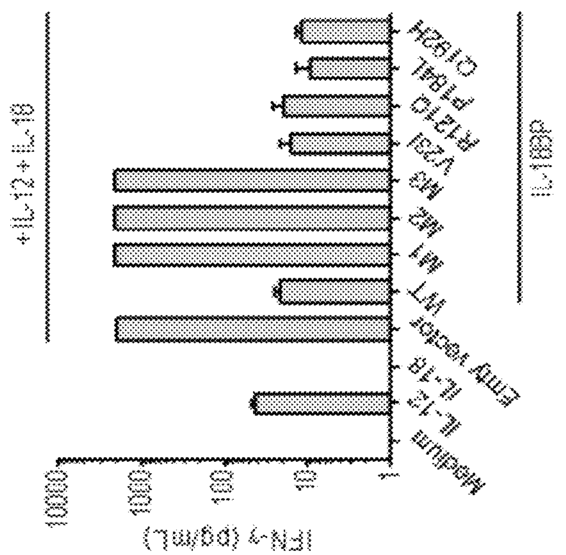
Figure 2F:
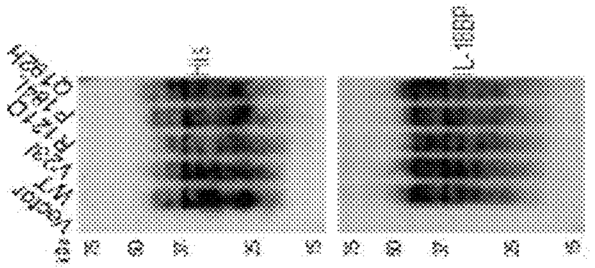
Figure 2E:
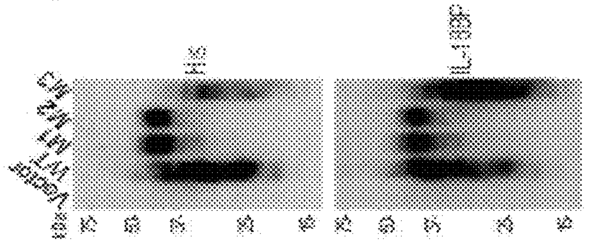
Figure 2D:
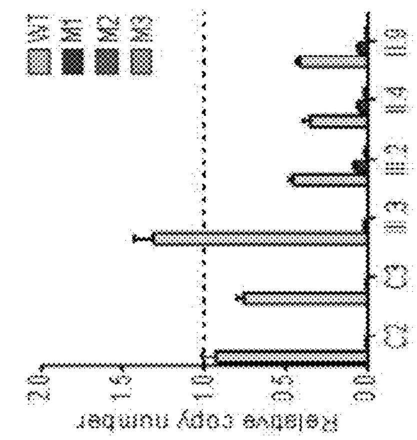
Figure 5A:
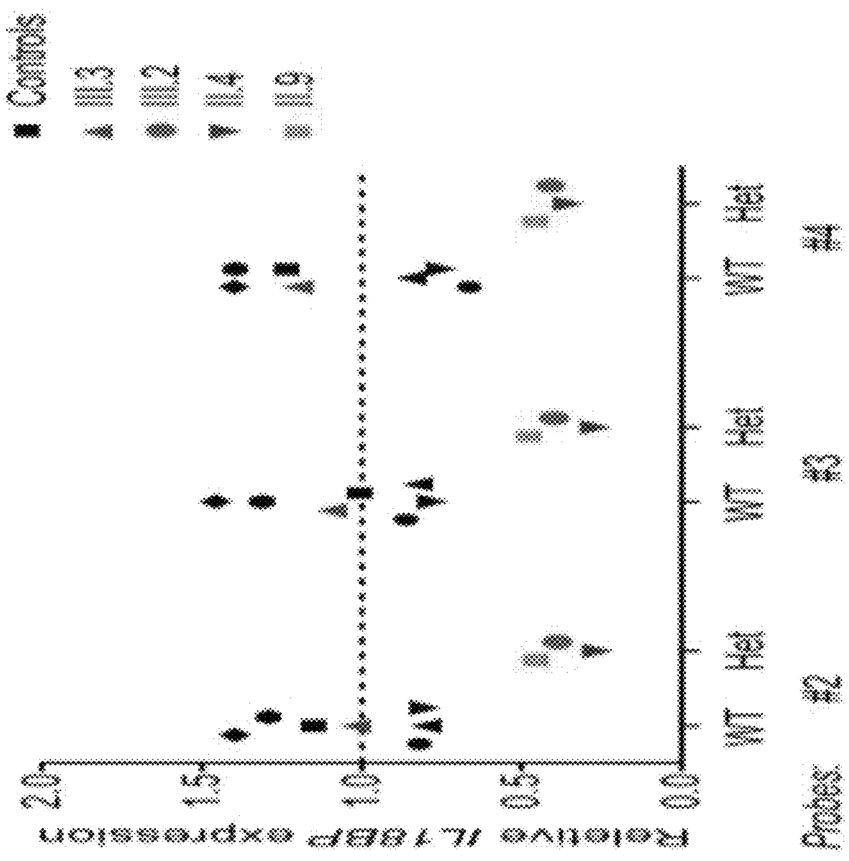
FIG. 5A to FIG. 5K. Impact of IL18BP.c.508-19_528del on gene expression and function. A. RT-qPCR showing the level of IL18BP expression, assessed with various probes (Materials and Methods) and normalized against endogenous GAPDH, in EBV-B cell lines from six healthy controls (black), the WT brother (III.3, purple), and heterozygous family members: brother (III.2, red), father (II.4, blue) and mother (II.9, green). Relative IL18BP expression was determined by normalization against the mean value for WT cells, which was set to 1 (indicated by a dashed line). The values shown are the means of two independent experiments performed in duplicate. B-C. Diagrams showing the design for 3'RACE on IL18BP performed on EBV-B cell lines (B) or on COS7 cells (C) using the pTAG4 3' exon-trapping vector. Numbers on the canonical IL18BP transcript begin with the start codon at position 1 and end with the polyadenylation site (indicated by ($A_n$)) at position 1252. D. Agarose gel electrophoresis, showing aberrant splicing of IL18BP mRNA in 3' RACE on COS7 cells transfected with pTAG4 vectors carrying the WT or mutant IL18BP allele. HPRT1 was used as the housekeeping gene control. E. The nested PCR products from FIG. S1D were cloned and colonies were sequenced. Diagram (left) and percentages (right) of WT (gray) and mutant (M1 in blue, M2 in red and M3 in green) splice variants are shown. Clones with PCR artifacts or sequences that do not match with canonical IL18BP transcript were excluded from analyses. F-G. Expression of WT and mutant IL-18BP isoforms: (M1-M3) in (F) and four missense variants (p.V23I, p.R121Q, p.P184L, and p.Q192H) from GnomAD in (G) was assessed in the concentrated supernatants from transiently transfected COS7 cells with either empty vector or constructs expressing indicated IL-18BP variants. Immunoblotting was performed with the His tag antibody (top). The membrane was then stripped and probed with the IL-18BP antibody (bottom). The concentrated supernatants were used in the IL-18BP bioassay experiments shown in FIG. 2F. H. IL-18BP bioassay: IFN-γ production was measured in NK-92 cells upon stimulation with recombinant human IL-12 (100 μg/mL), IL-18 (10 ng/mL) and/or IL-18BP at varying concentrations (125-500 ng/mL). Graph is presented on a logarithmic scale with base of 10. The data shown are means±SEM of 2 independent experiments performed in duplicate. I-J. Expression of the mutant IL-18BP isoforms (M1-M3) carrying the common missense variant (p.R121Q) was assessed in the concentrated supernatants from transiently transfected COS7 cells with either empty vector or constructs expressing indicated IL-18BP variants. Two independent preparations are shown (I4). Immunoblotting was performed with the His tag antibody (top). The membrane was then stripped and probed with the IL-18BP antibody (bottom). K. IL-18BP bioassay: IFN-γ production was measured in NK-92 cells after stimulation with recombinant human IL-12 (100 pg/mL), IL-18 (10 ng/mL) and/or concentrated supernatants (100 μg/mL of total protein) of COS7 cells transiently transfected with either empty vector or the constructs expressing indicated IL-18BP variants. Graph is presented on a logarithmic scale with base of 10. The data shown are means±SEM of 2 independent experiments performed in duplicate using the supernatants shown in FIGS. S1I-J.
Figure 5C:
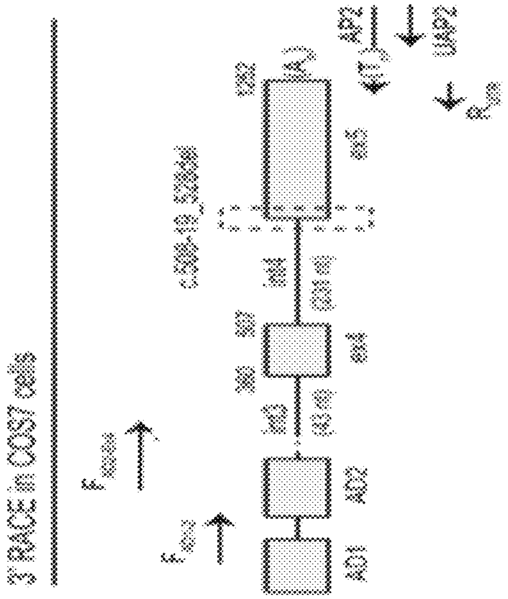
Figure 5B:
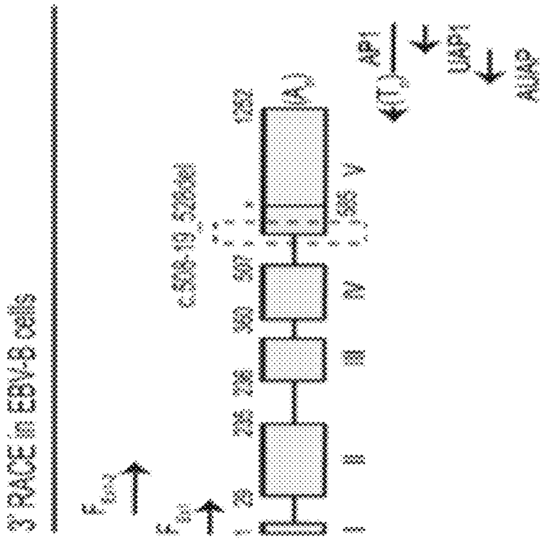
Figure 5E:
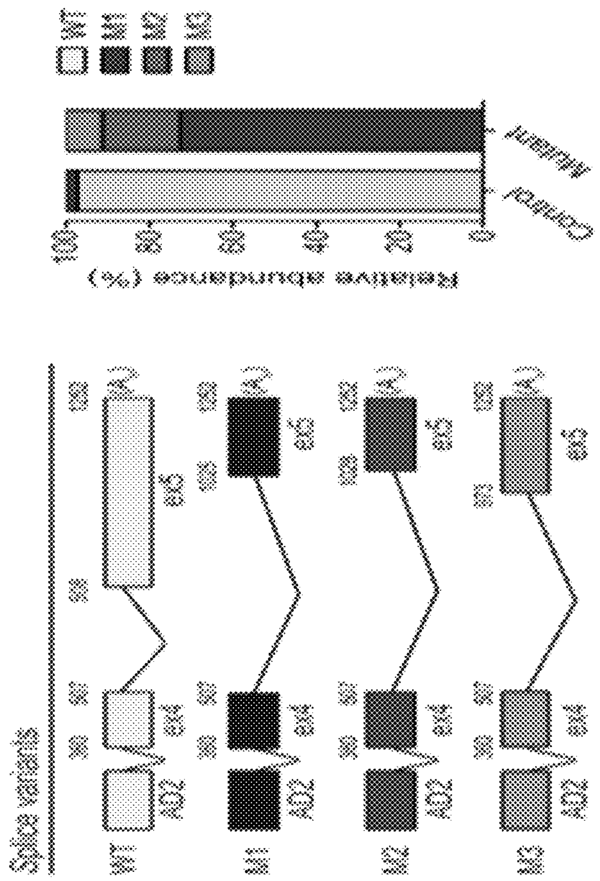
Figure 5D:
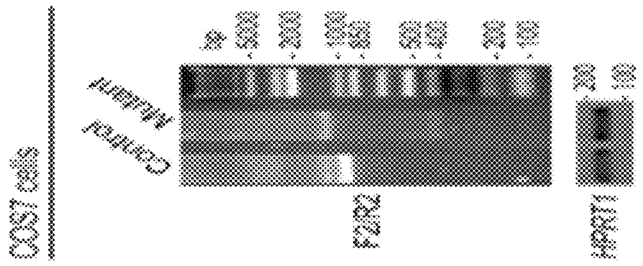

The canonical IL18BP transcript (NM_173042) contains five exons in total, encoding a protein of 194 amino acids (aa), also annotated as IL-18BPa, with an N-terminal signal peptide (1-30 aa) and an Ig-like domain (31-166 aa) responsible for binding to IL-18 (FIG. 1D). The c.508-19_528del mutation, which encompasses the last 19 nt of intron 4 and the first 21 nt of exon 5 (encoding aa 170 to 194), is predicted to impair the splicing of the last exon, thereby affecting the Ig-like domain and the C-terminal part of IL-18BP (FIG. 1D). We investigated the impact of this deletion on IL18BP expression in available material from the patient and other family members. Leukocyte gDNA and liver tissue sections were the only materials available for the deceased patient. We found that IL18BP mRNA levels in heterozygous EBV-B cells from a sibling and both parents were about 50% lower than those in homozygous wild-type (WT) cells from another sibling and healthy controls, in qPCR analyses with different probes detecting various IL-18BPa transcript variants (FIGS. 2A and 5A). This suggested that c.508-19_528del was loss-of-expression at the mRNA level. We then amplified the 3' end of the IL18BP cDNA, to determine whether the c.508-19_528del allele generated novel splice variants in the EBV-B cells of the heterozygous sibling (FIGS. 2B and 5B). We detected three new polyadenylated transcript variants (M1-M3) that also carried the cis p.R121Q mutation (FIG. 2C). We confirmed these findings through the transient expression of IL18BP exons with a 3' terminal exon-trapping vector (pTAG4) in COS7 cells (FIGS. 5C-E). In particular, M1 and M2 seemed to have no stop codons before the polyadenylation (poly-A) site. However, qPCR on EBV-B cells from WT controls and heterozygous family members showed that all mutant variants were barely detectable, and present in much smaller amounts than the WT form (FIG. 2D). These findings confirmed that c.508-19_528del results in a skipping of the initial sequences of exon 5, without leakiness, and the generation of three novel IL18BP transcripts with a shorter terminal exon. Two of these new transcripts have no stop codon, and all three are rapidly degraded. These data suggest that the patient had AR complete IL-18BP deficiency.

Mutation c.508-19_528Del Disrupts IL-18BP Function

Figure 5H:
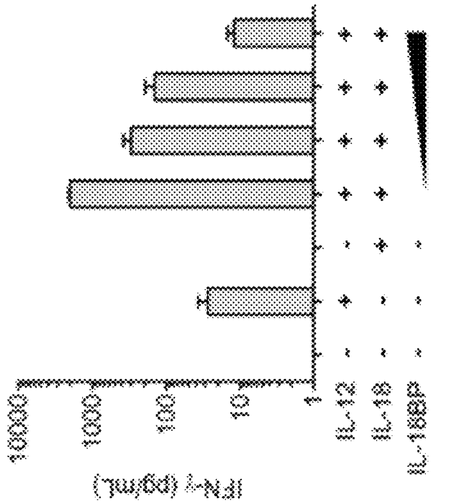
Figure 5G:
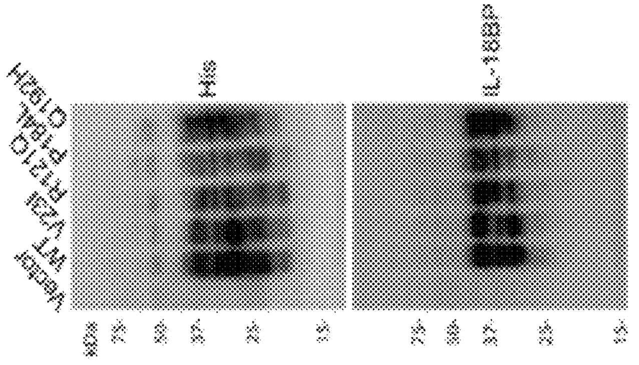
Figure 5F:
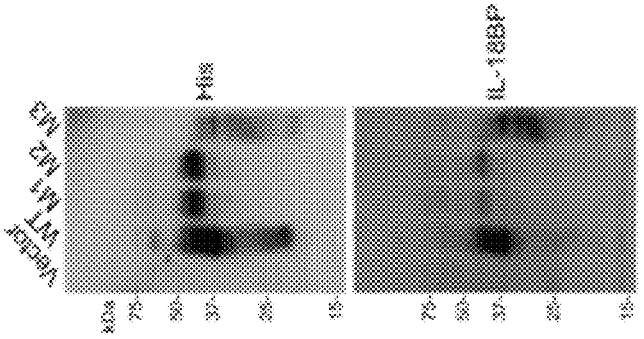
Figure 5K:
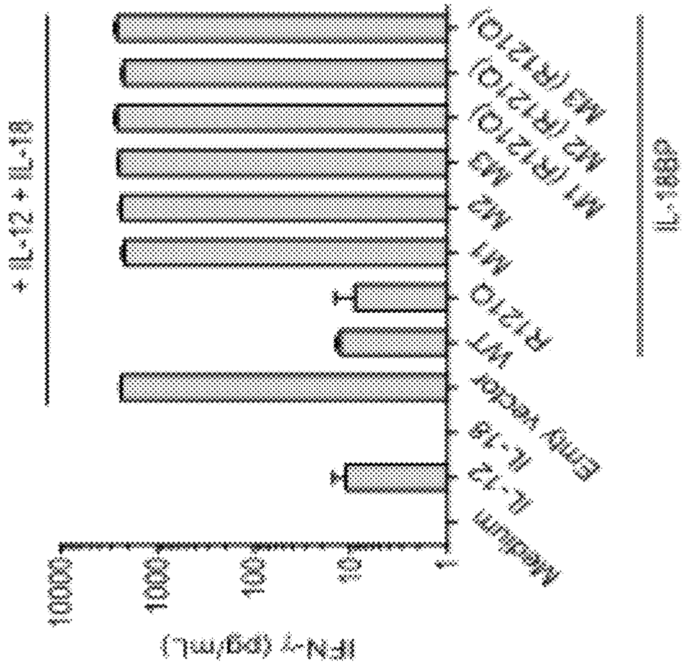
Figure 5J:
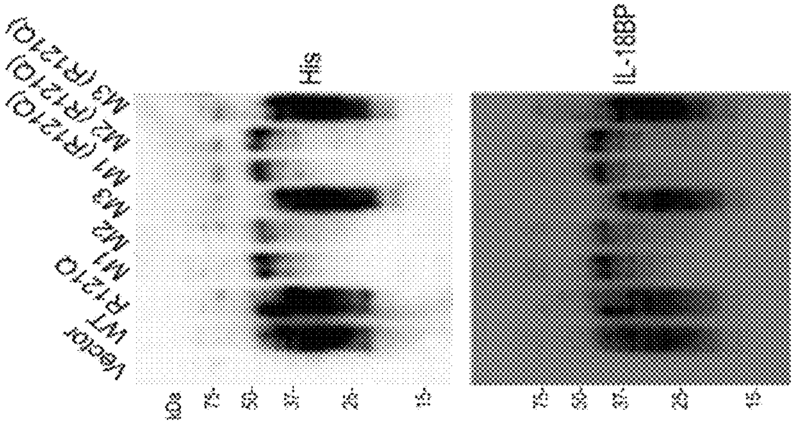
Figure 5I:
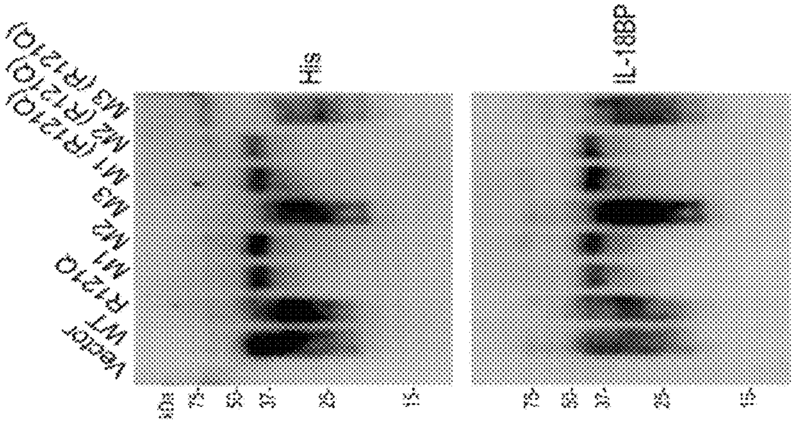

We generated cDNA constructs for expression of the three IL18BP variants (M1-M3) to assess their impact on IL-18BP expression and function in vitro. Human IL-18BP migrates at 25-45 kDa on SDS-PAGE gels in reducing conditions, due to heterogeneous glycosylation (Kim et al., 2000) (FIG. 2E). We detected the abnormal expression of the mutant isoforms (M1-M3) in transiently transfected COS7 cells. The M1 and M2 migrated at about 45 kDa, displaying more consistent glycosylation than for the WT, whereas M3 had a lower molecular weight but a similar glycosylation pattern to the WT (FIGS. 2E and 5F). We then analyzed protein production from the four non-synonymous IL18BP alleles found in the homozygous state in GnomAD (the common variants p.R121Q and p.Q192H, and the rare variants p.V23I and p.P184L). The pattern of expression of these variants with a C-terminal 6x-His tag in COS7 cells was similar to that of the WT (FIGS. 2F and 5G). We investigated the functional impact of all variants by an in vitro IL-18BP bioassay in which human IL-18BP inhibits the IL-12/IL-18-induced production of IFN-γ by the natural killer (NK)-92 cell line (Kim et al., 2000) (FIG. 5H). We compared the activity of WT and mutant IL-18BP obtained from the concentrated supernatants of COS7 cells transfected with empty vector, WT, or mutant (M1-M3) IL-18BP constructs. All four missense proteins had normal IL-18-inhibiting activity, whereas M1, M2, and M3 did not block IL-18 activity at all (FIG. 2G). Similar results were obtained for the mutant constructs (M1-M3) generated with or without the common missense allele (p.R121Q) carried by the patient (FIG. 5I-K). Overall, the c.508-19_528del allele encodes barely detectable M1, M2 and M3 isoforms, all of which lack IL-18-neutralizing function probably due to their altered protein expression, in terms of pattern and molecular weight. These findings indicate that the patient had AR complete IL-18BP deficiency, whereas individuals from the general population carrying homozygous IL18BP variants had normal IL-18BP expression and function. These findings suggest that AR IL-18BP deficiency is exceedingly rare in the general population and that AR IL-18BP deficiency is probably the cause of FVH in this patient.

Expression Patterns of IL18, IL-18BP, and IL-18R in the Liver

Figures 6A, 6B, 6C:
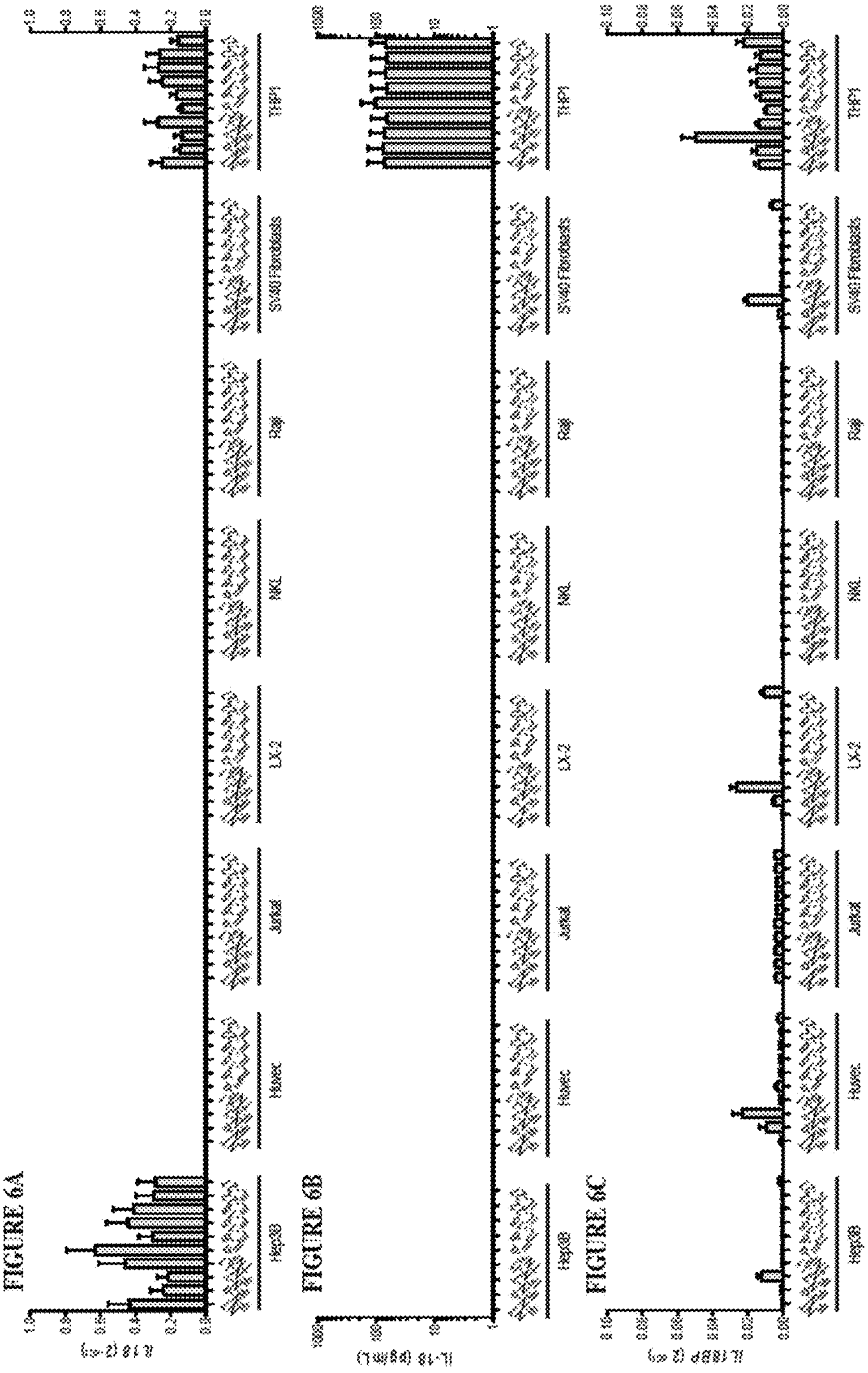
FIG. 6A to FIG. 6F. Expression patterns of IL-18, IL-18BP, and IL-18R in various human cell lines. RT-qPCR was used to determine relative mRNA levels ($2^{-dCt}$) of IL18, IL18BP, IL8R1, and IL18RAP normalized against endogenous GAPDH levels in different human cell lines following stimulation with various inflammatory cytokines for 6 h. The secretion of IL-18 and IL-18BP was assessed by ELISA at 24 h post-stimulation with various inflammatory cytokines. A-B. Relative expression levels for IL18 mRNA (A) and IL-18 protein (B) are shown. C-D. Relative expression levels for IL18BP mRNA (C) and IL-18BP protein (D) are shown. E-F. Relative expression levels for IL18R1 mRNA (E) and IL18RAP mRNA (F) are shown.
Figures 6D, 6E, 6F:
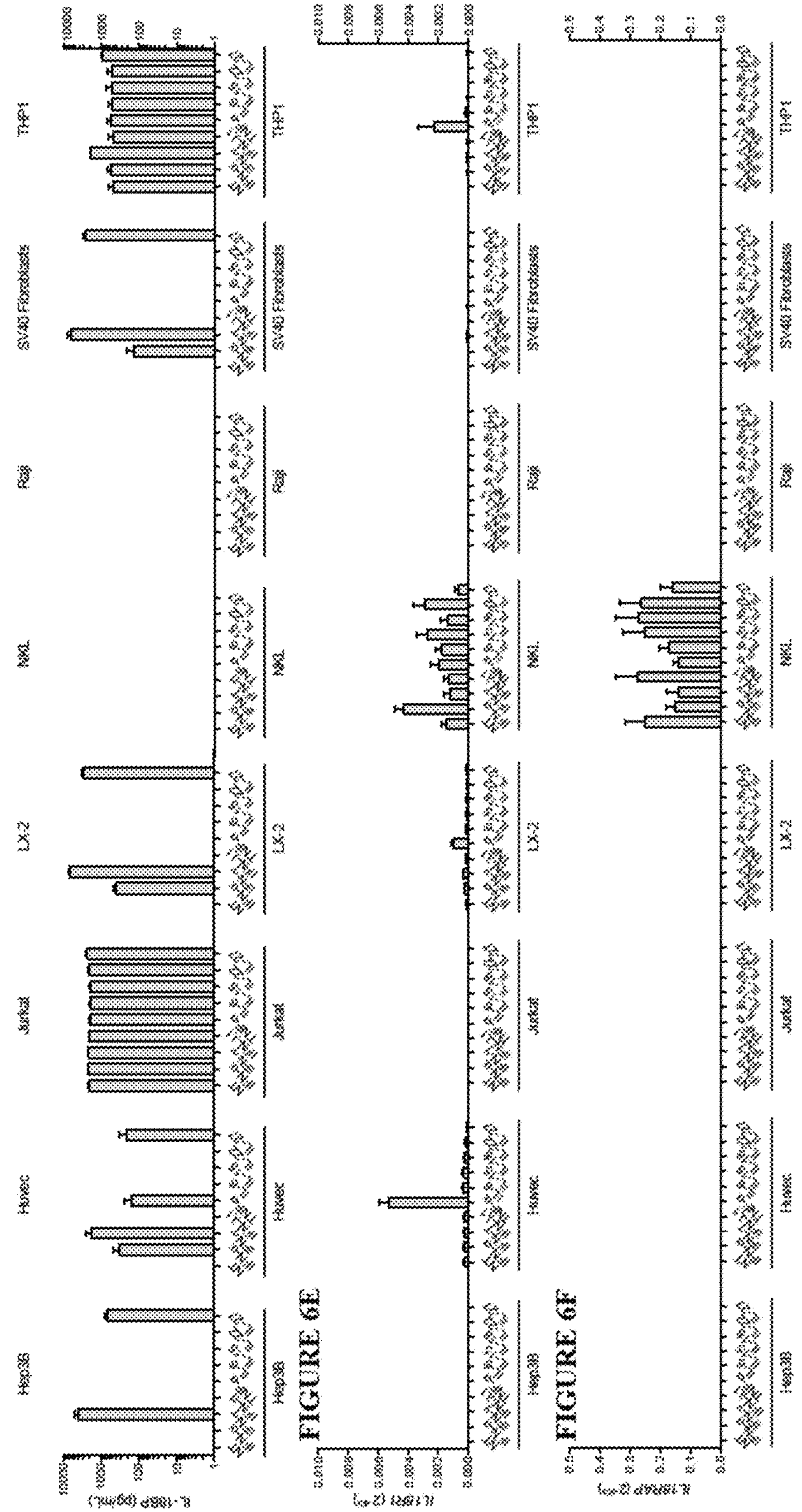
Figure 7:
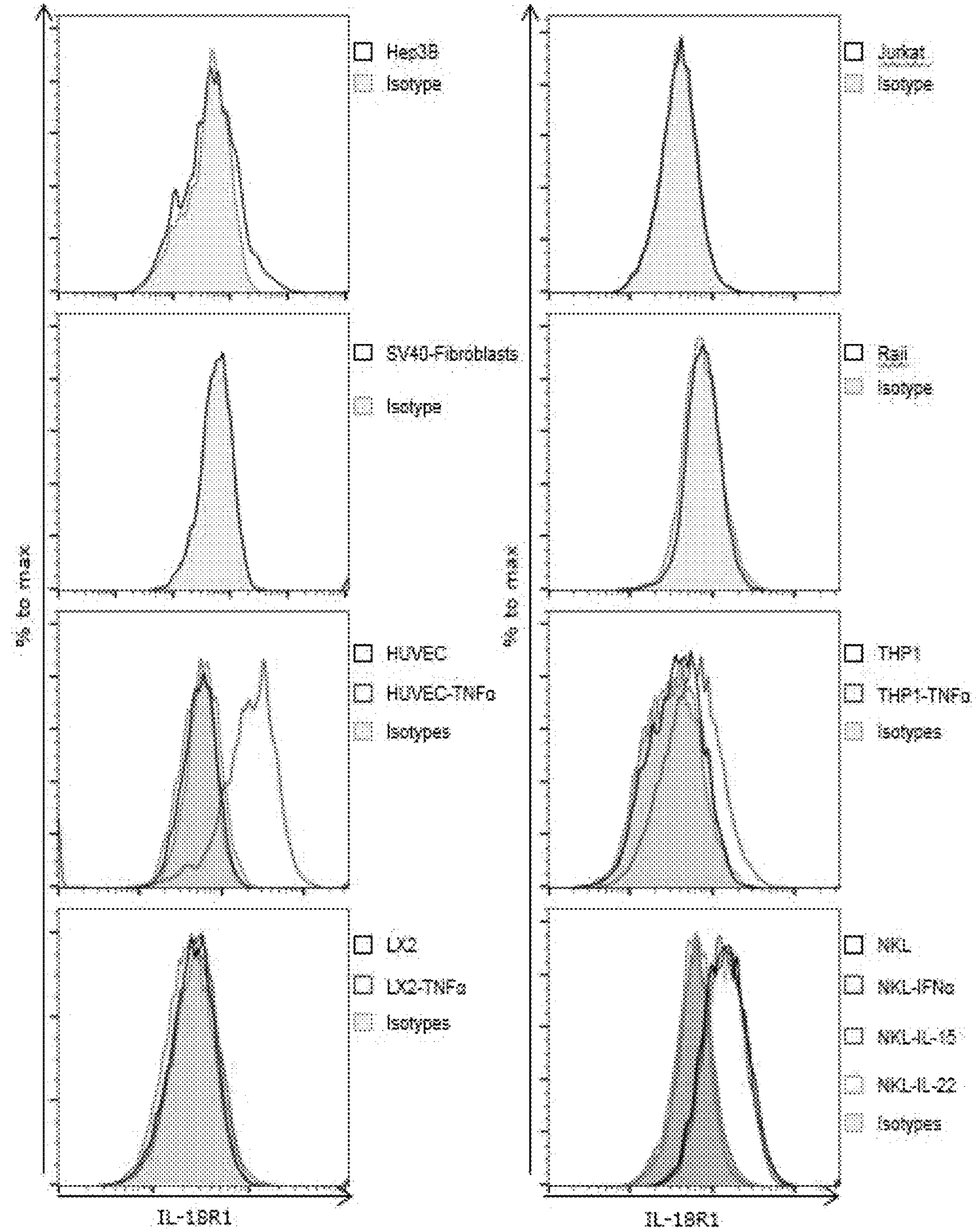
FIG. 7. Surface expression of IL-18R1 in various human cell lines. Surface expression levels of IL-18R1 were assessed by flow cytometry on different human cell lines following stimulation with indicated inflammatory cytokines for 24 h.

Human IL-18 was initially identified from a liver cDNA library as an IFN-γ-inducing factor in NK cells and T cells (Ushio et al., 1996). We analyzed the expression patterns of IL-18, IL-18BP, and the two chains of the IL-18 receptor (IL-18R), IL-181R and IL-18RAP, in several human cell lines acting as surrogates of liver-resident cells: Hep3B (hepatocytes), HUVEC (endothelial cells), LX-2 (hepatic stellate cells), SV40-fibroblasts, THP1 (monocytes), NKL (NK cells), Jurkat (T cells) and Raji (B cells) cells. We assessed mRNA and protein levels at baseline and following stimulation with various inflammatory cytokines, including IFN-αt, IFN-γ, IFN-λ, TNF-α, IL-6, IL-15, IL-18, IL-22, and IL-27 (FIGS. 6 and 7). We found that THP1 cells were major producers of IL-18, whereas IL-18 was either present at very low levels or undetectable in other cell types (FIG. 6A-B). IL-18BP was constitutively expressed only in THP1 and Jurkat cells, and was markedly upregulated by stimulation with IFN-γ particularly in Hep3B, SV40-fibroblasts, HUVEC, and LX2 cells (FIG. 6C-D). Moreover, IFN-α or IL-27 also increased IL-18BP production, albeit to a much lesser extent (FIG. 6C-D). Of note, we did not detect rare alternative splicing forms of IL18BP, namely IL18BPb, IL18BPc, and IL18BPd (Kim et al., 2000; Novick et al., 1999), in HepG2 (hepatocyte) cells, THP1 cells, or primary human hepatocytes, as previously reported to be absent in human peripheral mononuclear blood cells (PBMCs) (Veenstra et al., 2002) (data not shown). Finally, we found that both chains of IL-18R were expressed principally in NKL cells. (FIGS. 6E-F and 7). These observations, consistent with previous reports (Lebel-Binay et al., 2000), suggest that IL-18 is mostly produced by macrophages in the liver, and that it induces IFN-γ production, particularly by NK cells, which in turn triggers intrahepatic IL-18BP secretion, mostly from hepatocytes and macrophages. Thus, IL-18BP, which is induced strongly by IFN-γ, can buffer intrahepatic IL-18 activity through negative feedback.

Figure 3:
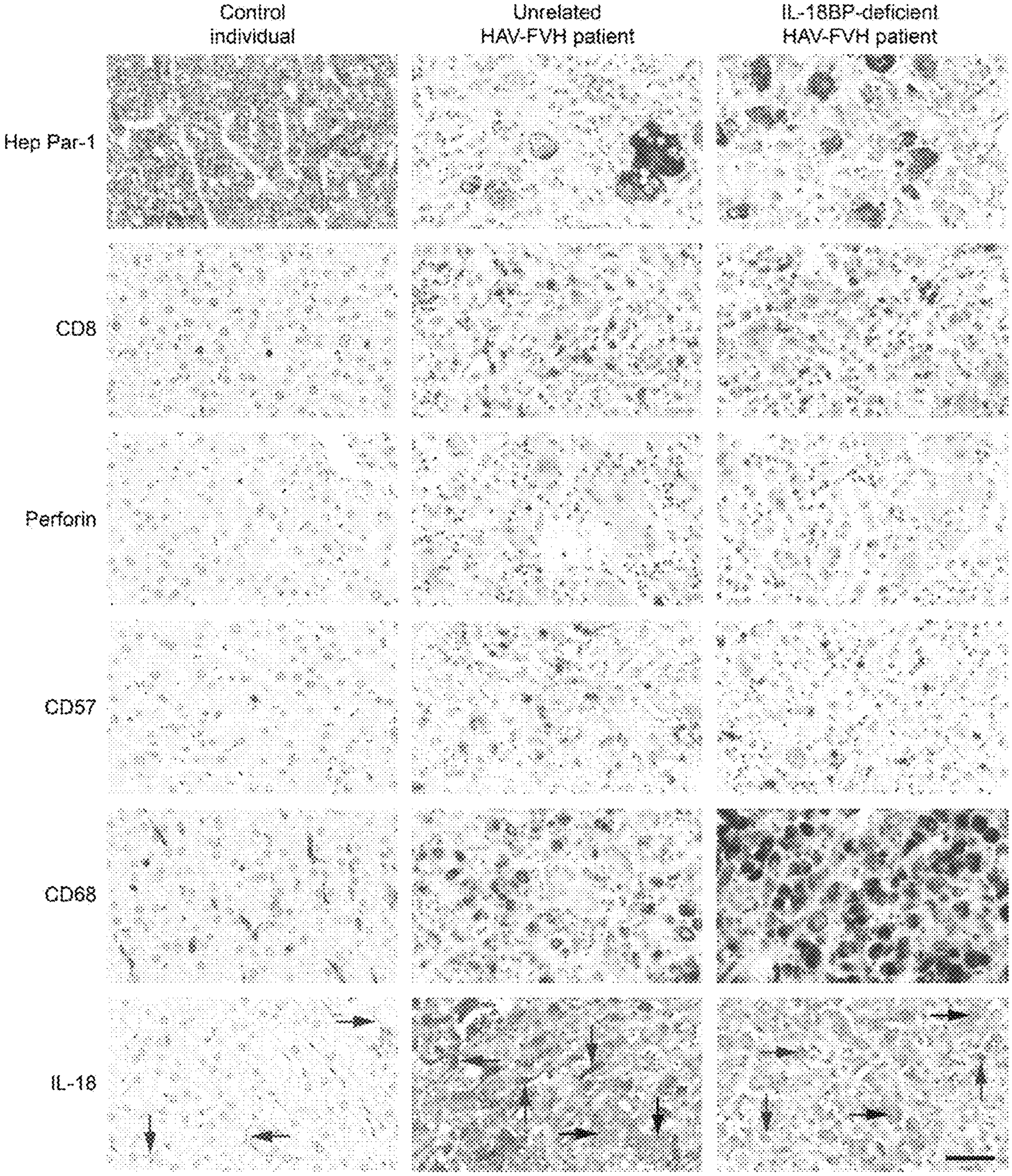
FIG. 3. Liver immunohistochemical profile of the patient. Liver tissue sections from a control individual, an unrelated patient with FVH due to HAV, and the deceased IL-18BP-deficient FVH patient reported in this study were subjected to immunohistochemical staining with the following markers: Hep Par-1, CD8, perforin, CD57, CD68, and IL-18. Representative zoom-in views of the original images at 400× magnification (Figure S4) are shown. Hep Par-1 staining of IL-18BP-deficient patient's liver tissue section displayed a background staining of macrophages, with lower intensity than hepatocytes. Some IL-18-positive hepatocytes and macrophages are indicated with blue and red arrows, respectively. Scale bar represents 50 μm.
Figure 8:
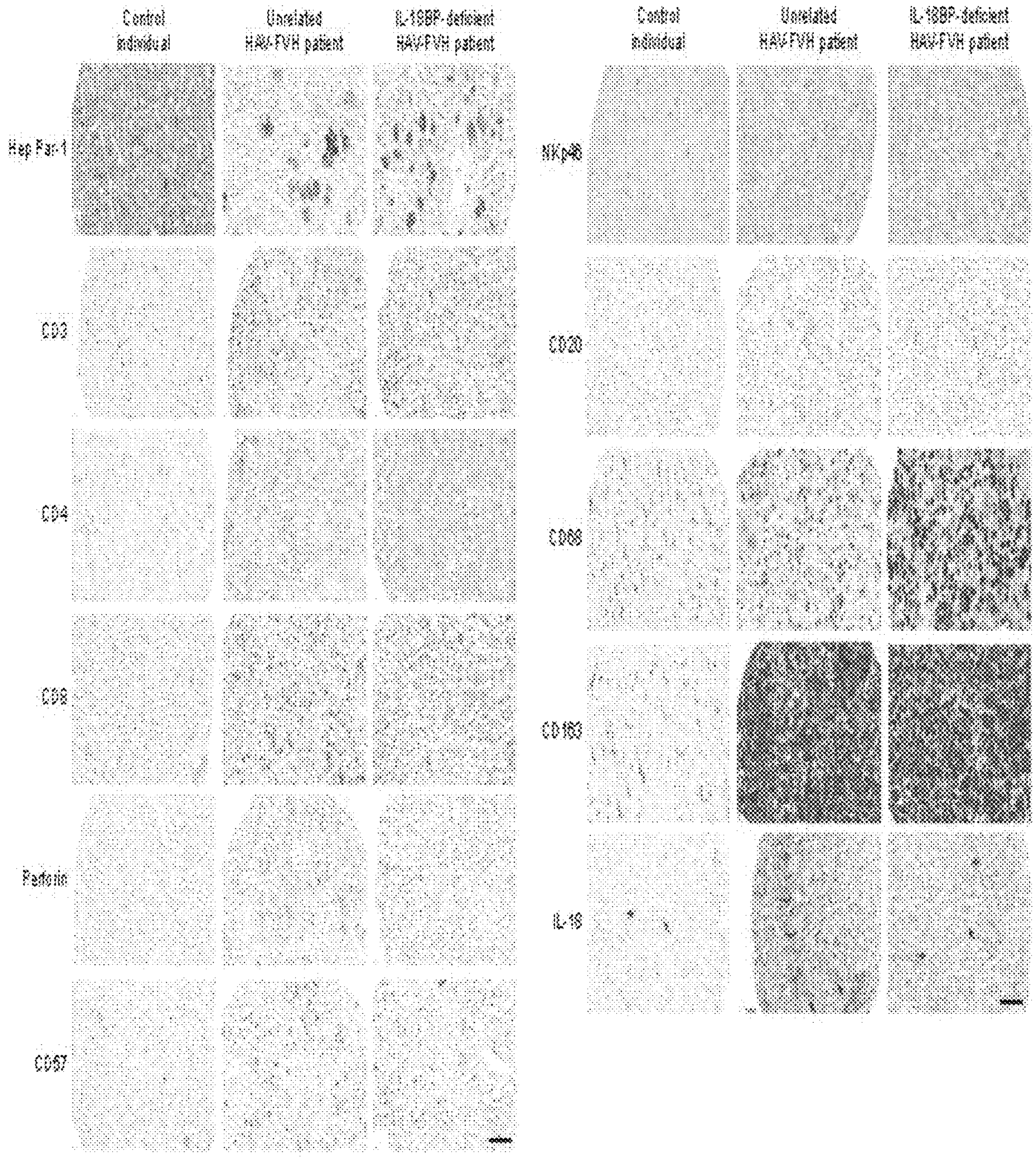
FIG. 8. Liver immunohistochemistry profile of patients with FVH. Immuhistochemistry staining of liver tissue sections from a control individual, an unrelated patient with FVH due to HAV, and the deceased IL-18BP-deficient FVH patient (reported in this study) with the following markers: Hep Par-1, CD3, CD4, CD8, Perforin, CD57, NKp46, CD20, CD68, CD163, and IL-18. Hep Par-1 staining of IL-18BP-deficient patient's liver tissue section displayed a background staining of macrophages, with lower intensity than hepatocytes. IL-18BP-deficient patient and the unrelated FVH patient displayed also some residual hepatocytes positive for CD163 staining. Some IL-18-positive hepatocytes and macrophages are indicated with blue and red arrows, respectively. All images are shown at 400× magnification. Scale bar represents 100 μm.

Elevated IL-18 Levels in Liver Tissues of Patients with Fulminant Viral Hepatitis It has been suggested that the liver lesions observed during the course of acute hepatitis are not directly due to the cytopathic effects of HAV, but instead result from excessive cytotoxic activity of NK, NKT, and $CD8^+$ T lymphocytes (Kim et al., 2011; Kim et al., 2018; Lemon et al., 2018). We thus performed immunohistochemical staining on liver sections from the IL-18BP-deficient patient described in this study, an unrelated patient with FVH due to HAV, and an individual without liver inflammation. Only very small numbers of hepatocytes were detected in the liver tissues of the two FVH patients (FIG. 3). However, the IL-18BP-deficient patient and the unrelated FVH patient had higher proportions of T cells ($CD3^+$, $CD4^+$, or $CD8^+$), perforin-positive cells (attributed to $CD8^+$ T and NK cells), NK cells ($CD57^+$ or $NKp46^+$), B cells ($CD20^+$), macrophages (M1 and M2; $CD68^+$) and M2 ($CD163^+$) macrophages than the control individual (FIG. 3 and FIG. 8). These observations indicate a massive loss of hepatocytes and inflammatory cell accumulation in the livers of FVH patients. Moreover, the IL-18 staining was abnormally high in the liver tissues of FVH patients. This cytokine was detected in both macrophages and hepatocytes in these patients, whereas it was barely detectable overall and found only in macrophages in healthy liver sections (FIG. 3 and FIG. 8). IL-18BP was not detected in liver sections from controls or patients (data not shown; Materials and Methods). Collectively, these data suggest that, in baseline conditions, IL-18 is produced mostly by macrophages in the liver, but that hepatocytes also produce IL-18 during viral infection.

Human IL-18 Induces NK Cell-Mediated Killing of Hepatocytes In Vitro

Figure 4A:
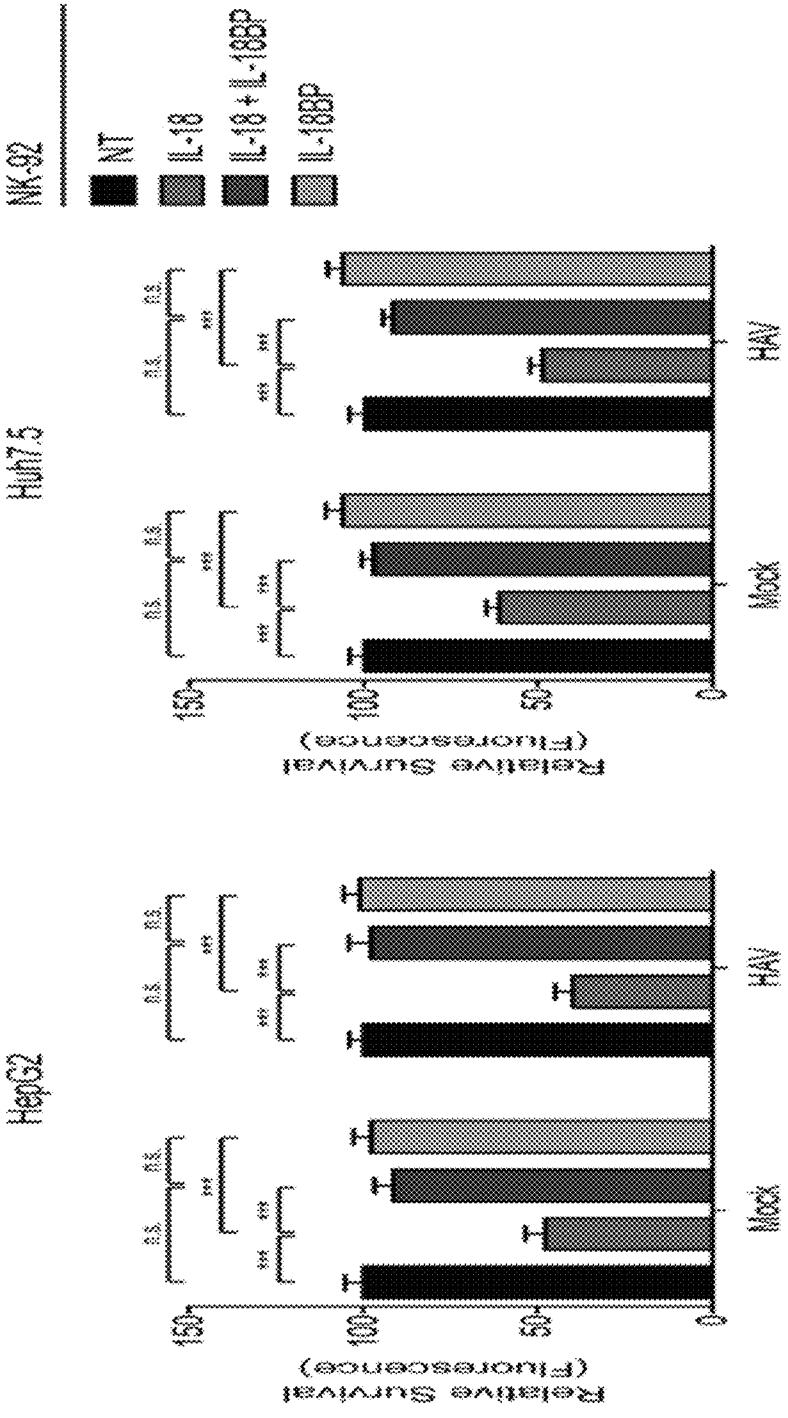
FIG. 4A to FIG. 4C. IL-18/IL-18BP-mediated hepatotoxicity. A-B Coculture of mock- or HAV-infected hepatocytes (HepG2 and Huh7.5 cells) with NK-92 cells pretreated with IL-18, IL-18+IL-18BP, or IL-18BP. HAV infection efficiencies in HepG2 and Huh7.5 cells were around 40% and 100%, respectively (FIG. S5E; Materials and Methods). The relative survival of calcein-AM-stained HepG2 or Huh7.5 cells was calculated based on the measurement of fluorescence retention within cells (A) and the amount of secreted albumin (B). Relative fluorescence and albumin levels were determined by normalization against the mean value for hepatocytes cocultured with NK92 cells without pretreatment (NT), set to 100. A decrease in the fluorescence or in albumin levels indicates an increase in NK cell-induced hepatotoxicity. The data shown are the means±SEM of 3 independent experiments performed in quadruplicate (n.s.=not significant, *P<0.05, P<0.01, *P<0.001; one-way ANOVA with Bonferroni correction for multiple comparisons). C. A proposed model for IL-18BP deficiency underlying fulminant viral hepatitis. During the course of acute HAV infection in an otherwise healthy individual (left panel), IL-18 is secreted by macrophages in the liver. This cytokine activates lymphocytes, such as NK cells, inducing IFN-γ production and cytotoxicity to eliminate HAV-infected cells. IFN-γ also induces IL-18BP secretion by hepatocytes, macrophages and other non-parenchymal cells (endothelial cells, fibroblasts, and hepatic stellate cells), to buffer IL-18 activity. However, in the absence of IL-18BP (right panel), excessive IL-18 activity leads to uncontrolled, massive immune-mediated hepatotoxicity and severe liver injury, as in the IL-18BP-deficient individual with fulminant viral hepatitis.
Figure 4B:
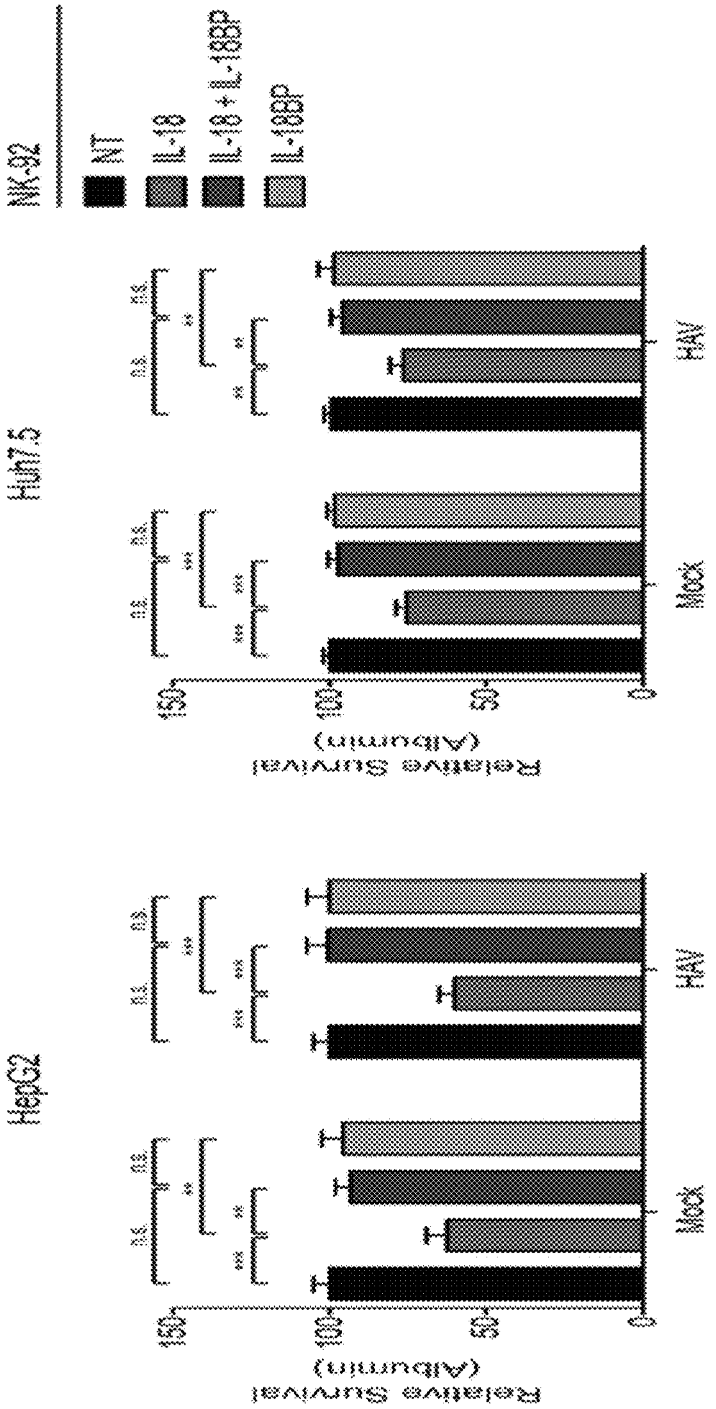
Figure 4C:
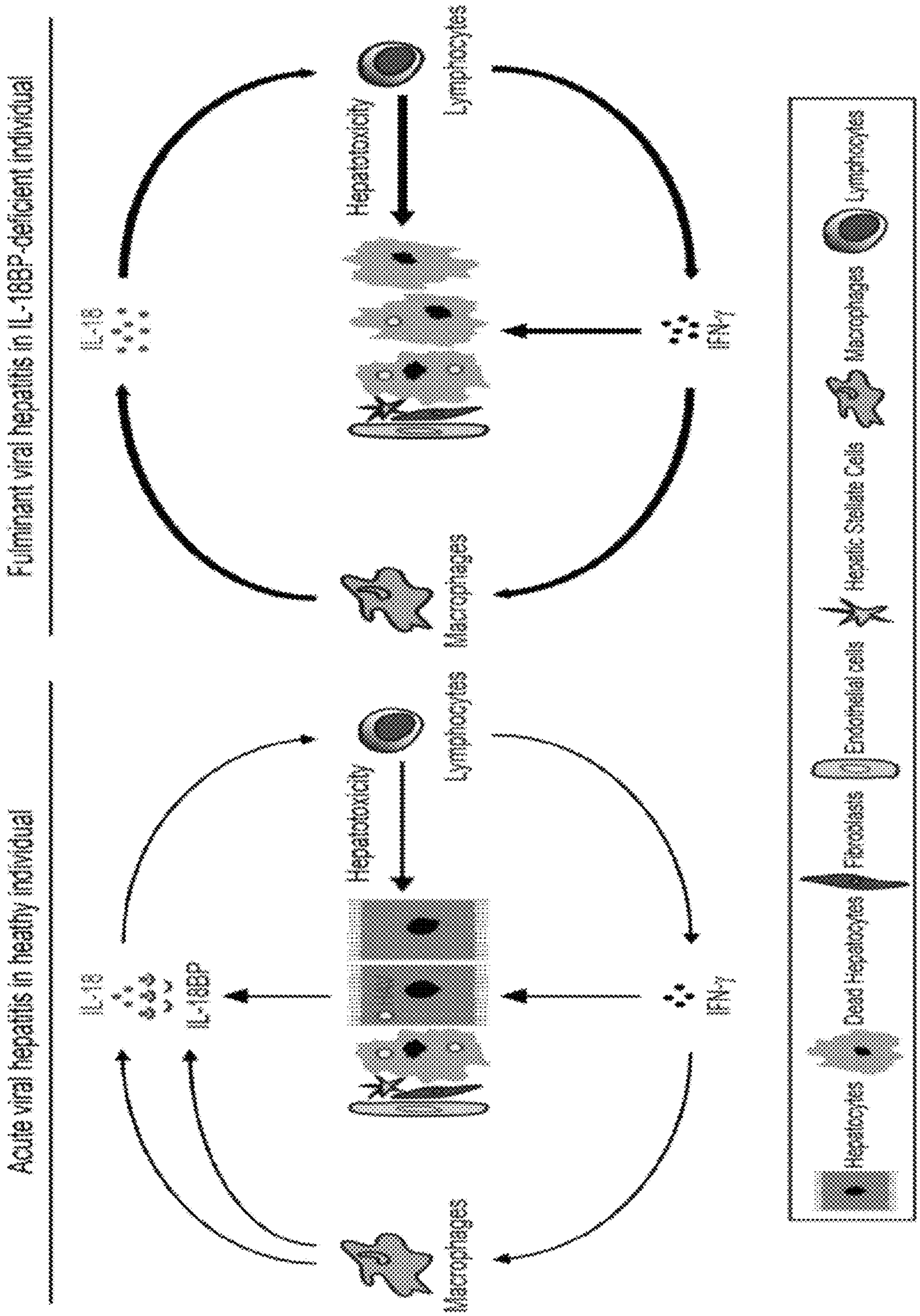
Figure 9A:
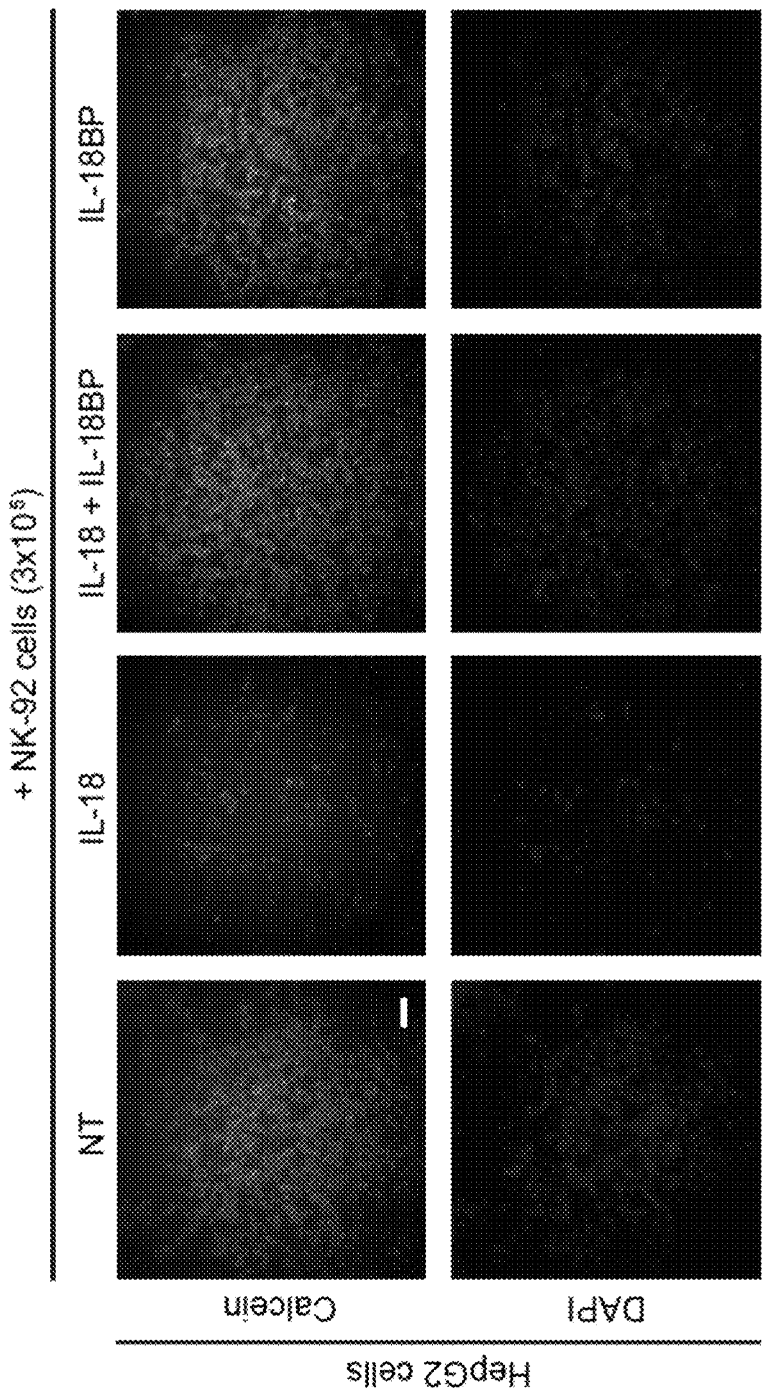
FIG. 9A to FIG. 9E. IL-18/IL-18BP-mediated hepatotoxicity. A-C. Coculture of HepG2 cells and NK-92 cells either with no pretreatment (NT) or pretreated with IL-18, IL-18+IL-18BP, or IL-18BP. A. Representative fluorescent images (4× magnification) are shown for IL-18/IL-18BP-mediated NK cell cytotoxicity against hepatocytes stained with Calcein-AM (green) and DAPI (blue). HepG2 cells were cultured with $3\times10^5$ NK cells per well. Scale bar represents 325 μm. B-C. IL-18/IL-18BP-mediated cytotoxicity against HepG2 cells shown for various numbers of NK-92 cells. The relative survival of HepG2 cells was calculated based on the measurement of fluorescence retention within cells (B) and the amount of secreted albumin (C). Relative fluorescence and albumin levels were determined by normalization against the mean value for HepG2 cells cocultured with NK92 cells without pretreatment (NT), set to 100. B-C. A decrease in the fluorescence or in albumin levels indicates an increase in NK cell-induced hepatotoxicity. Data are means±SEM of 3 independent experiments performed in quadruplicate for each group (n.s.=not significant, *P<0.05, P<0.01, *P<0.001; one-way ANOVA with Bonferroni correction for multiple testing). D. PBMCs isolated from two healthy individuals (Donor 1 and 2) were pretreated with IL-18 and/or IL-18BP in the presence of IL-2 for 24 h and cultured with calcein-AM-stained HepG2 cells for 4 h. Relative fluorescence levels were determined by normalization against the mean value for HepG2 cells cocultured with PBMCs without IL-2 treatment, which is set to 100. Data are means±SEM of 2 independent experiments performed in quadruplicate. E. Representative images show immunofluorescence staining for HAV infection in HepG2 and Huh7.5 cells at 20× magnification. Nucleus was stained with DAPI (blue). HAV-infected cells were in red. Scale bar represents 25 μm.
Figure 9B:
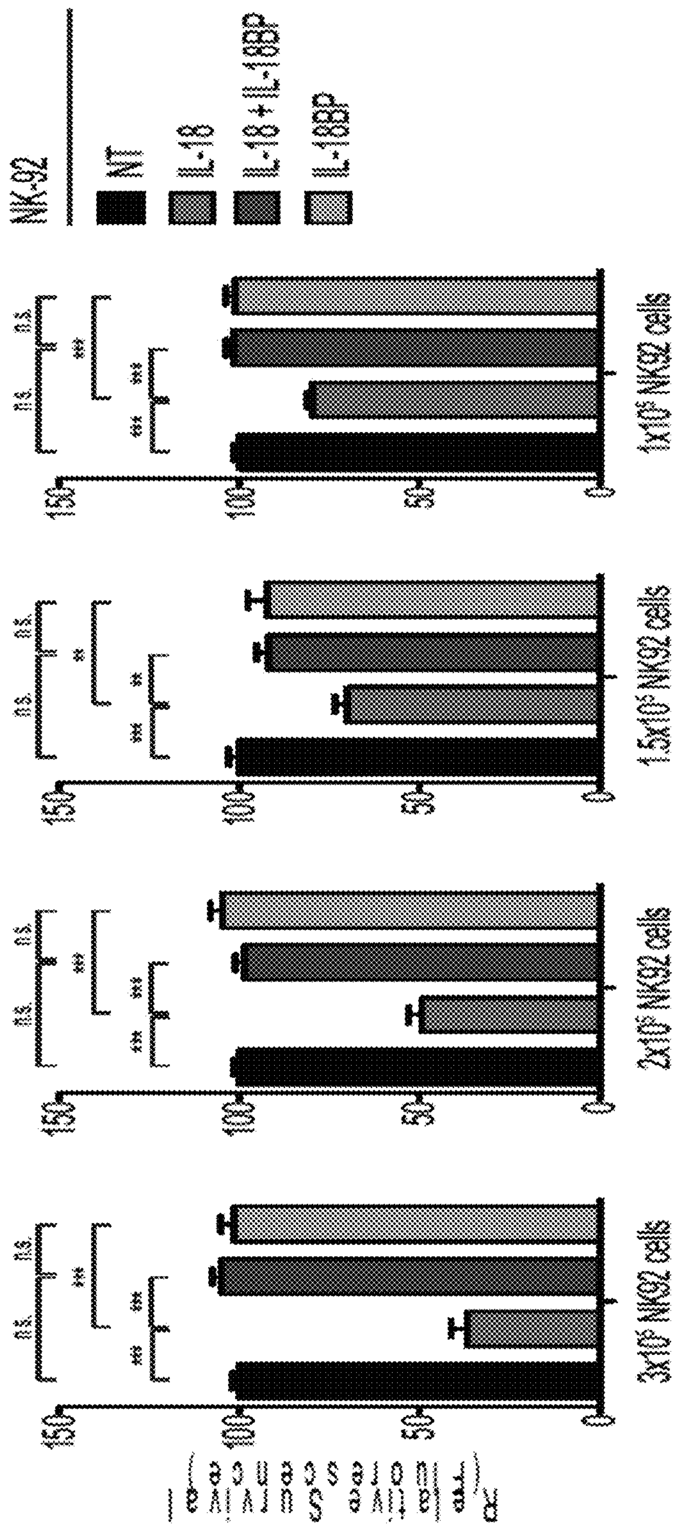
Figure 9C:
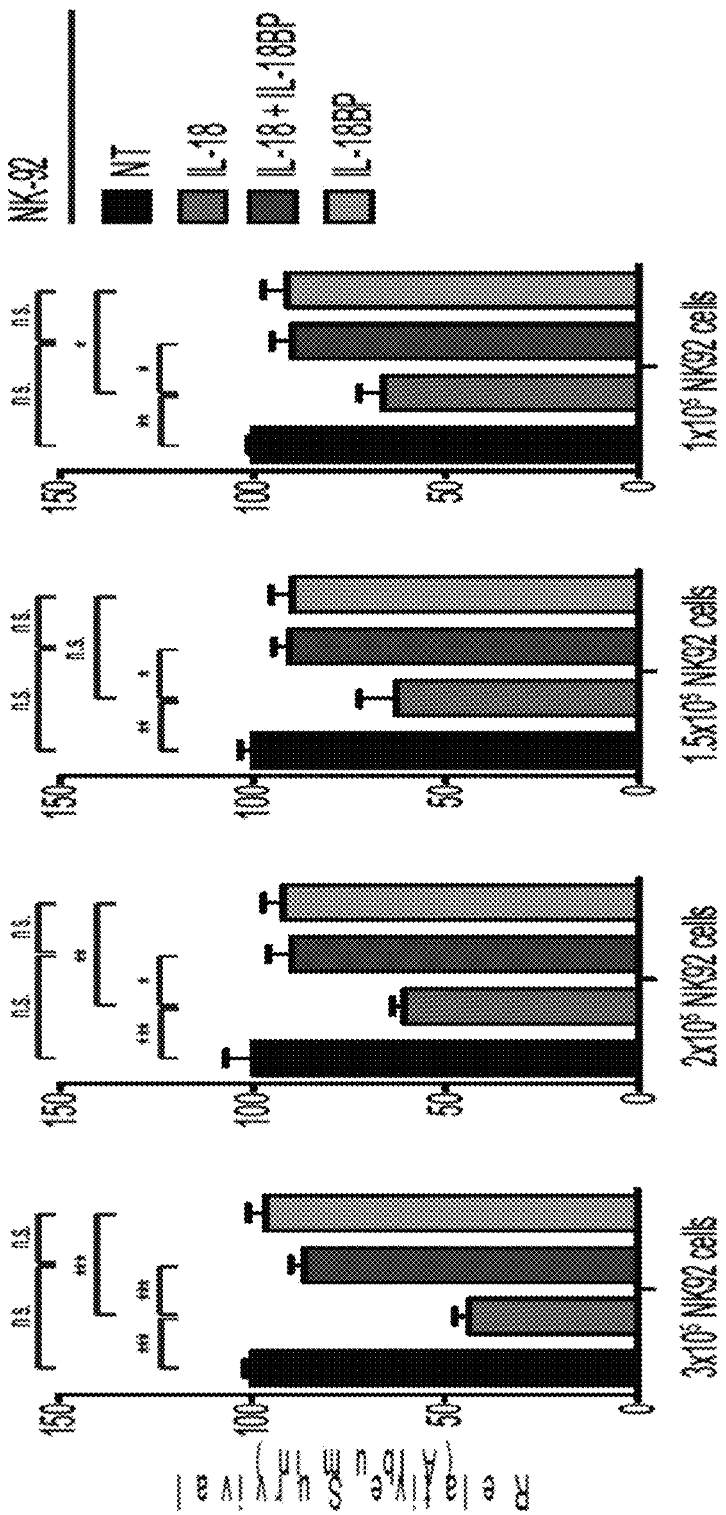
Figure 9E:
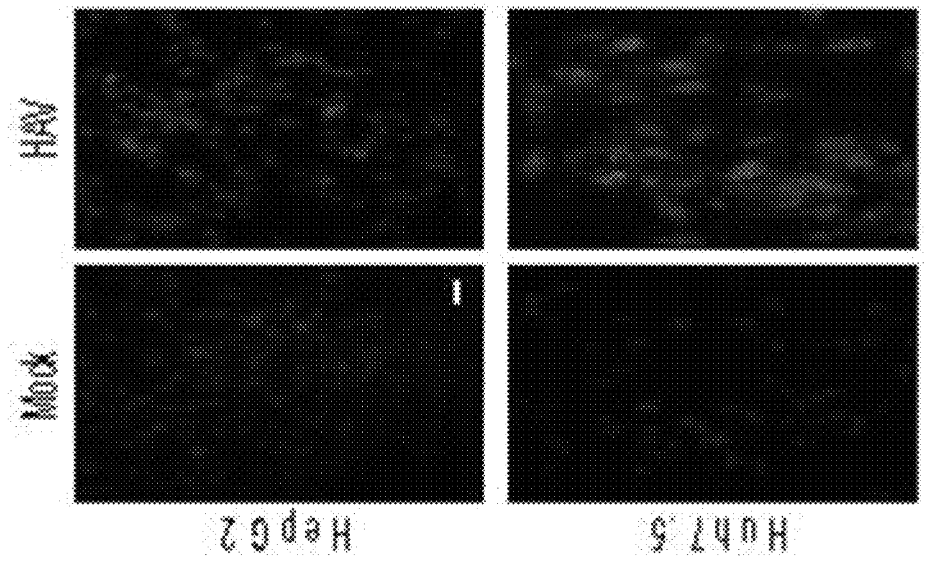
Figure 9D:
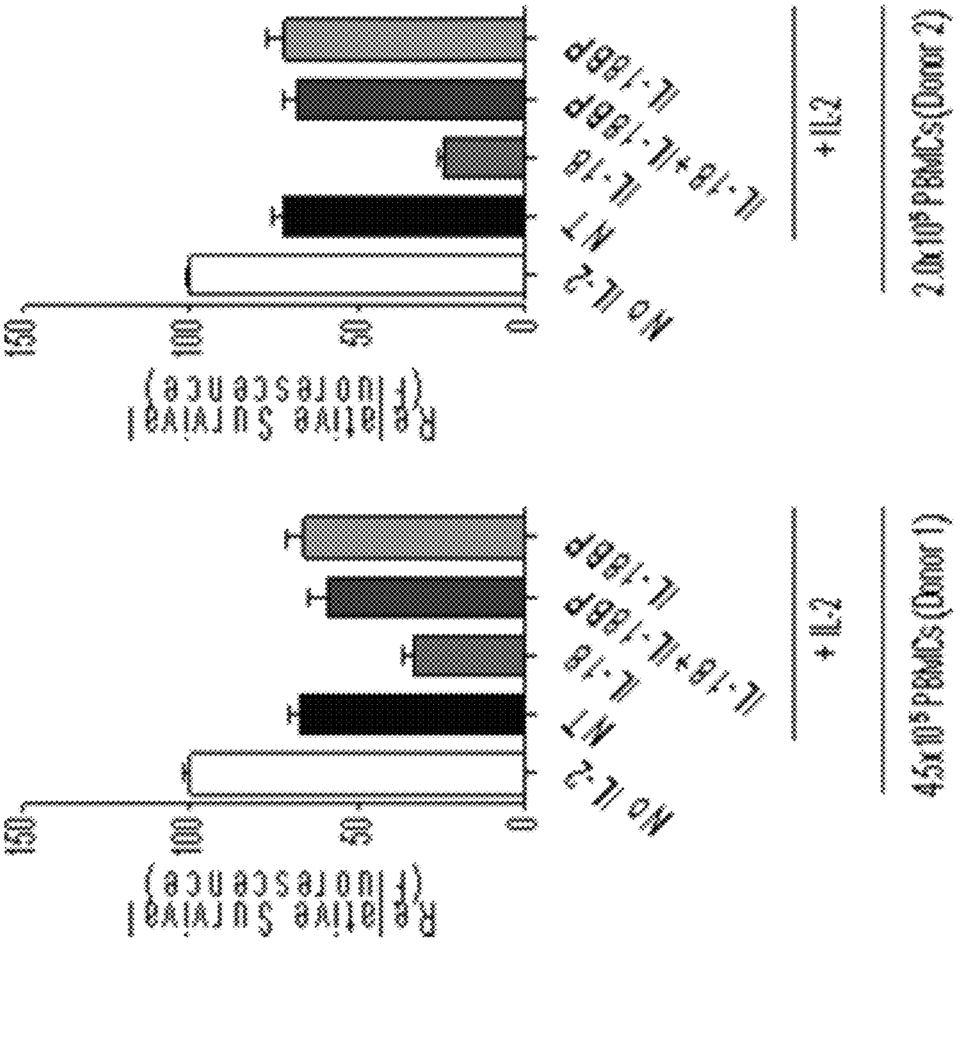

IL-18 increases NK and/or T cell-mediated cytotoxicity by inducing (i) the expression of membrane-bound FasL, an activator of cell death, (ii) the secretion of pro-apoptotic cytokines, such as TNF-α and TRAIL, and (iii) the secretion of cytolytic enzymes, such as perforin and granzyme (Kaplanski, 2018; Lebel-Binay et al., 2000; Tsutsui et al., 2000). Moreover, IL-18, together with IL-2, enhances the activation and in vitro cytotoxic activity of human peripheral NK cells (Nielsen et al., 2016; Son et al., 2001). IL-2-stimulated human liver NK cells have also been shown to be strongly cytotoxic, even more so than peripheral blood NK cells, to human HepG2 hepatocytes (Ishiyama et al., 2006). We therefore generated an in vitro model to test IL-18/IL-18BP-regulated hepatotoxicity through the coculture of HepG2 and NK-92 cells, which display a phenotype similar to liver-resident NK cells in humans (Le Bouteiller et al., 2002). NK cells activated with IL-18 killed significantly more hepatocytes than unstimulated NK cells, at various NK cell-to-hepatocyte ratios (FIG. 9A-C). As expected, IL-18BP completely rescued IL-18-induced NK cell-mediated hepatotoxicity (FIG. 9A-C). We also showed that IL-18, together with IL-2, increased in vitro cytotoxicity of PBMCs from healthy donors against HepG2 cells, and that IL-18BP could prevent the IL-18-induced toxicity (FIG. 9D). Finally, we infected HepG2 or Huh7.5 hepatocytes with HAV (FIG. 9E; Materials and Methods). We showed that IL-18-activated NK cells killed both infected and uninfected hepatocytes, and that this cytotoxicity was reversed by the addition of IL-18BP (FIG. 4A-B). Overall, these findings support a model in which the genetically determined absence of IL-18BP in the patient with FVH by HAV leads to uncontrolled IL-18-mediated cytotoxic activity against hepatocytes, involving NK and T cells, the most abundant lymphocytes in the liver, in particular, thereby exacerbating liver destruction (FIG. 4C).

DISCUSSION

We have established a causal relationship between AR complete IL-18BP deficiency and lethal FVH due to HAV in an 11-year-old child without preexisting liver disease and with no history of severe infection. Causality is established on both genetic and mechanistic grounds, meeting the criteria for genetic studies in single patients (Casanova et al., 2014). In contrast, it is unclear if the two autoimmune phenotypes of the patient, type I diabetes and Hashimoto's thyroiditis, are also due to IL-18BP deficiency. The child had AR complete IL-18BP deficiency and there are no more than $2.5\times10^{-8}$ such patients in the general population. IL-18 is a pleiotropic inflammatory cytokine that was initially discovered in mouse liver and has been reported to activate NK cells and T cells in addition to its potent IFN-γ-inducing activity (Kaplanski, 2018). Serum and hepatic concentrations of IL-18 and IFN-γ were high in patients with various forms of fulminant liver failure (Shinoda et al., 2006; Yumoto et al., 2002). In particular, serum IL-18 was found to be dramatically elevated in patients with acute hepatitis due to HAV infection (Kim et al., 2018). Moreover, mouse IL-18 has been shown to induce intrahepatic inflammatory cell recruitment and severe hepatotoxicity in various liver injury models (Finotto et al., 2004; Kimura et al., 2011; Tsutsui et al., 2000), whereas IL-18BP has been shown to protect against IL-18-mediated fulminant hepatitis in mice (Faggioni et al., 2001; Fantuzzi et al., 2003; Shao et al., 2013). Our findings indicate that uncontrolled IL-18 activity in humans is toxic to the liver, as previously demonstrated in mice, and that human IL-18BP is a potent liver-protective compound, acting as an antidote to IL-18. Recombinant human IL-18BP (Tadekinig Alfa, AB2 Bio Ltd, Switzerland) has been approved for clinical use for indications unrelated to liver conditions and proposed as a treatment for preventing acetaminophen hepatotoxicity (Bachmann et al., 2018). We provide proof-of-principle that FVH can be caused by single-gene inborn errors of immunity to HAV in the liver. Our findings also reveal the essential functions of IL-18 and IL-18BP in humans. By inference from previous human genetic study of other isolated infections, which are characterized by genetic heterogeneity but physiological homogeneity (Casanova, 2015a; Casanova, 2015b; de Jong et al., 2018; Hernandez et al., 2018; Martinez-Barricarte et al., 2018), there might be other genetic etiologies of FVH that impair IL-18BP or enhance IL-18 activity. Furthermore, neutralizing endogenous IL-18, particularly with recombinant IL-18BP, might be beneficial to patients with FVH caused by HAV and possibly other viruses.

MATERIALS AND METHODS

Patient Recruitment and Ethics

Clinical history and biological specimens were obtained from the referring clinicians, with the consent of the patients and family members participating in the study. All the experiments involving human subjects conducted in this study were in accordance with institutional, local, and national ethical guidelines, and approved by the French Ethics Committee, the French National Agency for the Safety of Medicines and Health Products, and the French Ministry of Research (protocol C09-18), and the Rockefeller University Institutional Review Board (protocol JCA-0700).

Case Report

The patient (III.1) was born in France in 2002 to consanguineous Algerian parents. In 2004, she was diagnosed with insulin-dependent diabetes. Tests for anti-islet cell and anti-insulin autoantibodies were positive, but no anti-glutamic acid decarboxylase antibodies were detected (Table 4). In 2009, anti-thyroglobulin autoantibodies were detected, but tests for anti-glutaminase, anti-endomysium and anti-thyroperoxidase antibodies were negative. Celiac disease was therefore excluded. In 2011, the patient was diagnosed with Hashimoto thyroiditis and tests for anti-thyroperoxidase antibodies were positive (Table 4). The patient was treated with levothyroxine. In 2013, the patient presented with fatigue, nausea, and hepatomegaly. She tested positive for HAV IgM on presentation, consistent with primary HAV infection. Serology and PCR results were negative for HBV (other than the presence of anti-HBs due to prior vaccination), HCV, or HEV. The patient was seropositive for CMV and EBV, and negative for HIV, HTLV1 and 2. PCR tests for enterovirus were negative. No liver autoantibodies (anti-NA, anti-SMA, anti-LKM1, anti-LC1, anti-SLA, anti-mitochondria) were detected, excluding autoimmune hepatitis. The patient had no history of exposure to hepatotoxic drugs, and screening tests for such drugs were negative. Liver function tests were as follows: alanine aminotransferase (ALT): 2181 IU/L, aspartate aminotransferase (AST): 2582 IU/L, γ-glutamyl transferase (GGT): 73 IU/L, total bilirubin: 274 μmol/L, conjugated bilirubin: 173 μmol/L, prothrombin time (PT) at 67%, and Factor V at 100% (Table 5). On day 8 of infection, the patient was hospitalized for incoherent speech, jaundice, appetite loss, gingival bleeding, and petechiae. During physical examination at the emergency unit, the patient was unconscious, with icterus, hepatomegaly, and a fever (40° C.). The patient was diagnosed with fulminant viral hepatitis (FVH) due to HAV infection. On day 9, liver function tests revealed high levels of cytolysis, with a PT of 14%, factor V levels at 30%, and a Glasgow coma scale score of 8 (Table 5). The patient underwent liver transplantation, but died a day later of multiple organ failure (day 11). Histological examinations of the native and explanted liver showed 95% hepatocellular necrosis with polymorphic inflammation. The patient had been vaccinated against BCG, *Haemophilus influenzae* type b, pneumococcus, flu, HBV, and MMR with no adverse effects. She was not tested for immunodeficiency. Her polymorphonuclear cell (PMN) counts were consistently in the normal range (Table 6).

Both parents were seropositive for HAV (IgM-negative) and had normal transaminase levels at the time of the patient's illness (data not shown). The patient's two siblings (III.2 and III.3) had IgM antibodies against HAV and were admitted to hospital two days after she died, but neither developed FVH. The patient's older brother (III.2), born in 2005, had diarrhea and four vomiting episodes two days before hospitalization. On arrival at the hospital, his clinical examination was normal, with no fever, weight loss, icterus, encephalopathy or hepatosplenomegaly. His laboratory findings on day 1 were as follows: ALT, 42 IU/L; AST, 44 IU/L; GGT, 55 IU/L; Hb, 14.8 g/dL; total bilirubin, 6 μmol/L; CRP<5; and PT at 100%. Basic metabolic tests gave normal results. The findings on day 2 were as follows: ALT, 35 IU/L; AST, 36 IU/L; GGT, 48 IU/L; total bilirubin, 10 μmol/L; and PT at 89%. Acute HAV infection was diagnosed. On day 3, no vomiting or diarrhea was observed. Hepatic data had returned to normal except for GGT, at 41 IU/L, PT at 100%, and Factor V at 93% (Table 5).

The patient's other sibling (III.3), born in 2011, had no symptoms before hospitalization. Clinical examination was normal on arrival at the hospital and laboratory findings were as follows: ALT, 1594 IU/L; AST, 755 IU/L; GGT, 293 IU/L; total bilirubin, 10 μmol/L; and PT at 92%. Laboratory findings on day 2 were as follows: ALT, 1298 IU/L; AST, 513 IU/L; GGT, 277 IU/L; total bilirubin, 11 μmol/L. Acute HAV infection was diagnosed. Laboratory findings on day 3 were as follows: ALT, 894 IU/L; AST, 271 IU/L; GGT, 229 IU/L; total bilirubin, 7 μmol/L; PT at 100%, and Factor V at 100% (Table 5). This sibling suffered one episode of diarrhea and vomiting. By day 4, both siblings were discharged from the hospital. None of the parents or siblings has ever had any other symptoms of hepatitis or another liver disease to date.

Whole-Exome Sequencing (WES) and Genetic Analysis

Genomic DNA extraction, WES data collection and analyses were performed as previously described (Belkaya et al., 2017; Regateiro et al., 2017). Briefly, allele frequencies were obtained from National Heart, Lung, and Blood Institute (NHLBI) GO Exome Sequencing Project (EVS, ESP6500SI-V2 release on evs.gs.washington.edu/EVS), 1000 Genomes Project (April 2014 data release on browser.1000genomes.org), and the Genome Aggregation Database (GnomAD, February 2017 data release on gnomad.broadinstitute.org/). All variant calls with a genotype quality (GQ)<20, and a depth of coverage (DP)<5 were filtered out. Only indel-inframe, indel-frameshift, start-lost, missense, nonsense, stop-lost, and essential splice-site (splice acceptor and splice donor) variants were retained for further analysis. Given the rare occurrence of FVH in children, we excluded common polymorphisms with an allele frequency (AF) of 0.1% or more in public databases: EVS, 1000 Genomes, and GnomAD, including variants with an AF≥0.1% in each ethnic subpopulation (African, Ashkenazi Jewish, Finnish, non-Finnish European, South Asian, East Asian, and Latino) in GnomAD. In silico predictions of the impact of variants were evaluated with the following algorithms: the gene damage index (GDI, pec630.rockefeller.edu:8080/GDI/) (Itan et al., 2015), CADD (cadd.gs.washington.edu/score) (Kircher et al., 2014) and mutation significance cutoff (MSC, pec630.rockefeller.edu/MSC/) (Itan et al., 2016). MSC scores were generated with a 99% confidence interval based on the CADD 1.3 scores of all disease-causing mutations in the Human Gene Mutation Database, regardless of the gene concerned (Itan et al., 2016).

Sanger Sequencing of Genomic DNA

We validated genomic variants in patients and/or their relatives, by amplifying 200-300 base-pair (bp) regions encompassing the mutation from gDNA samples with different sets of site-specific primers (Seq-1 and Seq-2 forward/reverse primer sets) listed in Table S7. The amplicons were then sequenced with BigDye Terminator technology on an ABI 3730 DNA sequencer. SnapGene (Version 3.1.4) was used for sequence analysis.

Gene Expression Analyses

EBV-transformed B (EBV-B) cells were generated, as previously described (Durandy et al., 1997), and cultured in RPMI-1640 supplemented with 10% fetal bovine serum (FBS). Total RNA was isolated with a Qiagen RNeasy kit, using EBV-B cells from healthy controls and the healthy siblings and parents of the patient. For quantitative PCR (qPCR) analysis, cDNA samples generated with oligo-dT primer and the SuperScript III First-Strand Synthesis System (Thermo Fisher Scientific) were used to determine the relative levels of IL18BP expression, by amplification of the cDNA generated with TaqMan Universal PCR Master Mix and various TaqMan probes detecting the transcript variants encoding IL-18BPa: Hs00931914 (Probe 1), Hs00931907 (Probe 2), Hs00931908 (Probe 3), and Hs00934414 (Probe 4)(Thermo Fisher Scientific). We used an Applied Biosystems 7500 Fast Real-Time PCR system with the running program: 50° C. for 2 min; 95° C. for 10 min; 40 cycles of 95° C. for 15 s, 60° C. for 1 min. We calculated qPCR efficiency and the amplification factor for each assay by the standard curve method (Nolan et al., 2006) and used them to determine relative expression levels for IL18BP normalized against endogenous GAPDH (4310884E, Thermo Fisher Scientific) expression in each sample. For relative quantification of the WT and mutant IL18BP transcript variants, we used PowerUp SYBR Green Master Mix (Thermo Fisher Scientific) on an Applied Biosystems 7500 Fast Real-Time PCR system with the following program: 50° C. for 2 min; 95° C. for 2 min; 35 cycles of 95° C. for 15 s, 63° C. for 1 min, 72° C. for 30 s (data collection), followed by the melting curve protocol: 95° C. for 15 s; 63° C. for 1 min; 95° C. for 30 s (1% ramp-rate); 60° C. for 15 s. The primer pairs for each mutant variant (M1, M2, and M3) were designed with the NCBI Primer-BLAST tool (ncbi.nlm.nih.gov/tools/primer-blast). The specificity of these primers was assessed by melting curve analysis and confirmed by Sanger sequencing of the qPCR products. Relative copy numbers were determined by the standard curve method with plasmids containing the WT or mutant IL18BP sequences, followed by normalization against endogenous GAPDH (PrimerBank ID: 378404907c1) levels. The sequences of the SYBR Green qPCR primers are provided in Table 7. All qPCR experiments were performed in duplicate with two independent RNA preparations.

Human hepatoma cells (Hep3B), SV40-transformed human fibroblasts (SV40-fibroblasts) and human hepatic stellate cells (LX-2, Millipore, USA) were cultured in DMEM supplemented with 10% fetal calf serum (FCS). Human umbilical vein endothelial cells (HUVECs) were cultured in endothelial cell growth medium (Sigma Aldrich). THP1 (monocytes), Jurkat (T cells), Raji (B cells) and NKL (NK cells) cells were cultured in RPMI-1640 supplemented with 10% FCS. Sodium pyruvate (1 mM) was included in the growth media for THP1 and NKL cells. NKL cells were cultured in the presence of recombinant human IL-2 (10 ng/mL; Invitrogen). All cell lines (Hep3B cells at $1\times10^6$ cells/well, HUVECs at $5\times10^5$ cells/well, Jurkat cells at $2\times10^6$ cells/well, LX-2 cells at $1\times10^6$ cells/well, NKL cells at $2\times10^6$ cells/well, Raji cells at $2\times10^6$ cells/well, SV40 fibroblasts at $5\times10^5$ cells/well, and THP1 cells at $1\times10^6$ cells/well) were plated in fresh medium in 12-well plates on the day before stimulation with various cytokines: IFN-α, at 5000 U/mL (IntronA, IFN-α2b, Schering-Plough); IFN-γ, at 1000 IU/mL (Imukin, IFN-γ1 b, Boehringer); TNF-α, at 10 ng/mL (R&D Systems); IL-6, at 25 ng/mL (R&D Systems); and IL-15, IL-18, IL-22 and IL-29/IFN-λ1, all at 100 ng/mL (R&D Systems). For qPCR analysis, cells were stimulated for 6 h. Total RNA was extracted with the RNeasy Extraction Kit (Qiagen). RNA was reverse-transcribed in High-Capacity RNA-to-cDNA Master Mix (Applied Biosystems). We then performed qPCR in TaqMan assays specific for IL18 (Hs01038788), IL18BP (Hs00931914), IL18R1 (Hs00977691), and IL18RAP (Hs00977695). GAPDH (Hs99999905) was used as an endogenous control for IL18BP, IL18R1 and IL18RAP, whereas HPRT1 (Hs99999909) was used for IL18. Relative expression analyses were performed by the dCt method, according to the kit manufacturer's instructions.

Expression of alternative splice forms of IL18BP was assessed by PCR amplification with different primer sets ($F_{Ex1-2}$ and $R_{IL18BPa}$; $F_{Ex1-2}$ and $R_{IL18BPbd}$; $F_{Ex1-2}$ and $R_{IL18BPc}$; $F_{Ex2-3}$ and $R_{IL18BPa}$; $F_{Ex2-3}$ and $R_{IL18BPd}$; $F_{Ex2-3}$ and $R_{IL18BPc}$) on cDNAs generated using total RNA from HepG2 cells, THP1 cells, and primary human hepatocytes isolated from human liver chimeric mice (Michailidis et al., 2019, manuscript submitted). The primer sequences are provided in Table 7. For IL-18 and IL-18BP ELISAs (DuoSet, R&D Systems) cells were stimulated for 24 h with the concentrations indicated above. Supernatants were obtained and kept at −80° C. ELISA was performed in accordance with the kit manufacturers' instructions.

Flow Cytometry

Unstimulated and stimulated cells were washed with PBS including 2% FCS and 2 mM EDTA. Adherent cell lines were detached with trypsin (Invitrogen) prior to PBS washing. Only certain cell lines, HUVEC, LX-2, NKL and THP1, which had induced IL18R1 mRNA expression upon stimulation with various cytokines, were stimulated for 24 h, as described above in the section of gene expression analyses, and further analyzed for surface IL-18R1 expression by flow cytometry. Cells were then fixed with Fix Buffer I (BD Biosciences) for 10 minutes at 37° C. and washed twice. Staining was performed using a primary antibody against IL-18R1 (R&D Systems) for 1 hour at room temperature, followed by washing and secondary staining with Goat IgG (H+L) APC-conjugated Antibody (R&D Systems) for 30 minutes at room temperature. Cells were washed twice and acquired on a Gallios flow cytometer (Beckman Coulter). Analyses were performed with the FlowJo software (FlowJo). Of note, surface IL-18RAP expression on the cell lines above was not assessed, as we did not validate any antibody specific for human IL-18RAP detection by flow cytometry using control transfected cell lines (data not shown).

3' RACE and Exon Trapping

Rapid amplification of 3' cDNA ends (3' RACE) was performed as previously described (Scotto-Lavino et al., 2006). Briefly, cDNA was synthesized with an adapter primer (AP-1) and SuperScript II Reverse Transcriptase (Thermo Fisher Scientific) from total RNA isolated from the EBV-B cells of a healthy control and the patients' siblings. The first PCR amplification of 3' partial cDNA ends was performed with a forward primer ($F_{Ex1}$) specific to IL18BP exon 1, and a universal amplification primer (UAP-1) binding to AP-1. The PCR products were purified and used for nested PCR with an IL18BP-specific primer ($F_{Ex1-2}$) spanning the junction of exons 1 and 2, and an abridged universal amplification primer (AUAP). The final amplicons generated from the WT and heterozygous sibling samples were ligated into the pGEM-T-Easy vector (Promega) and the colonies were sequenced. For in vitro 3' terminal exon-trapping experiments, 1558 bp DNA fragments starting with a 3'-fragment of IL18BP intron 3 (43 bp) were amplified from the genomic DNA samples of the WT sibling and the patient, with pTAG4-IL18BP forward and reverse primers. These fragments were between thee EcoRI and XhoI sites of the pTAG4 vector. The pTAG4 exon-trapping vector (Krizman and Berget, 1993) was kindly provided by Dr. Anders Lade Nielsen. COS7 cells were transfected with one WT and one mutant clone in the presence of X-tremeGENE 9 DNA Transfection Reagent (Roche). After 16 h, total RNA was extracted with the RNeasy Mini Kit (QIAGEN), treated with DNase (TURBO DNA-free Kit, Invitrogen), and used for cDNA synthesis with the SuperScript III First-Strand Synthesis System (Life Technologies) and an adapter primer (AP-2)(Blechingberg et al., 2007). The first PCR was performed with a specific primer ($F_{AD1-2}$) spanning the junction of AD exons 1 and 2, and the UAP-2, which binds to AP-2. This reaction was followed by nested PCR with a specific primer ($F_{AD2-Ex4}$) encompassing the junction of AD exon 2 and IL18BP exon 4, and a reverse primer (Ru-m) binding to the end of the IL18BP 3' UTR. The nested PCR products were inserted into the pGEM-T-Easy vector and the colonies were sequenced. Successful and equivalent cDNA synthesis was confirmed by the amplification by PCR of HPRT1, as the housekeeping gene control. SnapGene was used to analyze the DNA sequences of the clones. All clones carrying PCR artifacts or sequences not matching the IL18BP canonical transcript were excluded from subsequent analyses. Digital images were captured by the Amersham Imager 600 (GE Healthcare, Life Sciences). The primer sequences are provided in Table 7.

Generation of IL18BP Constructs and Site-Directed Mutagenesis (SDM)

The human canonical IL18BP cDNA ORF clone (CCDS8206) was obtained from OriGene and inserted into the pEF-BOS-EX mammalian expression plasmid (Murai et al., 1998), which was kindly provided by Dr. Shigekazu Nagata. The forward primer (IL18BP BamHI) included a BamHI site and a Kozak consensus sequence; whereas the reverse primer (IL18BP-His XbaI) contained an in-frame coding sequence for a C-terminal 6x-His tag and an XbaI site. Site-directed mutagenesis (SDM) to generate the IL18BP variants present in GnomAD (p.V23I, p.R121Q, and p.P184L) was performed by a modified overlap-extension PCR-based method (Shimada, 1996). IL18BP BamHI/SDM-Reverse primers and SDM-Forward/IL18BP-His XbaI primers were used to amplify the mutated IL18BP in two separate reactions, using the pEF-BOS-EX-IL18BP-His WT plasmid as the template. Each PCR product was purified and the different products were mixed without primers for overlap-extension PCR. SDM for the p.Q192H allele was performed by one-step PCR with the IL18BP BamHI and Q192H-His-XbaI primers. Novel IL18BP transcript variants (M1, M2, and M3) were generated with the IL18BP BamHI and SDM-Reverse primers or the SDM-Forward and mutant reverse primers (containing an in-frame coding sequence for a C-terminal 6x-His tag, a stop codon and an XbaI site) in two separate reactions, using the pEF-BOS-EX-IL18BP-His WT plasmid and control gDNA, respectively, as templates. The M1 and M2 transcripts were cloned including an 18 nt poly-A insert downstream of the 6x-His tag, followed by a stop codon. All constructs were confirmed by DNA sequencing. The primer sequences are provided in Table 7.

Transient Expression of IL-18BP and Immunoblotting

COS7 cells were used to seed six-well plates at a density of $2\times10^5$ cells/well, in DMEM supplemented with 10% FBS. They were transfected with pEF-BOS-EX-IL18BP-His constructs (500 ng per well) in the presence of the X-tremeGENE 9 DNA transfection reagent (Roche Applied Sciences). The culture medium was removed six hours after transfection, and the cells were incubated for three days in serum-free OPTIMEM. Culture supernatants were concentrated by centrifugation on Amicon centrifugal protein filters (3 kDa; EMD Millipore) according to the manufacturer's instructions, and were stored at −80° C. for later use. Total protein concentration in the COS7 supernatants was determined with a Pierce BCA protein assay kit (Thermo Fisher Scientific) and total protein (15 μg protein per lane) was then subjected to SDS/PAGE (12% polyacrylamide gel) under reducing conditions. Immunoblotting was performed with primary antibodies against the His-Tag (MAI-21315, 0.5 μg/mL, Thermo Fisher Scientific) and IL-18BP (AF119 at 0.5 μg/mL, R&D Systems). Digital images were captured by the Amersham Imager 600 (GE Healthcare, Life Sciences).

IL-18BP Bioassay

The bioactivity of human IL-18BP was assessed by measuring inhibition of the IFN-γ-inducing activity of human IL-18 in NK-92 cells. Briefly, NK-92 cells were cultured in RPMI supplemented with 10% FBS and 200 IU/ml IL-2 (Chiron). Before the IL-18BP bioassay, NK-92 cells were rested for 24 h in the absence of IL-2. Rested NK-92 cells, at a density of $0.5\times10^6$ cells/mL in flat-bottomed 96-well plates, were stimulated for 24 h with 100 μg/mL IL-12 (R&D Systems), 10 ng/mL IL-18 (R&D Systems), and various concentrations of recombinant IL-18BP-His (125-500 ng/mL, Sino Biologicals) or with concentrated supernatants (100 μg/mL of total protein) from COS7 cells transiently transfected with IL-18BP constructs. IL-18 and IL-18BP were mixed together and incubated for 1 h at 37° C. before their addition to cells. At 24 h, the supernatants were used for ELISA, to assess IFN-γ production (Human IFN gamma Ready-Set-Go, Thermo Fisher Scientific). All IL-18BP bioassays were performed in duplicate.

Immunohistochemistry

Immunohistochemical staining was performed on 4 μm-thick sections of formalin-fixed paraffin-embedded (FFPE) tissue samples, with Bond autostainer (Leica, Newcastle upon Tyne, UK), after antigen retrieval and endogenous peroxidase inhibition with $H_2O_2$ (3%). We used primary antibodies against CD3 (polyclonal rabbit, CD3epsilon, A0452, Dako, Agilent), CD4 (monoclonal IgG1k mouse, NCL-L-CD4-368, Leica), CD8 (monoclonal IgG1k mouse, C8/144B, Dako), CD20 (monoclonal IgG2ak mouse, L26, Dako), CD57 (monoclonal IgM mouse, NK-1, Leica), CD68 (monoclonal IgG2a mouse, 514H12, Leica), CD163 (monoclonal IgG1 mouse, NCL-L-CD163, Leica), perforin (monoclonal IgG1 mouse, 5B10, Leica), NKp46 (polyclonal IgG goat, AF1850, R&D Systems), and Hep Par-1 (monoclonal IgG1k mouse, OCH1E5, Dako). These antibodies were detected and the signal was amplified with the Bond Polymer Refine Detection kit (DS9800, Leica) and hematoxylin counterstaining. We also used primary antibodies against IL-18BP (monoclonal mouse, clone 13603, R&D), IL-18BP (polyclonal rabbit, HP37434, Sigma), and IL-18 (polyclonal rabbit, HPA0003980, Sigma). These antibodies were detected and the signal was amplified with the Bond Intense R kit (DS9263, Leica) and hematoxylin counterstaining. Native explanted livers are usually fixed in formalin at room temperature during 3 to 8 days, while most other tissue samples are fixed during 6 to 72 hours. This long immersion in formalin may be responsible for alteration of some epitopes and for increased background signals when performing immunohistochemistry. Moreover, the most efficient kits available for immunohistochemistry include a streptavidin-biotin amplification step. This may also explain for increased background signals during immunohistochemistry staining, as hepatocytes contain endogenous biotin. Although IL-18BP staining was validated on control transfected cell lines, the staining observed in healthy or diseased livers was not significantly different from the staining detected with the diluent without the primary antibody as negative control (data not shown). Normal liver corresponds to liver parenchyma of patients who did not receive chemotherapy and underwent surgery for metastasis of colon carcinoma. The sampling was at least 2 cm away from the nearest metastasis.

Coculture Experiments and HAV Infection

HepG2 cells (kindly provided by Dr. Yosef Shaul, Weizmann Institute of Science, Israel) were used to seed collagen-coated 96-well plates at $1.5\times10^4$ cell/well, in DMEM supplemented with 10% FBS and 0.1 mM non-essential amino acids (NEAA). NK92 cells ($1\text{-}2\times10^6$ cell/mL in 24-well plates) were stimulated with IL-18 (200 ng/mL) and/or IL-18BP (1000 ng/mL) in the absence of IL-2 for 18 h. IL-18 and IL-18BP were mixed together and incubated for 1 h at 37° C. before their addition to cells. On the day of coculture, HepG2 cells, at 80-90% confluence, were washed once with serum-free RPMI, and stained with calcein-AM (0.5 μM, Trevigen) for 30 min at 37° C. (Bugide et al., 2018; Somanchi et al., 2015). Calcein-labeled HepG2 cells were washed twice with complete RPMI. Activated NK cells, washed and resuspended in complete RPMI, were added at a density of $1\text{-}3\times10^5$ cells/well to HepG2 cells, and the two cell types were cocultured at 37° C. for 4 h. PBMCs from healthy donors were isolated by Ficoll-Paque density gradient, as previously described (Hernandez et al., 2018). Isolated PBMCs ($4\times10^6$ cell/mL in 24-well plates) were stimulated with IL-18 (200 ng/mL) and/or IL-18BP (1000 ng/mL) in the presence of IL-2 (400 IU/mL) for 24 h. Stimulated PBMCs, washed and resuspended in complete RPMI, were cultured at various densities ($2\text{-}4\times10^5$ cells/well) with HepG2 cells for 4 h.

HepG2 and Huh7.5 cells were infected with HAV (HM-175/18f) at various dilutions and maintained in DMEM supplemented with 3% FBS and 0.1 mM NEAA for several days. At 3 days post-infection, when HepG2 and Huh7.5 cells reached to maximum infection rates, 40% and 100%, respectively, both mock- and HAV-infected hepatocytes were detached and reseeded on collagen-coated 96-well plates at $1.5\times10^4$ cell/well. Surplus infected cells were lysed for RNA isolation, and their supernatants were stored for future use. On the following day, calcein-labeled mock- or HAV-infected HepG2 cells were cultured with NK-92 cells ($3\times10^5$ cells/well), which were activated with IL-18 and/or IL-18BP, as described above. For Huh7.5 cells, NK-92 cells were stimulated with IL-18 (200 ng/mL) and/or IL-18BP (1000 ng/mL) in the presence of IL-2 (20 IU/mL) for 18 h and cultured at $3\times10^5$ cells/well with calcein-labeled mock- or HAV-infected Huh7.5 cells. After 4 h of coculture, supernatants were collected and stored at −80° C. for later use. Cells were washed twice with PBS and fixed by incubation with 4% PFA for 20 min at room temperature in the dark. The nuclei were then stained with DAPI (D1306 at 1/5000, Thermo Fisher Scientific). For high-content imaging analyses, ImageXpress Micro XLS (Molecular Devices, Sunnyvale, CA) and MetaXpress PowerCore software were used. The total-cell integrated intensity of calcein-positive cells was determined for each well and adjusted by subtracting the background fluorescence (unstained hepatocyte cells). As an alternative to fluorescence imaging, albumin levels in hepatocyte-NK cell cocultures were determined by ELISA, as previously described (de Jong et al., 2014). Relative fluorescence and albumin levels were determined by normalization against the mean value for hepatocytes cocultured with effector cells (NK-92 cells or PBMCs) without pretreatment, set to 100. All coculture experiments were performed in quadruplicate.

For HAV immunostaining, infected hepatocytes were fixed with 4% PFA for 30 min at room temperature. Fixed cells were washed twice with PBS and incubated with 100 mM Glycine for 15 min. Cells were then permeabilized for 10 min using PBS with 0.1% Triton-X100, followed by blocking for 1 h with PBS+5% Goat serum (Jackson ImmunoResearch, Code 005-000-121). Cells were stained with primary antibodies against HAV (Mouse anti-HAV VP1, K2-4F2, Creative Biolabs; Mouse Anti-HAV, 7E7, Mediagnost) at 1/1000 for overnight at 4° C., followed by staining with Goat-anti-mouse AlexaFluor 594 at 1/1000 and DAPI at 1/5000 for 1 h at room temperature. All antibody dilutions were carried out in PBS+5% Goat serum. Finally, cells were imaged using a Nikon Eclipse TE300 fluorescent microscope, and images were processed with ImageJ.

Total RNA and supernatants harvested from infected HepG2 and Huh7.5 cells were utilized for expression analysis of IL18 and IL18BP by qPCR and ELISA, as described above, however no mRNA and protein induction of IL18 or IL18BP was detected in HAV-infected HepG2 or Huh7.5 hepatocytes (data not shown).

Statistical Analysis

The results of the experiments were plotted as means±SEM. GraphPad Prism Software (www.graphpad.com) was used to calculate mean values and SEM, and for one-way ANOVA. Statistical significance is indicated by asterisks (*, P<0.05, , P<0.01, and *, P<0.001), with P values greater than 0.05 considered non-significant (n.s.).

Data Availability

The WES data are available in the Sequence Read Archive (ncbi.nlm.nih.gov/sra) with the BioProject accession number PRJNA543035.

Tables

The tables referenced in this Example 1 are provided below. Table 1 summarizes the genetic analysis of the WES data of the patient and two siblings. Table 2 lists the homozygous rare nonsynonymous variations present only in the patient. Table 3 describes the characteristics of genes with homozygous rare nonsynonymous variations present only in the patient. Table 4 provides other clinical findings of the patient prior to fulminant viral hepatitis. Table 5 shows the analytical findings in the patient and her siblings following HAV infection. Table 6 presents the immunological phenotyping data of the patient. Table 7 lists the primers used in this study.

TABLE 1

Genetic analysis of the WES data of the patient and two siblings

| WES data analysis | | | |
|---|---|---|---|
| Number of annotated variations (Number of mutated genes) | III.1 (Patient) | III.2 (Sibling) | III.3 (Sibling) |
| Total | 142,213 (19,550) | 141,383 (19,650) | 141,145 (19,665) |
| Nonsynonymous & essential splicing | 12,140 (6,148) | 12,168 (6,232) | 12,232 (6,234) |

TABLE 1-continued

Genetic analysis of the WES data of the patient and two siblings

| WES data analysis | | | |
|---|---|---|---|
| Number of annotated variations (Number of mutated genes) | III.1 (Patient) | III.2 (Sibling) | III.3 (Sibling) |
| MAF < 0.1% | 241 (230) | 240 (222) | 271 (246) |
| Homozygous | 9 (9) | 12 (12) | 7 (7) |
| Present only in the patient | 6 (6) | — | — |

Only nonsynonymous (indel-inframe, indel-frameshift, start-lost, missense, nonsense, stop-lost) and essential splice-site (splice acceptor and splice donor) variants were selected. Variants with a minor allele frequency (MAF) of 0.1% or greater in public databases: EVS, 1000 Genomes, and GnomAD, including variants with an AF≥0.1% in each ethnic subpopulation (African, Ashkenazi Jewish, Finnish, non-Finnish European, South Asian, East Asian, and Latino) in GnomAD were excluded. Finally, under the autosomal recessive model of inheritance, only homozygous variants were selected, and six genes with homozygous variants present only in the patient were considered to be candidate disease-causing genes. The number of genes mutated is shown in parentheses.

TABLE 2

Homozygous rare nonsynonymous variations present only in the patient

| | | | Variation | | Zygosity | | | | |
|---|---|---|---|---|---|---|---|---|---|
| Gene | GDI[&] | NI[#] | Type | Change | III.1 | III.2 | III.3 | MAF | CADD/MSC |
| IL18BP | 2.05 | 1.764 | deletion | NM_173042.2:c.508-19_528del | hom | het | wt | 0 | 28.2/12.19 |
| ADAMTS1 | 4.70 | 0.100 | missense | NM_006988:p.Lys648Arg | hom | wt | wt | 2.06E−04 | 25/17.33 |
| SLC6A19 | 6.44 | 0.152 | missense | NM_001003841.2:p.Val551Met | hom | het | het | 9.39E−05 | 25.1/14.87 |
| TM7SF2 | 9.21 | 3.610 | missense | NM_003273.3:p.Ala36Gly | hom | het | wt | 3.24E−05 | 16.63/16.48 |
| ZNF324 | 1.65 | 0.143 | missense | NM_014347.2:p.Ile385Met | hom | het | het | 0 | 23.2/12.19 |
| ZNF814 | 2.16 | 0.005 | missense | NM_001144989.1:p.His407Asp | hom | het | het | 3.54E−05 | 15.57/12.19 |

Total 6 genes were identified with rare (MAF < 0.001) nonsynonymous variants present at homozygous state only in the patient.

[&]GDI: Gene Damage Index, where the range is between 0.0001 for least damaged human gene and 42.91 for most damaged human gene.

[#]NI: McDonald-Kreitman neutrality index (NI) measurement, where NI < 1 indicates a purifying selection.

TABLE 3

Characteristics of genes with homozygous rare nonsynonymous variations present only in the patient

| Gene description | Expression pattern | Known function | Clinical significance |
|---|---|---|---|
| Interleukin 18 binding protein (IL18BP) | Broad expression in spleen, appendix, lymph nodes, and 23 other tissues | Inhibitor of the proinflammatory cytokine, IL18 | Unknown |
| ADAM metallopeptidase with thrombospondin type 1 motif 1 (ADAMTSI) | Broad expression in ovary, placenta, and 17 other tissues | Role in growth, fertility, and organ morphology and function | Unknown |

TABLE 3-continued

| Characteristics of genes with homozygous rare nonsynonymous variations present only in the patient | | | |
|---|---|---|---|
| Gene description | Expression pattern | Known function | Clinical significance |
| Solute carrier family 6 member 19 (SLC6A19) | Broad expression in small intestine, duodenum, and kidney | Transportation of most neutral amino acids across the apical membrane of epithelial cells | Biallelic mutations in this gene cause Hartnup disorder |
| Transmembrane 7 superfamily member 2 (TM7SF2) | Broad expression in adrenal, fat, and 20 other tissues | Role in cholesterol biosynthesis | Unknown |
| Zinc finger protein 324 (ZNF324) | Ubiquitous expression in brain, ovary, and 25 other tissues | May be involved in transcriptional regulation | Unknown |
| Zinc finger protein 814 (ZNF814) | Ubiquitous expression in prostate, spleen, and 25 other tissues | May be involved in transcriptional regulation | Unknown |

Information related to the expression pattern, known function and clinical significane of these six genes in humans were obtained from the NCBI Gene database.

TABLE 4

Other clinical findings of the patient prior to fulminant viral hepatitis

| Clinical findings# | July 2004 | October 2005 | March 2007 | October 2009 | April 2011 | September 2012 | November 2013 |
|---|---|---|---|---|---|---|---|
| Thyroiditis | | | | | | | |
| anti-TPO (positive >60 IU/mL) | NA | Negative (<45) | Negative (<60) | NA | Positive (145) | NA | NA |
| anti-PO (positive >10 IU/mL) | NA | NA | NA | Negative | Positive (51) | NA | NA |
| anti-TG (positive >116 IU/mL) | NA | Negative (<90) | Negative (<60) | Positive | NA | NA | NA |
| Free T4 (normal: 1-1.07 ng/dL) | NA | NA | NA | NA | Positive (2.66) | Normalization upon treatment | |
| TSH (normal: 0.4-4 mIU/L) | NA | NA | NA | NA | Positive (119.22) | Normalization upon treatment | |
| Celiac disease (excluded) | | | | | | | |
| RLA IgA anti-tTG (positive >150 cpm) | NA | Negative (<47) | Negative (<45) | Negative (<66) | NA | Negative (<44) | Negative (<129) |
| EMA | NA | Negative | Negative | Negative | NA | NA | NA |
| Langerhans anti-IC | Positive | NA | NA | NA | NA | NA | NA |
| Diabetes | | | | | | | |
| anti-Insulin (positive >0.7%) | Positive (1.31) | NA | NA | NA | NA | NA | NA |
| anti-IA2 (positive >80 cpm) | Negative (<29) | NA | NA | NA | NA | NA | NA |
| anti-GAD65 (positive >180 cpm) | Negative (<84) | NA | NA | NA | NA | NA | NA |
| Glycemia (normal: 4-6 mmol/L) | High (37) | Normalization upon treatment | | | | | |
| HbA1c (normal: 4-5.6%) | High (8.9) | Normalization upon treatment | | | | | |

#TPO: Thyroid peroxidase,
PO: Peroxidase,
TG: Thyroglobulin,
T4: Thyroxine,
TSH: thyroid-stimulating hormone,
RLA: Radioligand-receptor assay,
tTG: Tissue transglutaminase,
EMA: Endomysial antibodies (IgA),
IC: Islet cells,
IA2: Islet antigen 2,
GAD65: Glutamic acid decarboxylase,
HbA1c: Hemoglobin A1c,
NA: Not available

TABLE 5

Analytical findings in the patient and her siblings following HAV infection

| | Patient (III.1) | | | | | Sibling (III.2) | | | | | Sibling (III.3) | | | | | |
|---|---|---|---|---|---|---|---|---|---|---|---|---|---|---|---|---|
| | | Hospitalization (Day 8-11) | | | | Hospitalization[#] (Day 1-3) | | | Day | Day | Hospitalization[#] (Day 1-3) | | | Day | Day | Day |
| Days | Day 1 | Day 8 | Day 9[$] | Day 10* | Day 11[&] | Day 1 | Day 2 | Day 3 | 5 | 15 | Day 1 | Day 2 | Day 3 | 4 | 5 | 15 |
| IgM anti-HAV (IU/L) | Positive (no value) | >60 | ND | ND | ND | >60 | ND | ND | ND | ND | >60 | ND | ND | ND | ND | ND |
| ALT (<40 IU/L) | 2181 | 1481 | 1117 | 275 | 403 | 42 | 35 | 29 | 27 | 23 | 1594 | 1298 | 894 | 757 | 531 | 96 |
| AST (<40 IU/L) | 2582 | 1982 | 1863 | 1393 | 1182 | 44 | 36 | 34 | 33 | 39 | 755 | 513 | 271 | 149 | 108 | 52 |
| GGT (<25 IU/L) | 73 | 28 | 22 | 27 | 28 | 55 | 48 | 41 | 38 | 33 | 293 | 277 | 229 | 206 | 162 | 55 |
| Factor V (>80%) | 100 | 48 | 30 | 42 | 29 | ND | ND | 93 | 100 | ND | 100 | ND | 100 | 100 | ND | ND |
| PT (>70%) | 67 | 9 | 14 | 82 | 53 | 100 | 89 | 100 | 100 | 100 | 92 | 92 | 100 | 100 | 100 | 98 |

[#]Two siblings (III.2 and III.3) were hospitalized 2 days after the patient died.
[$]Day 9: Values were prior to liver transplantation.
*Day 10: Post-transplantation values are shown.
[&]Day 11: Patient died.

TABLE 6

Immunological phenotyping data of the patient

| PBMC | Day 1 | Day 8 | Day 9 | Day 10 |
|---|---|---|---|---|
| PMNs (normal: 1.5-8 $10^9$/L) | 6.00 | 3.76 | 5.2 | 3.76 |
| Lymphocytes (normal: 1.5-5 $10^9$/L) | 2.21 | 1.44 | 2.26 | 2.38 |
| Monocytes (normal: 0.1-1 $10^9$/L) | 0.44 | 0.41 | 0.08 | 0.12 |

TABLE 7

List of primers used in this study

| Name | Sequence (5'-3') | Application |
|---|---|---|
| Seq-1 Fwd | CAGCCTGTGAACTAATGCC (SEQ ID NO: 3) | Sanger sequencing |
| Seq-1 Rev | GAATTTGGTGAGAGAAGGGA (SEQ ID NO: 4) | Sanger sequencing |
| Seq-2 Fwd | CAAGGAGAGGCCTCCAG (SEQ ID NO: 5) | Sanger sequencing |
| Seq-2 Rev | ACTCCAGGTAGACAGGTAG (SEQ ID NO: 6) | Sanger sequencing |
| IL18BP SYBR Fwd* | CAGCTCTGGGCTGGGCTGAG (SEQ ID NO: 7) | SYBR Green qPCR |
| IL18BP SYBR Rev* | GGGGTGTGTTGCGCATCCAC (SEQ ID NO: 8) | SYBR Green qPCR |
| M1 SYBR Fwd | GGAACGTGGGAGCACAGGTA (SEQ ID NO: 9) | SYBR Green qPCR |
| M1 SYBR Rev | TTGAGCGTTCCCCTGCCAGA (SEQ ID NO: 10) | SYBR Green qPCR |

TABLE 7 -continued

List of primers used in this study

| Name | Sequence (5'-3') | Application |
|---|---|---|
| M2 SYBR Fwd | GGAACGTGGGAGCACAGGTA (SEQ ID NO: 11) | SYBR Green qPCR |
| M2 SYBR Rev | CTTGAGCGTTCCCCCAGAGC (SEQ ID NO: 12) | SYBR Green qPCR |
| M3 SYBR Fwd | CCTGCACAGCACCAACTTCTC (SEQ ID NO: 13) | SYBR Green qPCR |
| M3 SYBR Rev | GAGACATGGGAGTGGGAGCCA (SEQ ID NO: 14) | SYBR Green qPCR |
| GAPDH SYBR Fwd[#] | GGAGCGAGATCCCTCCAAAAT (SEQ ID NO: 15) | SYBR Green qPCR |
| GAPDH SYBR Rev[#] | GGCTGTTGTCATACTTCTCA TGG (SEQ ID NO: 16) | SYBR Green qPCR |
| AP-1 | CCAGTGAGCAGAGTGACGA GGACTCGAGCTCAAGCTTT TTTTTTTTTTTTT (SEQ ID NO: 17) | Exon trapping |
| UAP-1 | CCAGTGAGCAGAGTGACG (SEQ ID NO: 18) | Exon trapping |
| AUAP | GAGGACTCGAGCTCAAGC (SEQ ID NO: 19) | Exon trapping |
| $F_{Ex1}$ | ATGACCATGAGACACAACTGGA (SEQ ID NO: 20) | Exon trapping |
| $F_{Ex1-2}$ | CTGGACACCAGACCTCAGCC (SEQ ID NO: 21) | Exon trapping/ PCR |
| $F_{Ex2-3}$ | CCACTGAATGGAACGCTGAG (SEQ ID NO: 22) | PCR |
| $R_{IL18BPa}$ | TTAACCCTGCTGCTGTGGA (SEQ ID NO: 23) | PCR |
| $R_{IL18BPbd}$ | TCAAGGTTGTGCTGCTGCT (SEQ ID NO: 24) | PCR |

TABLE 7-continued

List of primers used in this study

| Name | Sequence (5'-3') | Application |
|---|---|---|
| $R_{IL18BPc}$ | TCACAGGCTGCTCTGGCA (SEQ ID NO: 25) | PCR |
| pTAG4-IL18BP Fwd | CTGGAATTCCTTCTGCGGCCTT CTCATG (SEQ ID NO: 26) | Exon trapping |
| pTAG4-IL18BP Rev | GCACTCGAGGATGGATCTTTTC TAAATGTT (SEQ ID NO: 27) | Exon trapping |
| AP-2 | GCGGAATTCGGATCCCTCGAGTT TTTTTTTTTTTTTTTT (SEQ ID NO: 28) | Exon trapping |
| UAP-2 | GCGGAATTCGGATCCCTCGAGTT (SEQ ID NO: 29) | Exon trapping |
| $FA_{D1-2}$ | AGGGCCAGCTGTTGGGCTCG (SEQ ID NO: 30) | Exon trapping |
| $F_{AD2-Ex4}$ | CGTCGGCCTCCGAACGCCGGGA (SEQ ID NO: 31) | Exon trapping |
| $R_{UTR}$ | CTCCATTGAATAATCCTTTATGA GGACC (SEQ ID NO: 32) | Exon trapping |
| HPRT1 Fwd | CTGGCGTCGTGATTAGTGATGA TG (SEQ ID NO: 33) | Exon trapping |
| HPRT1 Rev | TTGAGCACACAGAGGGCTACA ATG (SEQ ID NO: 34) | Exon trapping |
| IL18BP BamHI (Kozak) | GTTGGATCCGCCACCATGAGA CACAACTGGACACCA (SEQ ID NO: 35) | Cloning |
| IL18BP-His XbaI | ATATCTAGATTAATGATGAT GATGATGATGACCCTGCTGC TGTGGACTGC (SEQ ID NO: 36) | Cloning |
| V23I SDM Fwd | CTCCTGTGTGCCCACATCGT CACTCTCCTGGTC (SEQ ID NO: 37) | Mutagenesis |
| V23I SDM Rev | GACCAGGAGAGTGACGATGT GGGCACACAGGAG (SEQ ID NO: 38) | Mutagenesis |
| R121Q SDM Fwd | AGGGGAGCACCAGCCAGGAA CGTGGGAGCAC (SEQ ID NO: 39) | Mutagenesis |
| R121Q SDM Rev | GTGCTCCCACGTTCCTGGC TGGTGCTCCCCT (SEQ ID NO: 40) | Mutagenesis |
| P184L SDM Fwd | CACCCAAGAAGCCCTGCTC TCCAGCCACAG (SEQ ID NO: 41) | Mutagenesis |
| P184L SDM Rev | CTGTGGCTGGAGAGCAGGG CTTCTTGGGTG (SEQ ID NO: 42) | Mutagenesis |
| Q192H-His XbaI | ATATCTAGATTAATGATGA TGATGATGATGACCCTGAT GCTGTGGACTGC (SEQ ID NO: 43) | Mutagenesis |
| M1-His XbaI | ATATCTAGATTAATGATGA TGATGATGATGGGATGTTT TTTTTTTTTTTTTTTCTCC ATTGAATAATC (SEQ ID NO: 44) | Cloning |
| M2-His XbaI | ATATCTAGATTAATGATGAT GATGATGATGGGATGTTTTT TTTTTTTTTTTTTCTCCATT GAATAATC (SEQ ID NO: 45) | Cloning |
| M3-His XbaI | ATATCTAGATTAATGATGAT GATGATGATGCTGAAGAGGC AGCATTTCA (SEQ ID NO: 46) | Cloning |
| M1 SDM Fwd | CCAGCTCTGGCAGGGGAAC GCTCAAGCCTG (SEQ ID NO: 47) | Mutagenesis |
| M1 SDM Rev | CGTTCCCCTGCCAGAGCTG GGCCAGGACGA (SEQ ID NO: 48) | Mutagenesis |
| M2 SDM Fwd | CCAGCTCTGGGGGAACGCT CAAGCCTGGTT (SEQ ID NO: 49) | Mutagenesis |
| M2 SDM Rev | GAGCGTTCCCCCAGAGCTGG GCCAGGACGA (SEQ ID NO: 50) | Mutagenesis |
| M3 SDM Fwd | CCAGCTCTGGCTCCCACTCC CATGTCTCTG (SEQ ID NO: 51) | Mutagenesis |
| M3 SDM Rev | GGAGTGGGAGCCAGAGCTG GGCCAGGACGA (SEQ ID NO: 52) | Mutagenesis |

*Khalid KE, Nsairat HN, Zhang JZ (2016) The presence of interleukin 18 binding protein isoforms in Chinese patients with rheumatoid arthritis. AIMS Med Sci 3: 103-113
#PrimerBank ID: 378404907c1

REFERENCES

Aizawa, Y., K. Akita, M. Taniai, K. Torigoe, T. Mori, Y. Nishida, S. Ushio, Y. Nukada, T. Tanimoto, H. Ikegami, M. Ikeda, and M. Kurimoto. 1999. Cloning and expression of interleukin-18 binding protein. *FEBS letters* 445: 338-342.

Ajmera, V., G. Xia, G. Vaughan, J. C. Forbi, L. M. Ganova-Raeva, Y. Khudyakov, C. K. Opio, R. Taylor, R. Restrepo, S. Munoz, R. J. Fontana, W. M. Lee, and G. Acute Liver Failure Study. 2011. What factors determine the severity of hepatitis A-related acute liver failure? *Journal of viral hepatitis* 18:e167-174.

Bachmann, M., J. Pfeilschifter, and H. Muhl. 2018. A Prominent Role of Interleukin-18 in Acetaminophen-Induced Liver Injury Advocates Its Blockage for Therapy of Hepatic Necroinflammation. *Frontiers in immunology* 9:161.

Belkaya, S., A. R. Kontorovich, M. Byun, S. Mulero-Navarro, F. Bajolle, A. Cobat, R. Josowitz, Y. Itan, R. Quint, L. Lorenzo, S. Boucherit, C. Stoven, S. Di Filippo, L. Abel, S. Y. Zhang, D. Bonnet, B. D. Gelb, and J. L. Casanova. 2017. Autosomal Recessive Cardiomyopathy Presenting as Acute Myocarditis. *Journal of the American College of Cardiology* 69:1653-1665.

Blechingberg, J., S. Lykke-Andersen, T. H. Jensen, A. L. Jorgensen, and A. L. Nielsen. 2007.

Regulatory mechanisms for 3-end alternative splicing and polyadenylation of the Glial Fibrillary Acidic Protein, GFAP, transcript. *Nucleic acids research* 35:7636-7650

Bugide, S., M. R. Green, and N. Wajapeyee. 2018. Inhibition of Enhancer of zeste homolog 2 (EZH2) induces natural killer cell-mediated eradication of hepatocellular carcinoma cells. *Proceedings of the National Academy of Sciences of the United States of America* 115:E3509-E3518.

Casanova, J. L. 2015a. Human genetic basis of interindividual variability in the course of infection. *Proceedings of the National Academy of Sciences of the United States of America* 112:E7118-7127.

Casanova, J. L. 2015b. Severe infectious diseases of childhood as monogenic inborn errors of immunity. *Proceedings of the National Academy of Sciences of the United States of America* 112:E7128-7137.

Casanova, J. L., and L. Abel. 2018. Human genetics of infectious diseases: Unique insights into immunological redundancy. *Seminars in immunology* 36:1-12.

Casanova, J. L., M. E. Conley, S. J. Seligman, L. Abel, and L. D. Notarangelo. 2014. Guidelines for genetic studies in single patients: lessons from primary immunodeficiencies. *The Journal of experimental medicine* 211:2137-2149.

de Jong, S. J., A. Crequer, 1. Matos, D. Hum, V. Gunasekharan, L. Lorenzo, F. Jabot-Hanin, E. Imahom, A. A. Arias, H. Vahidnezhad, L. Youssefian, J. G. Markle, E. Patin, A. D'Amico, C. Q. F. Wang, F. Full, A. Ensser, T. M. Leisner, L. V. Parise, M. Bouaziz, N. P. Maya, X. R. Cadena, B. Saka, A. H. Saeidian, N. Aghazadeh, S. Zeinali, P. Itin, J. G. Krueger, L. Laimins, L. Abel, E. Fuchs, J. Uitto, J. L. Franco, B. Burger, G. Orth, E. Jouanguy, and J. L. Casanova. 2018. The human CIB1-EVER1-EVER2 complex governs keratinocyte-intrinsic immunity to beta-papillomaviruses. *The Journal of experimental medicine* 215:2289-2310.

de Jong, Y. P., M. Dorner, M. C. Mommersteeg, J. W. Xiao, A. B. Balazs, J. B. Robbins, B. Y. Winer, S. Gerges, K. Vega, R. N. Labitt, B. M. Donovan, E. Giang, A. Krishnan, L. Chiriboga, M. R. Charlton, D. R. Burton, D. Baltimore, M. Law, C. M. Rice, and A. Ploss. 2014. Broadly neutralizing antibodies abrogate established hepatitis C virus infection. *Science translational medicine* 6:254ra129.

Durandy, A., C. Hivroz, F. Mazerolles, C. Schiff, F. Bernard, E. Jouanguy, P. Revy, J. P. DiSanto, J. F. Gauchat, J. Y. Bonnefoy, J. L. Casanova, and A. Fischer. 1997. Abnormal CD40-mediated activation pathway in B lymphocytes from patients with hyper-IgM syndrome and normal CD40 ligand expression. *Journal of immunology* 158: 2576-2584.

Durst, R. Y., N. Goldsmidt, J. Namestnick, R. Safadi, and Y. Ilan. 2001. Familial cluster of fulminant hepatitis A infection. *Journal of clinical gastroenterology* 32:453-454.

European Association for the Study of the Liver. 2017. EASL Clinical Practical Guidelines on the management of acute (fulminant) liver failure. *Journal of hepatology* 66:1047-1081.

Faggioni, R., R. C. Cattley, J. Guo, S. Flores, H. Brown, M. Qi, S. Yin, D. Hill, S. Scully, C. Chen, D. Brankow, J. Lewis, C. Baikalov, H. Yamane, T. Meng, F. Martin, S. Hu, T. Boone, and G. Senaldi. 2001. IL-18-binding protein protects against lipopolysaccharide-induced lethality and prevents the development of Fas/Fas ligand-mediated models of liver disease in mice. *Journal of immunology* 167:5913-5920.

Fantuzzi, G., N. K. Banda, C. Guthridge, A. Vondracek, S. H. Kim, B. Siegmund, T. Azam, J. A. Sennello, C. A. Dinarello, and W. P. Arend. 2003. Generation and characterization of mice transgenic for human IL-18-binding protein isoform a. *Journal of leukocyte biology* 74:889-896.

Finotto, S., J. Siebler, M. Hausding, M. Schipp, S. Wirtz, S. Klein, M. Protschka, A. Doganci, H. A. Lehr, C. Trautwein, R. Khosravi-Far, D. Strand, A. Lohse, P. R. Galle, M. Blessing, and M. F. Neurath. 2004. Severe hepatic injury in interleukin 18 (IL-18) transgenic mice: a key role for IL-18 in regulating hepatocyte apoptosis in vivo. *Gut* 53:392-400.

Fujiwara, K., O. Yokosuka, K. Fukai, F. Imazeki, H. Saisho, and M. Omata. 2001. Analysis of full-length hepatitis A virus genome in ser from patients with fulminant and self-limited acute type A hepatitis. *Journal ofhepatology* 35:112-119.

Guidotti, L. G., and F. V. Chisari. 2006. Immunobiology and pathogenesis of viral hepatitis. *Annual review of pathology* 1:23-61.

Hernandez, N., 1. Melki, H. Jing, T. Habib, S. S. Y. Huang, J. Danielson, T. Kula, S. Drutman, S. Belkaya, V. Rattina, L. Lorenzo-Diaz, A. Boulai, Y. Rose, N. Kitabayashi, M. P. Rodero, C. Dumaine, S. Blanche, M. N. Lebras, M. C. Leung, L. S. Mathew, B. Boisson, S. Y. Zhang, S. Boisson-Dupuis, S. Giliani, D. Chaussabel, L. D. Notarangelo, S. J. Elledge, M. J. Ciancanelli, L. Abel, Q. Zhang, N. Marr, Y. J. Crow, H. C. Su, and J. L. Casanova. 2018. Life-threatening influenza pneumonitis in a child with inherited IRF9 deficiency. *The Journal of experimental medicine*

Ishiyama, K., H. Ohdan, M. Ohira, H. Mitsuta, K. Arihiro, and T. Asahara. 2006. Difference in cytotoxicity against hepatocellular carcinoma between liver and periphery natural killer cells in humans. *Hepatology* 43:362-372.

Itan, Y., L. Shang, B. Boisson, M. J. Ciancanelli, J. G. Markle, R. Martinez-Barricarte, E. Scott, I. Shah, P. D. Stenson, J. Gleeson, D. N. Cooper, L. *Quintana*-Murci, S. Y. Zhang, L. Abel, and J. L. Casanova. 2016. The mutation significance cutoff: gene-level thresholds for variant predictions. *Nature methods* 13:109-110.

Itan, Y., L. Shang, B. Boisson, E. Patin, A. Bolze, M. Moncada-Velez, E. Scott, M. J. Ciancanelli, F. G. Lafaille, J. G. Markle, R. Martinez-Barricarte, S. J. de Jong, X. F. Kong, P. Nitschke, A. Belkadi, J. Bustamante, A. Puel, S. Boisson-Dupuis, P. D. Stenson, J. G. Gleeson, D. N. Cooper, L. *Quintana*-Murci, J. M. Claverie, S. Y. Zhang, L. Abel, and J. L. Casanova. 2015. The human gene damage index as a gene-level approach to prioritizing exome variants. *Proceedings of the National Academy of Sciences of the United States of America* 112:13615-13620.

Kaplanski, G. 2018. Interleukin-18: Biological properties and role in disease pathogenesis. *Immunological reviews* 281:138-153.

Kim, H. Y., M. B. Eyheramonho, M. Pichavant, C. Gonzalez Cambaceres, P. Matangkasombut, G. Cervio, S. Kuperman, R. Moreiro, K. Konduru, M. Manangeeswaran, G. J. Freeman, G. G. Kaplan, R. H. DeKruyff, D. T. Umetsu, and S. D. Rosenzweig. 2011. A polymorphism in TIM1 is associated with susceptibility to severe hepatitis A virus infection in humans. *The Journal of clinical investigation* 121:1111-1118.

Kim, J., D. Y. Chang, H. W. Lee, H. Lee, J. H. Kim, P. S. Sung, K. H. Kim, S. H. Hong, W. Kang, J. Lee, S. Y. Shin, H. T. Yu, S. You, Y. S. Choi, I. Oh, D. H. Lee, D. H. Lee, M. K. Jung, K. S. Suh, S. Hwang, W. Kim, S. H. Park, H. J. Kim, and E. C. Shin. 2018. Innate-like Cytotoxic Function of Bystander-Activated CD8(+) T Cells Is Associated with Liver Injury in Acute Hepatitis A. *Immunity* 48:161-173 e165.

Kim, S. H., M. Eisenstein, L. Reznikov, G. Fantuzzi, D. Novick, M. Rubinstein, and C. A. Dinarello. 2000. Structural requirements of six naturally occurring isoforms of the IL-18 binding protein to inhibit IL-18. *Proceedings of the National Academy of Sciences of the United States of America* 97:1190-1195.

Kimura, K., S. Sekiguchi, S. Hayashi, Y. Hayashi, T. Hishima, M. Nagaki, and M. Kohara. 2011. Role of interleukin-18 in intrahepatic inflammatory cell recruitment in acute liver injury. *Journal of leukocyte biology* 89:433-442.

Kircher, M., D. M. Witten, P. Jain, B. J. O'Roak, G. M. Cooper, and J. Shendure. 2014. A general framework for estimating the relative pathogenicity of human genetic variants. *Nature genetics* 46:310-315.

Krizman, D. B., and S. M. Berget. 1993. Efficient selection of 3'-terminal exons from vertebrate DNA. *Nucleic acids research* 21:5198-5202.

Le Bouteiller, P., A. Barakonyi, J. Giustiniani, F. Lenfant, A. Marie-Cardine, M. Aguerre-Girr, M. Rabot, I. Hilgert, F. Mami-Chouaib, J. Tabiasco, L. Boumsell, and A. Bensussan. 2002. Engagement of CD160 receptor by HLA-C is a triggering mechanism used by circulating natural killer (NK) cells to mediate cytotoxicity. *Proceedings of the National Academy of Sciences of the United States of America* 99:16963-16968.

Lebel-Binay, S., A. Berger, F. Zinzindohoue, P. Cugnenc, N. Thiounn, W. H. Fridman, and F. Pages. 2000. Interleukin-18: biological properties and clinical implications. *European cytokine network* 11:15-26.

Lemon, S. M., J. J. Ott, P. Van Damme, and D. Shouval. 2018. Type A viral hepatitis: A summary and update on the molecular virology, epidemiology, pathogenesis and prevention. *Journal of hepatology* 68:167-184.

Liu, M., C. W. Chan, 1. McGilvray, Q. Ning, and G. A. Levy. 2001. Fulminant viral hepatitis: molecular and cellular basis, and clinical implications. *Expert reviews in molecular medicine* 2001:1-19.

MacPhee, P. J., V. J. Dindzans, L. S. Fung, and G. A. Levy. 1985. Acute and chronic changes in the microcirculation of the liver in inbred strains of mice following infection with mouse hepatitis virus type 3. *Hepatology* 5:649-660.

Martinez-Barricarte, R., J. G. Markle, C. S. Ma, E. K. Deenick, N. Ramirez-Alejo, F. Mele, D. Latorre, S. A. Mahdaviani, C. Aytekin, D. Mansouri, V. L. Bryant, F. Jabot-Hanin, C. Deswarte, A. Nieto-Patlan, L. Surace, G. Kerner, Y. Itan, S. Jovic, D. T. Avery, N. Wong, G. Rao, E. Patin, S. Okada, B. Bigio, B. Boisson, F. Rapaport, Y. Seeleuthner, M. Schmidt, A. Ikinciogullari, F. Dogu, G. Tanir, P. Tabarsi, M. R. Bloursaz, J. K. Joseph, A. Heer, X. F. Kong, M. Migaud, T. Lazarov, F. Geissmann, B. Fleckenstein, C. L. Arlehamn, A. Sette, A. Puel, J. F. Emile, E. van de Vosse, L. Quintana-Murci, J. P. Di Santo, L. Abel, S. Boisson-Dupuis, J. Bustamante, S. G. Tangye, F. Sallusto, and J. L. Casanova. 2018. Human IFN-gamma immunity to mycobacteria is governed by both IL-12 and IL-23. *Science immunology* 3:

Murai, K., H. Murakami, and S. Nagata. 1998. Myeloid-specific transcriptional activation by murine myeloid zinc-finger protein 2. *Proceedings of the National Academy of Sciences of the United States of America* 95:3461-3466.

Nielsen, C. M., A. S. Wolf, M. R. Goodier, and E. M. Riley. 2016. Synergy between Common gamma Chain Family Cytokines and IL-18 Potentiates Innate and Adaptive Pathways of N K Cell Activation. *Frontiers in immunology* 7:101.

Nolan, T., R. E. Hands, and S. A. Bustin. 2006. Quantification of mRNA using real-time R T-PCR. *Nature protocols* 1:1559-1582.

Novick, D., S. H. Kim, G. Fantuzzi, L. L. Reznikov, C. A. Dinarello, and M. Rubinstein. 1999. Interleukin-18 binding protein: a novel modulator of the Th1 cytokine response. *Immunity* 10:127-136.

Okamura, H., K. Nagata, T. Komatsu, T. Tanimoto, Y. Nukata, F. Tanabe, K. Akita, K. Torigoe, T. Okura, S. Fukuda, and et al. 1995. A novel costimulatory factor for gamma interferon induction found in the livers of mice causes endotoxic shock. *Infection and immunity* 63:3966-3972.

Picard, C., H. Bobby Gaspar, W. A I-Herz, A. Bousfiha, J. L. Casanova, T. Chatila, Y. J. Crow, C. Cunningham-Rundles, A. Etzioni, J. L. Franco, S. M. Holland, C. Klein, T. *Morio*, H. D. Ochs, E. Oksenhendler, J. Puck, M. L. K. Tang, S. G. Tangye, T. R. Torgerson, and K. E. Sullivan. 2018. International Union of Immunological Societies: 2017 Primary Immunodeficiency Diseases Committee Report on Inborn Errors of Immunity. *Journal of clinical immunology* 38:96-128.

Regateiro, F. S., S. Belkaya, N. Neves, S. Ferreira, P. Silvestre, S. Lemos, M. Venancio, J. L. Casanova, I. Goncalves, E. Jouanguy, and L. Diogo. 2017. Recurrent elevated liver transaminases and acute liver failure in two siblings with novel bi-allelic mutations of NBAS. *European journal of medical genetics* 60:426-432.

Sasbon, J. S., D. Buamscha, S. Gianivelli, O. Imventarza, D. Devictor, R. Moreiro, C. Cambaceres, G. Salip, M. Ciocca, M. Cuarterolo, S. Vladimirsky, L. Otegui, R. Castro, L. Brajterman, S. Soto, J. Gonzalez, and M. S. Munne. 2010. Clinical implications of hepatitis A virus ribonucleic acid detection and genotyping in acute liver failure in children in Argentina. *Pediatric critical care medicine: a Journal of the Society of Critical Care Medicine and the World Federation of Pediatric Intensive and Critical Care Societies* 11:385-389.

Scotto-Lavino, E., G. Du, and M. A. Frohman. 2006. 3' end cDNA amplification using classic RACE. *Nature protocols* 1:2742-2745.

Shao, X., Y. Qian, C. Xu, B. Hong, W. Xu, L. Shen, C. Jin, Z. Wu, X. Tong, and H. Yao. 2013. The protective effect of intrasplenic transplantation of Ad-IL-18B P/IL-4 gene-modified fetal hepatocytes on ConA-induced hepatitis in mice. *PloS one* 8:e58836.

Shimada, A. 1996. PCR-based site-directed mutagenesis. *Methods in molecular biology* 57:157-165.

Shinoda, M., G. Wakabayashi, M. Shimazu, H. Saito, K. Hoshino, M. Tanabe, Y. Morikawa, S. Endo, H. Ishii, and M. Kitajima. 2006. Increased serum and hepatic tissue levels of interleukin-18 in patients with fulminant hepatic failure. *Journal of gastroenterology and hepatology* 21:1731-1736.

Somanchi, S. S., K. J. McCulley, A. Somanchi, L. L. Chan, and D. A. Lee. 2015. A Novel Method for Assessment of Natural Killer Cell Cytotoxicity Using Image Cytometry. *PloS one* 10:e0141074.

Son, Y. I., R. M. Dallal, R. B. Mailliard, S. Egawa, Z. L. Jonak, and M. T. Lotze. 2001. Interleukin-18 (IL-18) synergizes with IL-2 to enhance cytotoxicity, interferon-gamma production, and expansion of natural killer cells. *Cancer research* 61:884-888.

Tsutsui, H., K. Matsui, H. Okamura, and K. Nakanishi. 2000. Pathophysiological roles of interleukin-18 in inflammatory liver diseases. *Immunological reviews* 174: 192-209.

Ushio, S., M. Namba, T. Okura, K. Hattori, Y. Nukada, K. Akita, F. Tanabe, K. Konishi, M. Micallef, M. Fujii, K. Torigoe, T. Tanimoto, S. Fukuda, M. Ikeda, H. Okamura, and M. Kurimoto. 1996. Cloning of the cDNA for human IFN-gamma-inducing factor, expression in *Escherichia coli*, and studies on the biologic activities of the protein. *Journal of immunology* 156:4274-4279.

Veenstra, K. G., Z. L. Jonak, S. Trulli, and J. A. Gollob. 2002. IL-12 induces monocyte IL-18 binding protein expression via IFN-gamma. *Journal of immunology* 168: 2282-2287.

Wege, H., S. Siddell, and V. ter Meulen. 1982. The biology and pathogenesis of coronaviruses. *Current topics in microbiology and immunology* 99:165-200.

Yalniz, M., H. Ataseven, S. Celebi, O. K. Poyrazoglu, N. Sirma, and I. H. Bahceitoglu. 2005. Two siblings with fulminant viral hepatitis A: case report. *Acta medica* 48:173-175.

Yoshida, Y., Y. Okada, A. Suzuki, K. Kakisaka, Y. Miyamoto, A. Miyasaka, Y. Takikawa, T. Nishizawa, and H. Okamoto. 2017. Fatal acute hepatic failure in a family infected with the hepatitis A virus subgenotype 1B: A case report. *Medicine* 96:e7847.

Yumoto, E., T. Higashi, K. Nouso, H. Nakatsukasa, K. Fujiwara, T. Hanafusa, Y. Yumoto, T. Tanimoto, M. Kurimoto, N. Tanaka, and T. Tsuji. 2002. Serum gamma-interferon-inducing factor (IL-18) and IL-10 levels in patients with acute hepatitis and fulminant hepatic failure. *Journal of gastroenterology and hepatology* 17:285-294.

Example 2

IL-10RB Mutation in a Multiplex Family with Fulminant Hepatitis Due to Hepatitis A Virus In studies in line with those undertaken in Example 1, we evaluated a distinct family with fulminant viral hepatitis. In this family, a mutation in the IL-10 Receptor B (IL-10RB), was identified and associated with FVH in the patients of the family.

Interleukin 10 receptor, beta subunit (IL-10 RB) is a subunit for the interleukin-10 receptor, also designated IL-10 Receptor subunit 2 (IL10R2) and cluster differentiation antigen CD Ag CDw210b. IL-10RB has the GeneID 3588 and UnitprotKB/SwissProt identifier Q08334. IL-10RB protein amino acid sequence (SEQ ID NO: HGNC 5965 or NP_000619.3) is provided below. The IL-10RB protein belongs to the cytokine receptor family and is an accessory chain essential for the active interleukin 10 receptor complex. Coexpression of IL-10RB and IL-10 receptor subunit 1 protein (also denoted TL-10RA) is required for IL10-induced signal transduction.

Familial segregation with IL-10RB segregation is depicted in FIG. 10. In FIG. 10A, the black-filled symbol indicates the patients P1 and P2, who both died of FVH. In patient 2, it was confirmed that the patient had a single nucleotide substitution by Sanger sequencing (FIG. 10B). This mutation was designated IL-10RB W100G or W100 and is a missense mutation resulting in a Tryptophan to Glycine single amino acid substitution mutation at amino acid 100 in the IL-10RB protein.

Figure 10B:
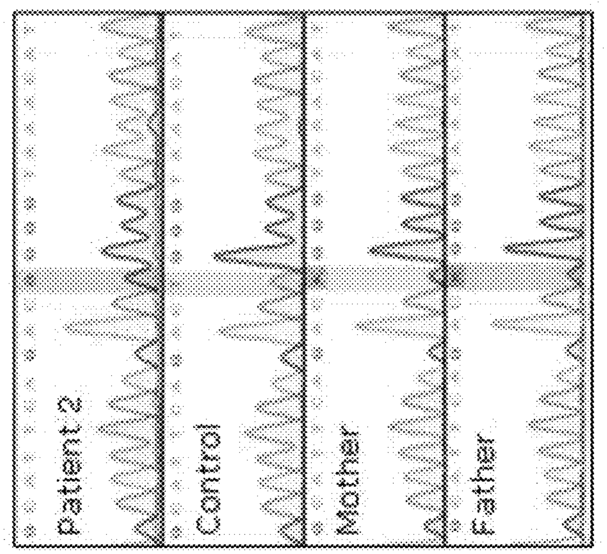
FIG. 10A to FIG. 10D. Homozygous mutation in a multiplex family with fulminant hepatitis due to Hepatitis A virus. (A) Familial segregation with IL10RB segregation. The black-filled symbol indicates the patients. (B) Confirmation of the single nucleotide substitution by Sanger sequencing. (C) Population genetics of homozygous coding missense homozygous loss-of-function IL10RB mutations taken from GnomAD and previous reported loss-of-function IL10RB mutations. The patients' variant is rare and shown in red X. (D) Schematic diagram of IL-10RB protein and the location of pathogenic mutations.
Figure 10A:
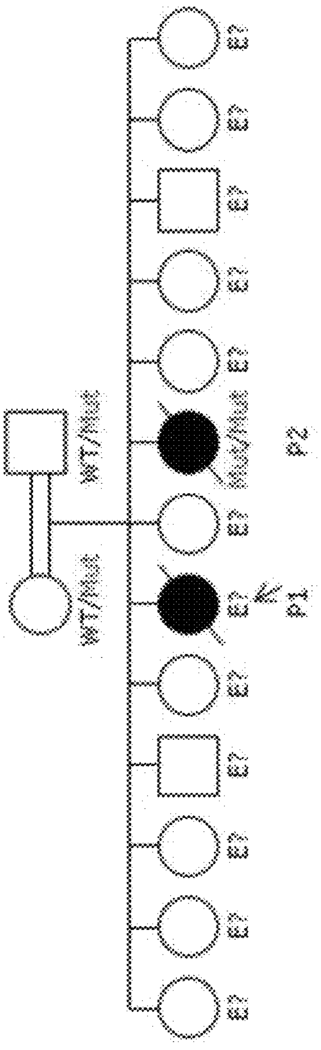
Figure 10C:
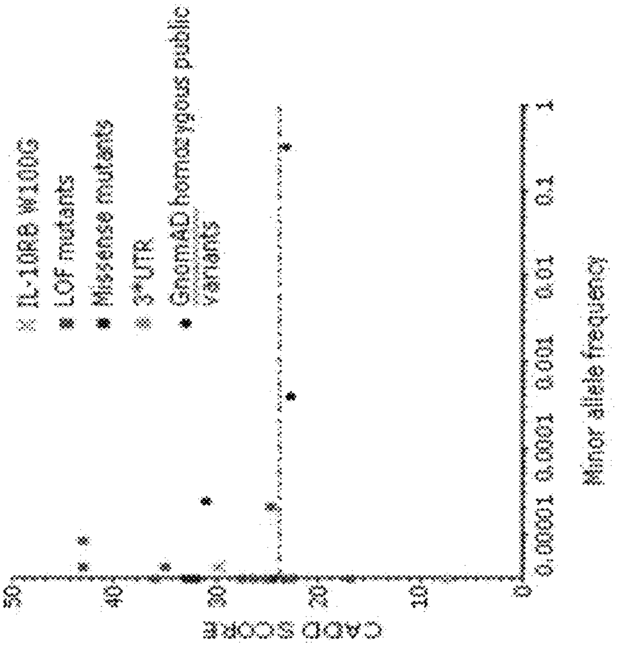
Figure 10D:
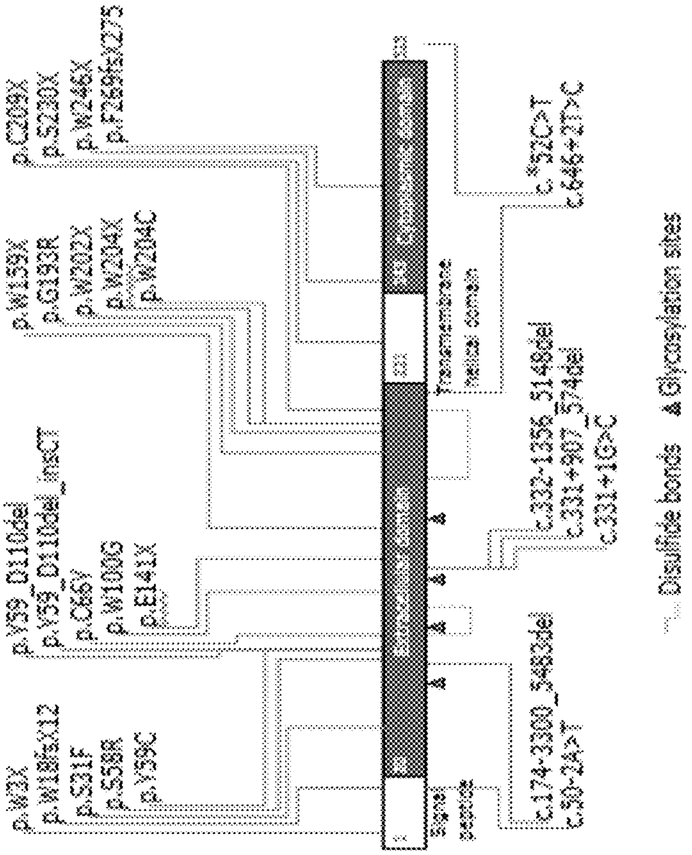

We evaluated population genetics of homozygous coding missense, homozygous loss-of-function IL-10RB mutations taken from GnomAD and previous reported loss-of-function IL-10RB mutations (FIG. 10C). The patients' variant is rare. The location of various pathogenic mutations in the IL-10RB protein are depicted schematically in FIG. 10D. IL-10RB protein is comprised of a signal peptide, extracellular domain, transmembrane helical domain and a cytoplasmic domain. The W100G mutation is located in the extracellular domain of the 325 amino acid IL-10RB protein.

The IL-10RB amino acid sequence (NCBI Ref sequence NP_000619.3) (SEQ ID NO:2) is provided below. The Tryptophan and W100 site of the W100G mutation is in bold and underlined. DNA sequence for IL-10RB human is known (NCBI Ref sequence NG_012089.1)

```
        10         20         30
MAWSLGSWLG GCLLVSALGM VPPPENVRMN

        40         50         60
SVNFKNILQW ESPAFAKGNL TFTAQYLSYR

        70         80         90
IFQDKCMNTT LTECDFSSLS KYGDHTLRVR

       100        110        120
AEFADEHSDW VNITFCPVDD TIIGPPGMQV

       130        140        150
EVLADSLHMR FLAPKIENEY ETWTMKNVYN

       160        170        180
SWTYNVQYWK NGTDEKFQIT PQYDFEVLRN

       190        200        210
LEPWTTYCVQ VRGFLPDRNK AGEWSEPVCE

       220        230        240
QTTHDETVPS WMVAVILMAS VFMVCLALLG

       250        260        270
CFALLWCVYK KTKYAFSPRN SLPQHLKEFL

       280        290        300
GHPHHNTLLF FSFPLSDEND VFDKLSVIAE

       310        320
DSESGKQNPG DSCSLGTPPG QGPQS
```

Individuals and patients previously reported to carry IL-10RB mutations and their particular mutations are depicted below in Table 8.

TABLE 8

IL-10RB Patients Carrying at Least One Missense Mutation

| Mutation | Number of patients | Molecular mechanism | Patients' country of origin | Onset of disease (days) | References |
|---|---|---|---|---|---|
| S31F | 1 | Homozygous | Iran | 60 | Yazdani, 2019 |
| S58R | 1 | Compound heterozygous | USA | <30 | Shouval, 2014; Shouval, 2017 |
| Y59C | 1 | Homozygous | Italy | 14 | Neven, 2013; Pigneur, 2013 |
| C66Y | 1 | Homozygous | Bangladesh France/ Saudi | 45 | Kotlartz, 2012 |

TABLE 8-continued

| IL-10RB Patients Carrying at Least One Missense Mutation | | | | | |
|---|---|---|---|---|---|
| Mutation | Number of patients | Molecular mechanism | Patients' country of origin | Onset of disease (days) | References |
| W100G | 2 | Homozygous | Arabia | 84/? | Pigneur, 2013 |
| G193R | 1 | Homozygous | Turkey | 10 | Engelhardt, 2013 |
| W204C | 2 | Compound heterozygous/ Homozygous | France/ China | 14/? | Neven, 2013; Pigneur, 2013; Gong, 2019 |

Figure 11B:
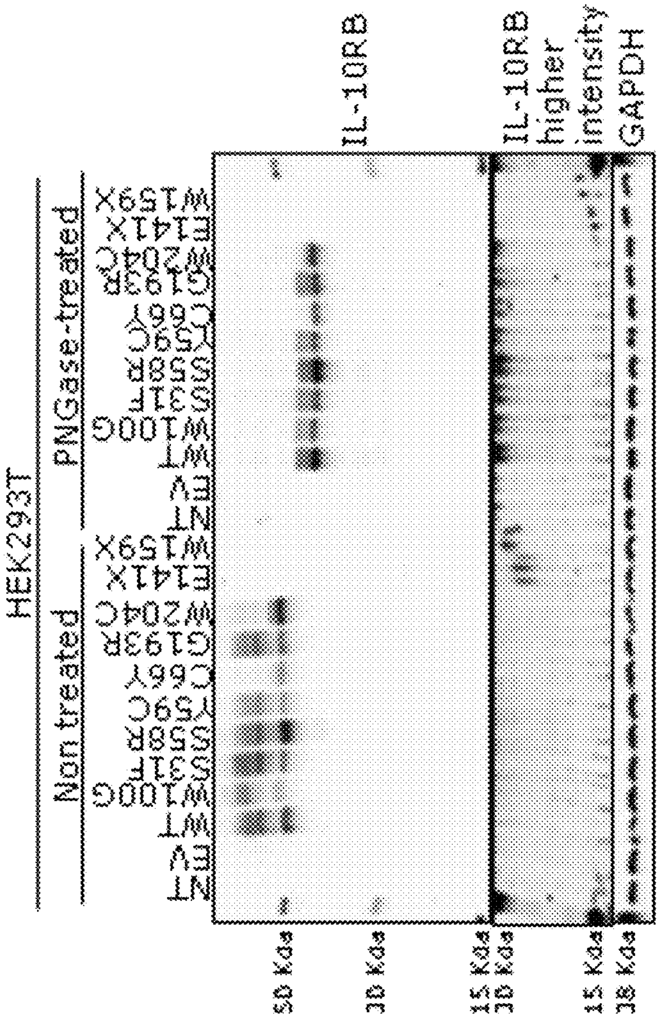
FIG. 11A to FIG. 11G. Functional characterization of missense mutations reported in IL10RB in response to IL-10, IL-22, and IL-29 stimulation in overexpression system. (A) qPCR results from HEK293T cells transfected 24 hours with the indicated IL10RB alleles. Stop gain alleles were used as negative controls for each of B and C. Expression of the different alleles by Western Blot (B) and Flow cytometry (C) with and without PNGase treatment (B). (D-G) depict response in terms of phosphorylation of STAT1 and STAT3 following IL-10 (D), IL22 (E), IL26 (F) and IL29 (G) stimulation in IL-10RB$^{KO}$ SV-40 fibroblasts transfected with the indicated IL10RB alleles and IL10RA-V5 (D), IL22RA1-His (E), IL20RA (F) and IFNLR1-DDK (G) tagged. All stimulation experiments were carried out for 30 minutes, except IL26 where we stimulated 40 min. Cytokine concentration was 100 ng/ml, except for IL-10 where we used 40 ng/ml. EV=empty vector and p=phosphorylated.
Figure 11A:
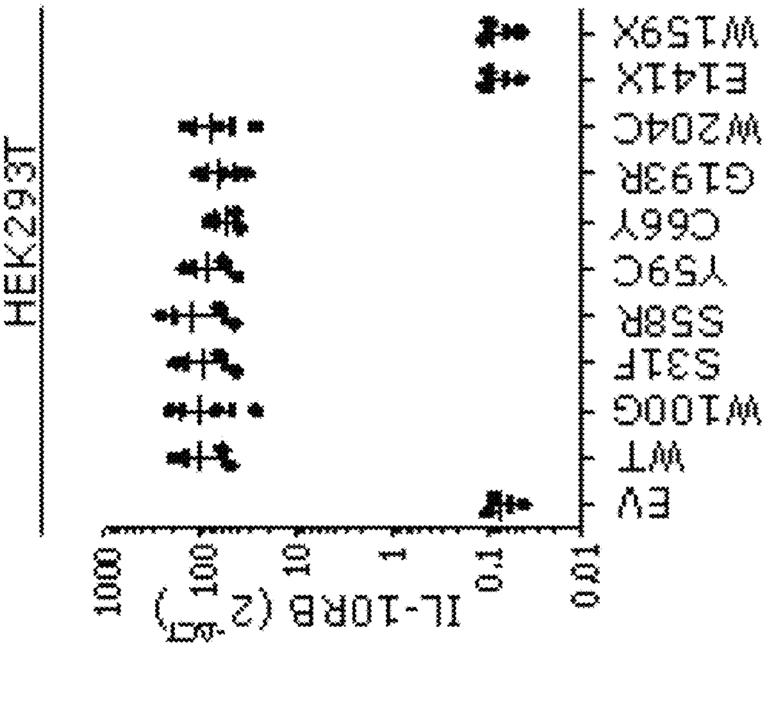
Figure 11D:
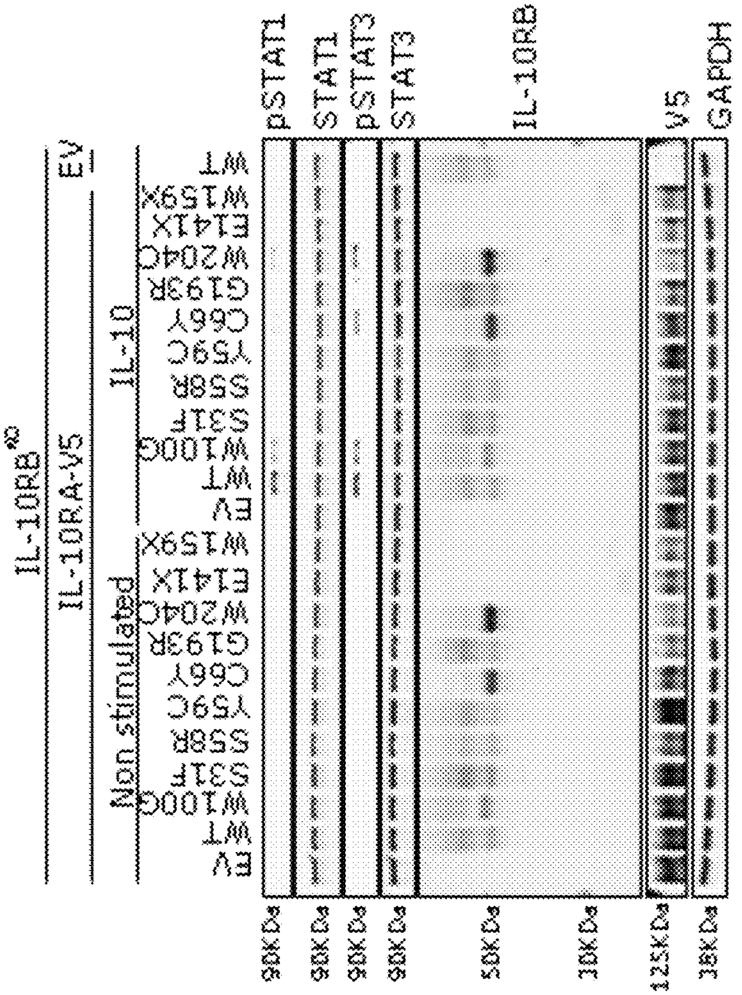
Figure 11C:
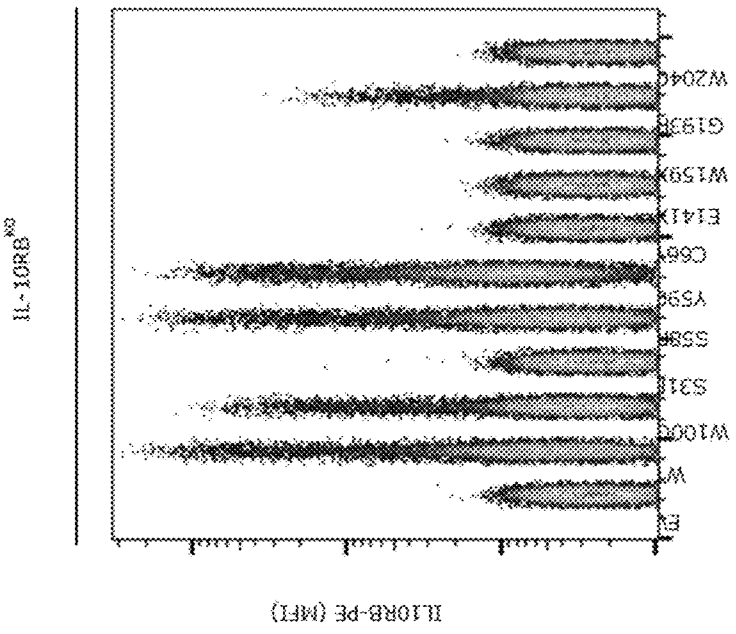
Figure 11E:
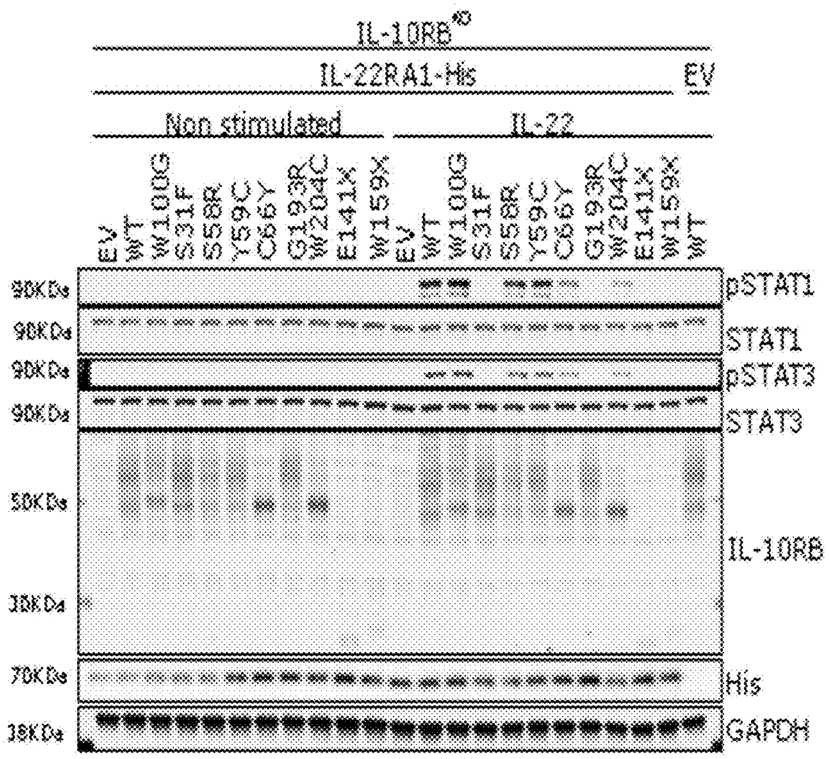
Figure 11F:
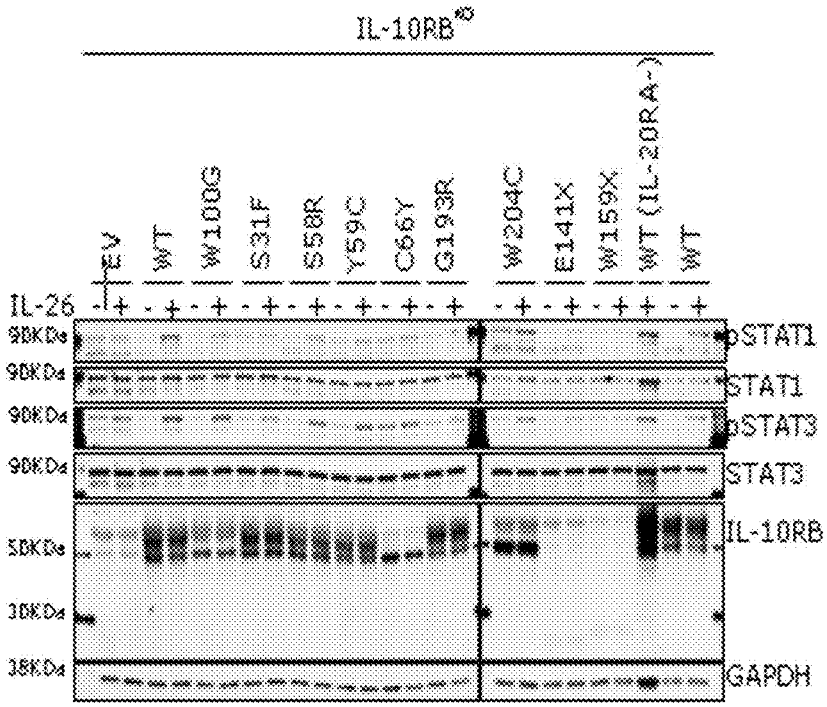
Figure 11G:
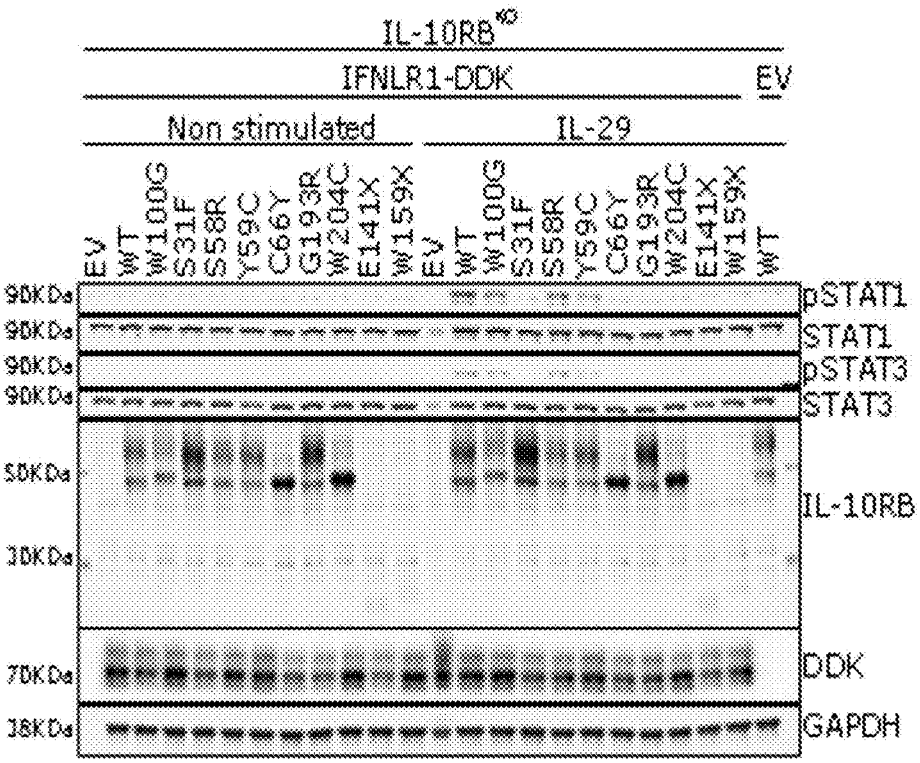

Numerous reported IL-10RB mutations, along with this familial W100G mutation, were evaluated in an expression system. HEK293T cells were transfected with various IL-10RB missense mutation alleles and characterized (FIG. 11). IL-10RB was first evaluated by qPCR (FIG. 11A). Expression of the different alleles was assessed by Western Blot with and without PNGase treatment to deglycosylate the proteins (FIG. 11B) and by flow cytometry (FIG. 11C). Response of the IL-10RB mutants to stimulation with various interleukins was assessed using phosphorylation of STAT1 and STAT3 as a response readout. IL-10RB$^{KO}$ SV-40 fibroblasts were transfected with mutant IL10RB alleles alone or also with IL10RA-V5 (FIG. 11D), IL22RA1-His (FIG. 11E), IL22RA (FIG. 11F) and IFNLR1-DDK (FIG. 11G) and phosphorylation of STAT1 and STAT3 with and without stimulation with IL-10 (FIG. 11D), IL22 (FIG. 11E), IL26 (FIG. 11F) and IL29 (FIG. 11G) was evaluated.

Figure 12A:
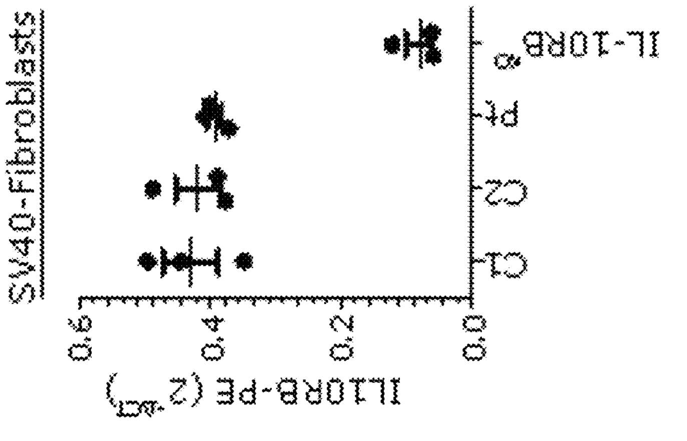
Figure 12B:
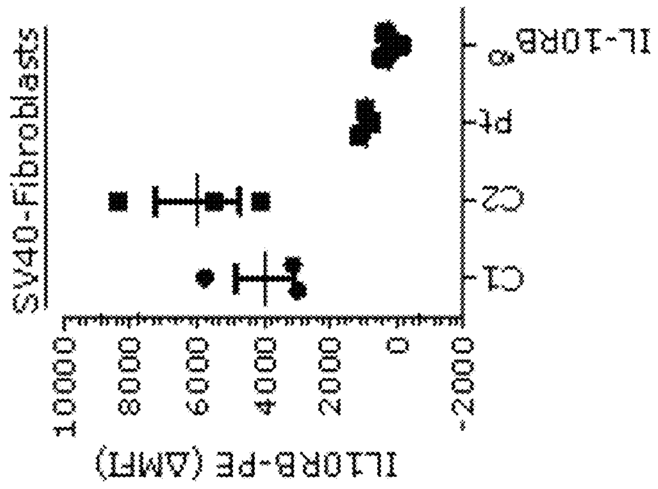
Figure 12D:
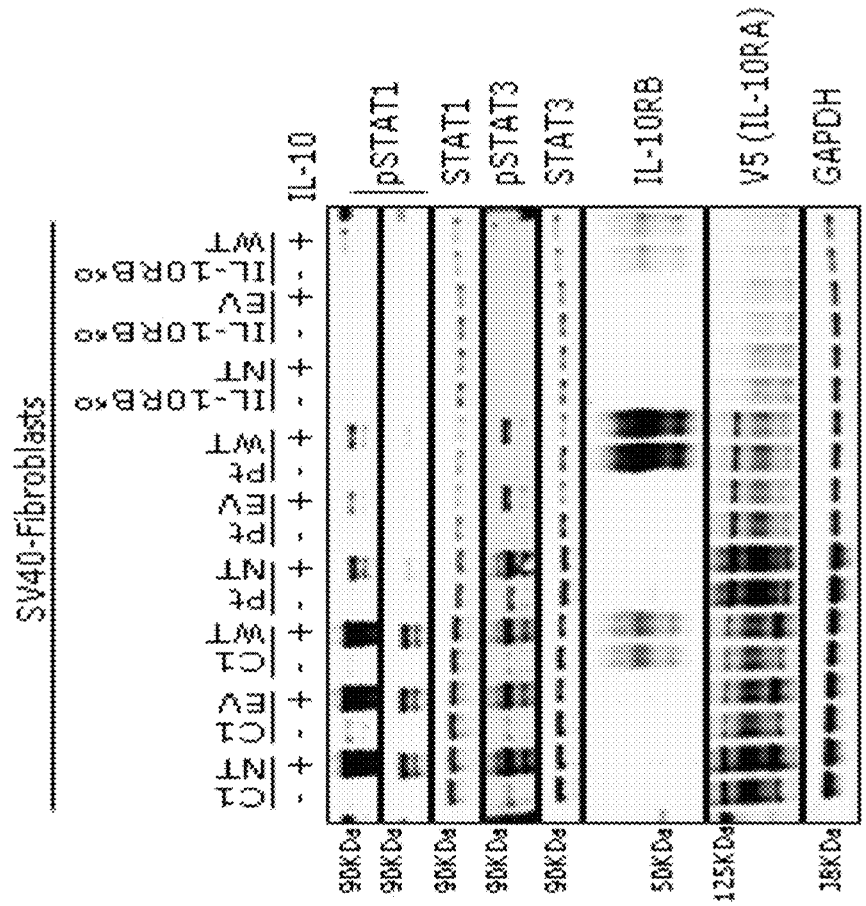
Figure 12C:
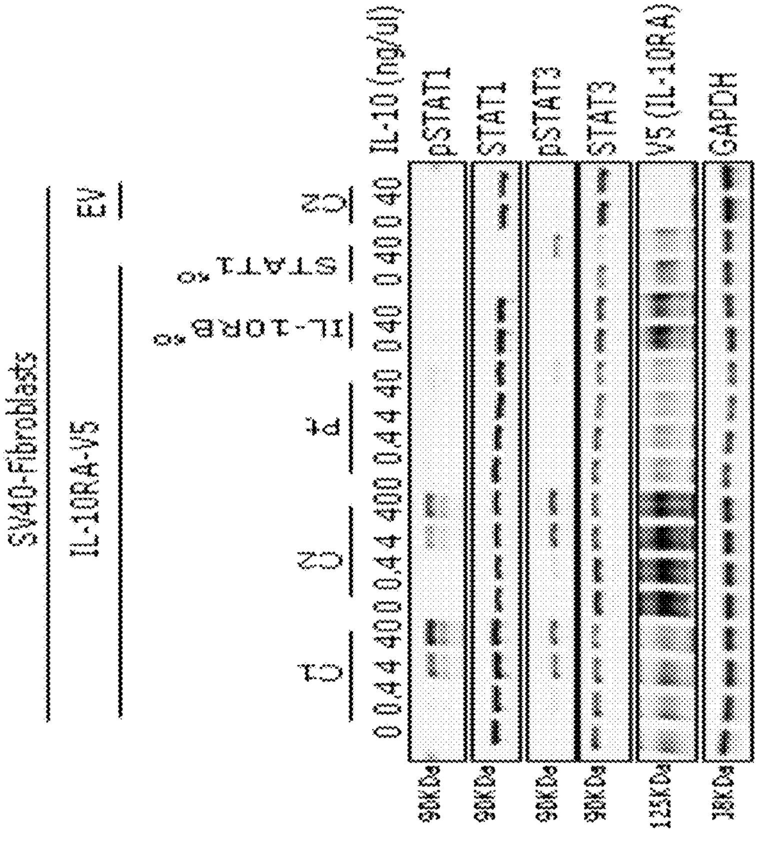
Figure 12E:
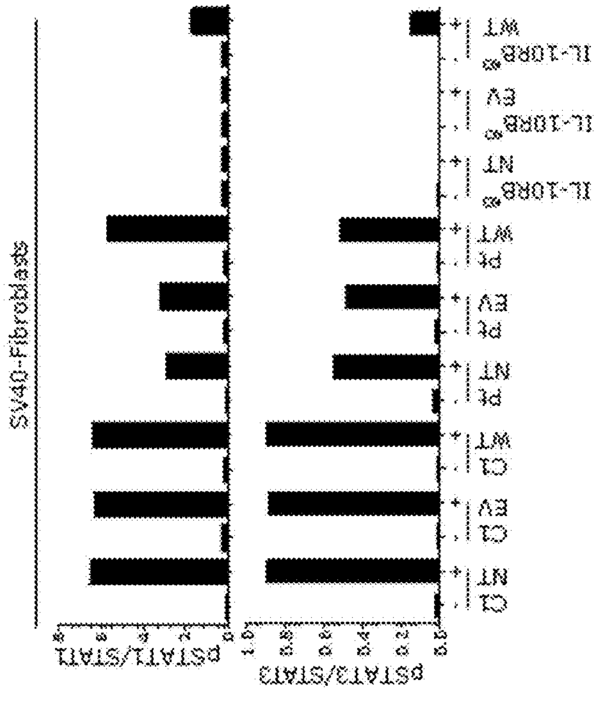
Figure 12F:
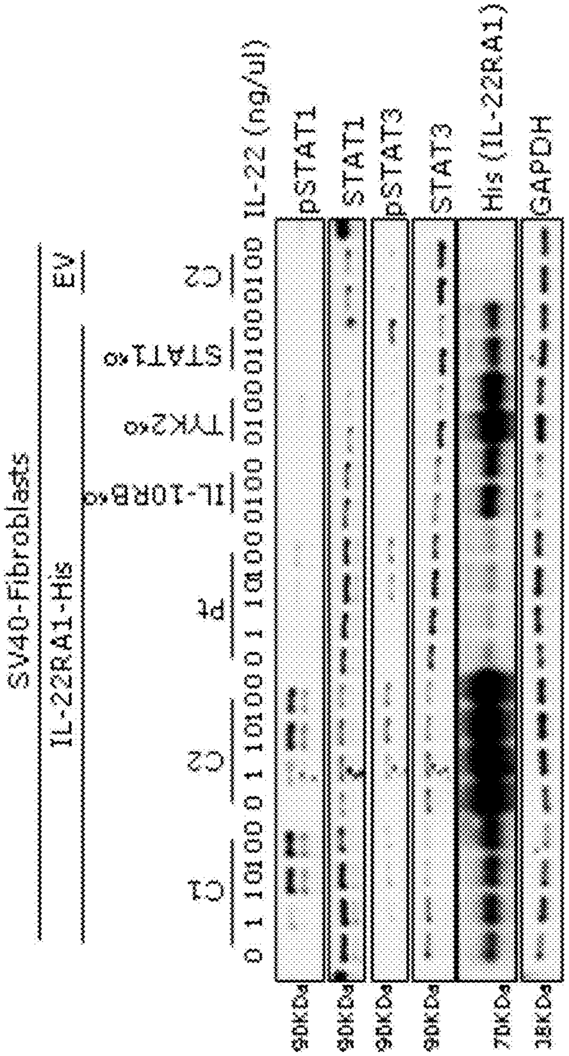
Figure 12H:
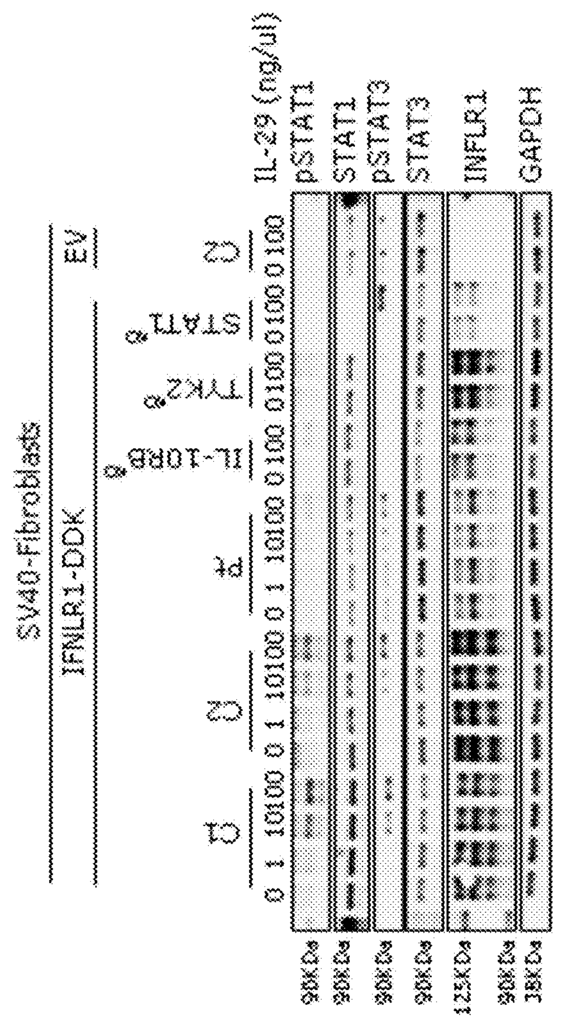
Figure 12G:
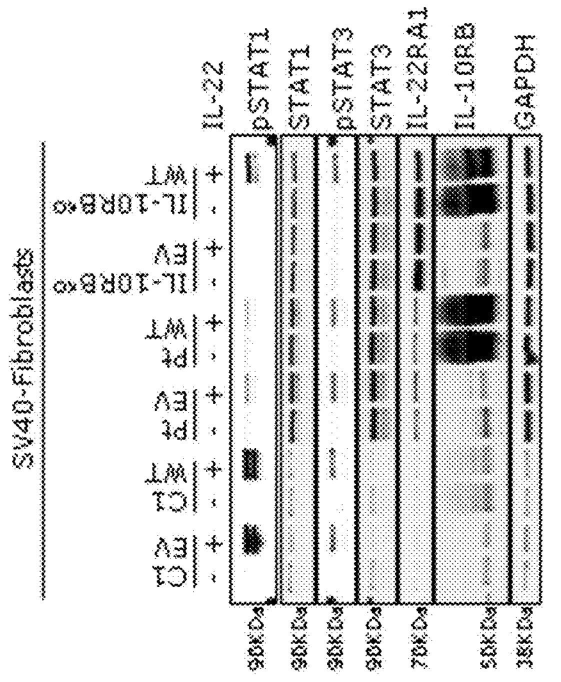
Figure 12I:
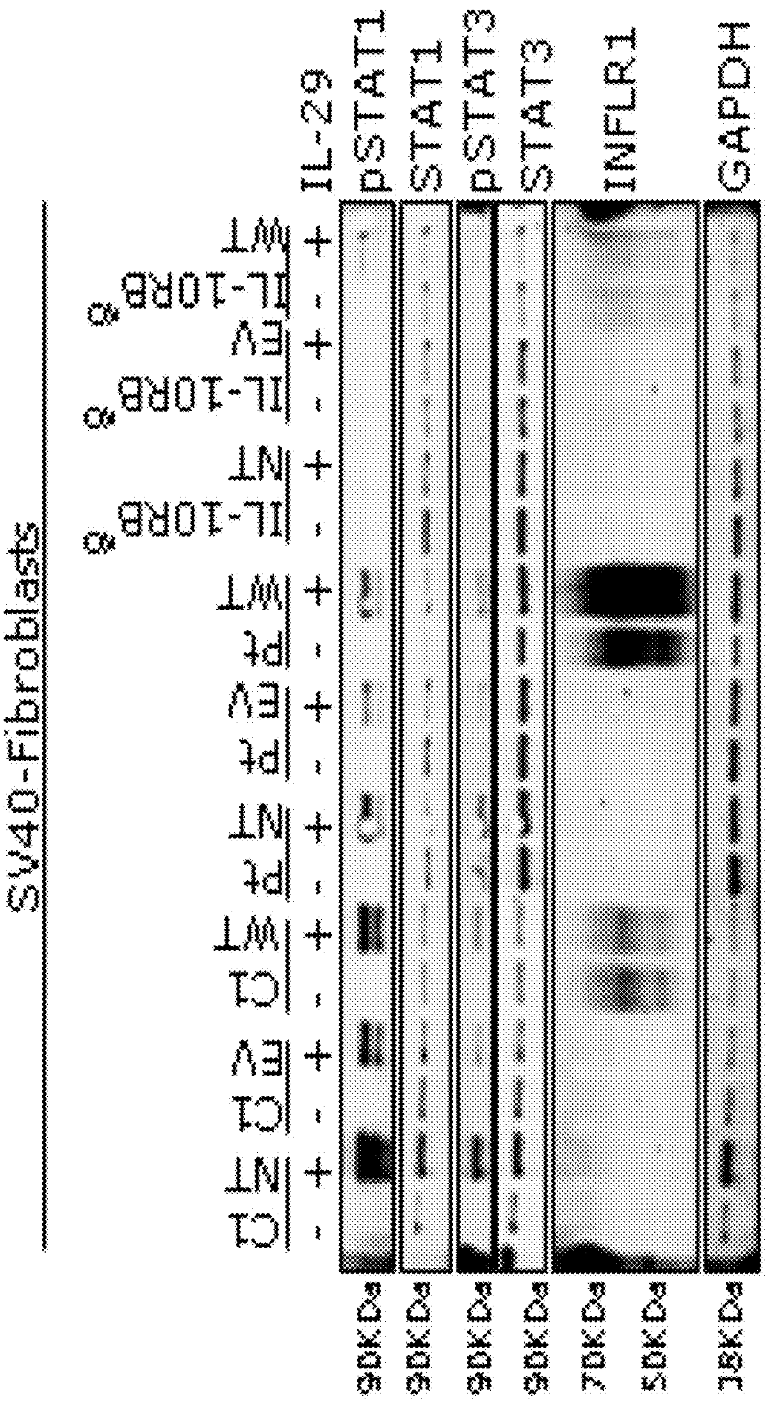

A summary of the overexpression studies is provided in Table 9. The W100G mutant shows normal IL-22 and IL-29 response and altered IL-10 response, wherein STAT3 phosphorylation and SOCS3 expression is near wild type levels after IL-10 stimulation but STAT1 phosphorylation is significantly reduced and CXCL9 expression is not observed with IL-10 stimulation. The IL-10 response pathway is significantly altered with the IL-10RB W100G mutation.

ducted. IL10RB mRNA was measured by qPCR in patient, another IL10RB-deficient patient (IL-10RB$^{KO}$) and control IL-10RB SV40-fibroblasts cells (FIG. 12A). The patient of this study expresses IL-10RB mRNA as assessed by qPCR. IL10RB-deficient patient (IL-10RB$^{KO}$) cells show minimal IL-10RB expression by qPCR. IL-10RB surface expression was evaluated by flow cytometry on patient cells, a IL10RB-deficient patient (IL-10RB$^{KO}$) and controls (FIG. 12B). This patient IL-10RB W100G shows low IL-10RB surface expression and the IL10RB-deficient patient (IL-10RB$^{KO}$) shows essentially no IL-10RB surface expression by flow cytometry. This patient IL-10RB W100G and the IL10RB-deficient patient (IL-10RB$^{KO}$) mutation SV-40 and control fibroblasts were further evaluated using Western blots, with and without IL-10 and IL-22 stimulation. In a first set of studies the patient and control-based cells were further stably transduced with IL-10RA. Response to IL-10 stimulation was evaluated and phosphorylated STAT1 and STAT3 (pSTAT1 and pSTAT3) were assessed (FIG. 12C). Then the patient and control-based cells were complemented with IL10RB-WT and response to IL-10 stimulation was evaluated and phosphorylated STAT1 and STAT3 were assessed (FIG. 12D). Quantification of pSTAT1 and pSTAT3 is depicted in FIG. 12E. Patient IL-10RB W100G cells show reduced pSTAT1 and pSTAT3, which are increased by complementation with IL10RB-WT. For the IL10RB-deficient patient (IL-10RB$^{KO}$) essentially no pSTAT1 and pSTAT3 can be quantitated and minimal after complementation with IL10RB-WT. FIGS. 12F-12G depict representative western blot showing IL-22 stimulated patient and control cells stably transduced with IL10RA (FIG. 12F), and complemented with IL10RB-WT (FIG. 12G). Patient IL-10RB W100G cells show pSTAT3 with increased IL-22. Phosphorylated STAT1 and STAT3 were assessed after IL-29 stimulation of patient and control cells either stably transduced with IFNLR1 (FIG. 12H), or complemented with IL10RB-WT (FIG. 12I). Patient IL-10RB W100G cells show pSTAT1 with increased IL-29.

TABLE 9

| Summary of results on the overexpression system | | | | | | | | | | | |
|---|---|---|---|---|---|---|---|---|---|---|---|
| | | IL10RB overexpression system | | | | | | | | | |
| Stimulation | Read out | WT | W100G | S31F | S58R | Y59C | C66Y | S193R | W204C | E141X | W159X |
| IL10 | WB-pSTAT1 | +++ | + | – | – | – | + | – | + | – | – |
| | WB-pSTAT3 | +++ | +++ | – | – | – | +++ | – | +++ | – | – |
| | qPCR-CXCL9 | +++ | – | ND | ND | – | ND | ND | ND | – | – |
| | qPCR-SOCS3 | +++ | +++ | ND | ND | – | ND | ND | ND | – | – |
| IL22 | WB-pSTAT1 | +++ | +++ | – | +++ | +++ | + | – | + | – | – |
| | WB-pSTAT3 | +++ | +++ | – | +++ | +++ | + | – | + | – | – |
| | qPCR-CXCL9 | +++ | +++ | – | +++ | +++ | + | – | + | – | – |
| IL29 | WB-pSTAT1 | +++ | +++ | – | +++ | ++ | + | – | + | – | – |
| | WB-pSTAT3 | +++ | +++ | – | +++ | ++ | + | – | + | – | – |
| | qPCR-CXCL9 | +++ | +++ | – | +++ | + | + | – | + | – | – |

Figure 13B:
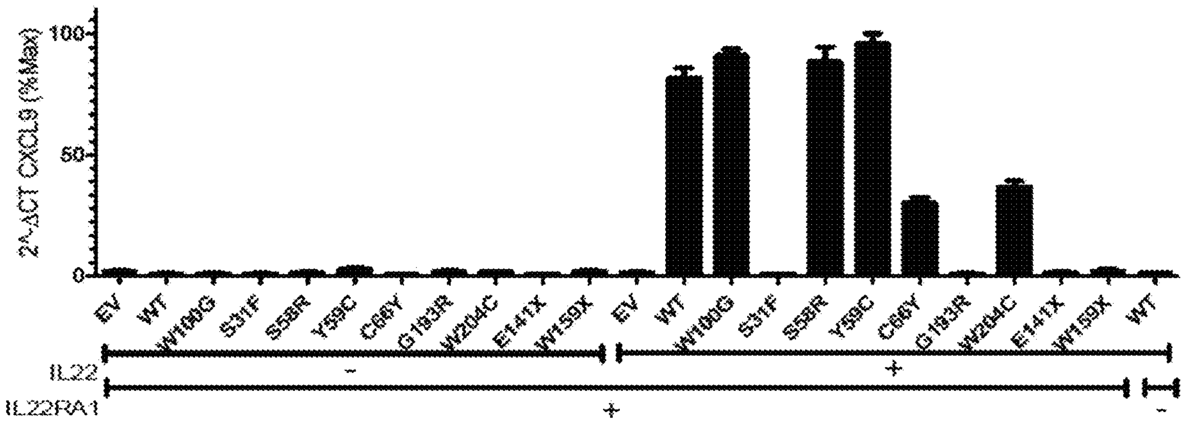
Figure 13C:
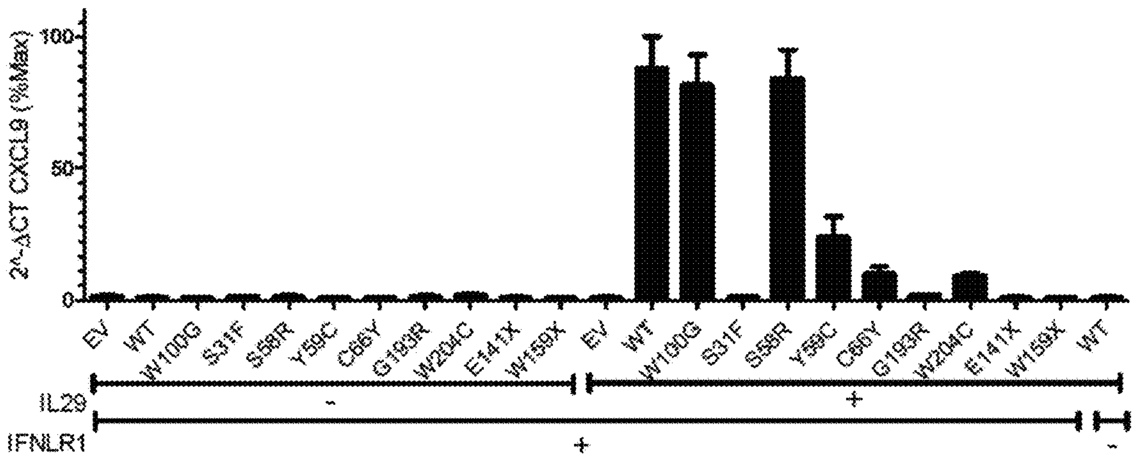
Figure 14A:
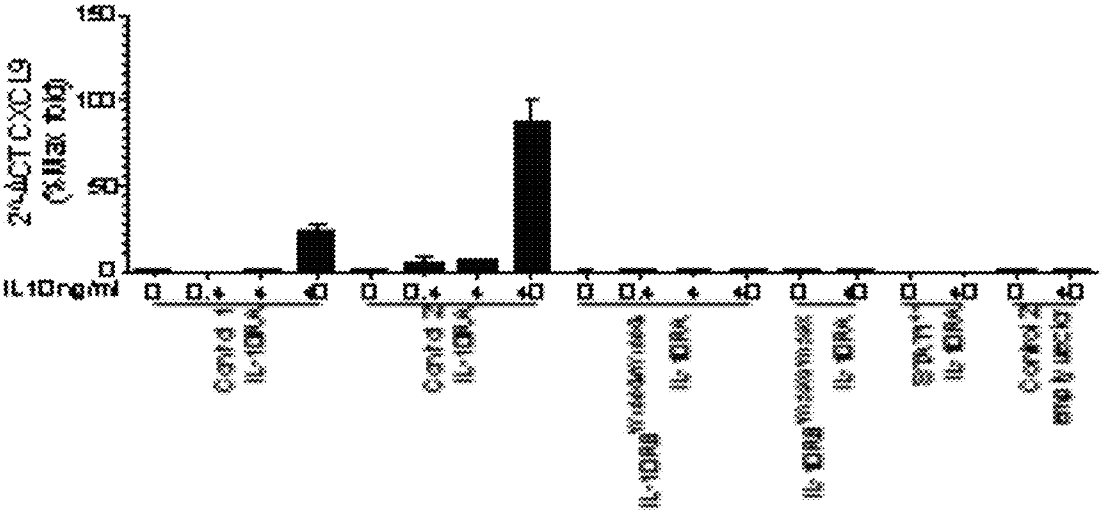
FIG. 14A to FIG. 14E. Transcription levels of CXCL9 and/or IL10RB and/or IL-22RA assessed by qRT-PCR on control cells, patient cells and IL10RB$^{KO}$ cells, transduced with an empty or IL10RB-WT vector and treated with IL10, IL22 or IL29. (A) depicts levels of CXCL9 for cells treated with IL-10; (B) depicts levels of CXCL9 and IL10RB for cells treated with IL-10; (C) depicts levels of CXCL9 and IL-22RA for cells treated with IL-22; (D) depicts levels of CXCL9 and IL10RB for cells treated with IL-22; (E) depicts levels of CXCL9 and IL10RB for cells treated with IL-29.
Figure 14B:
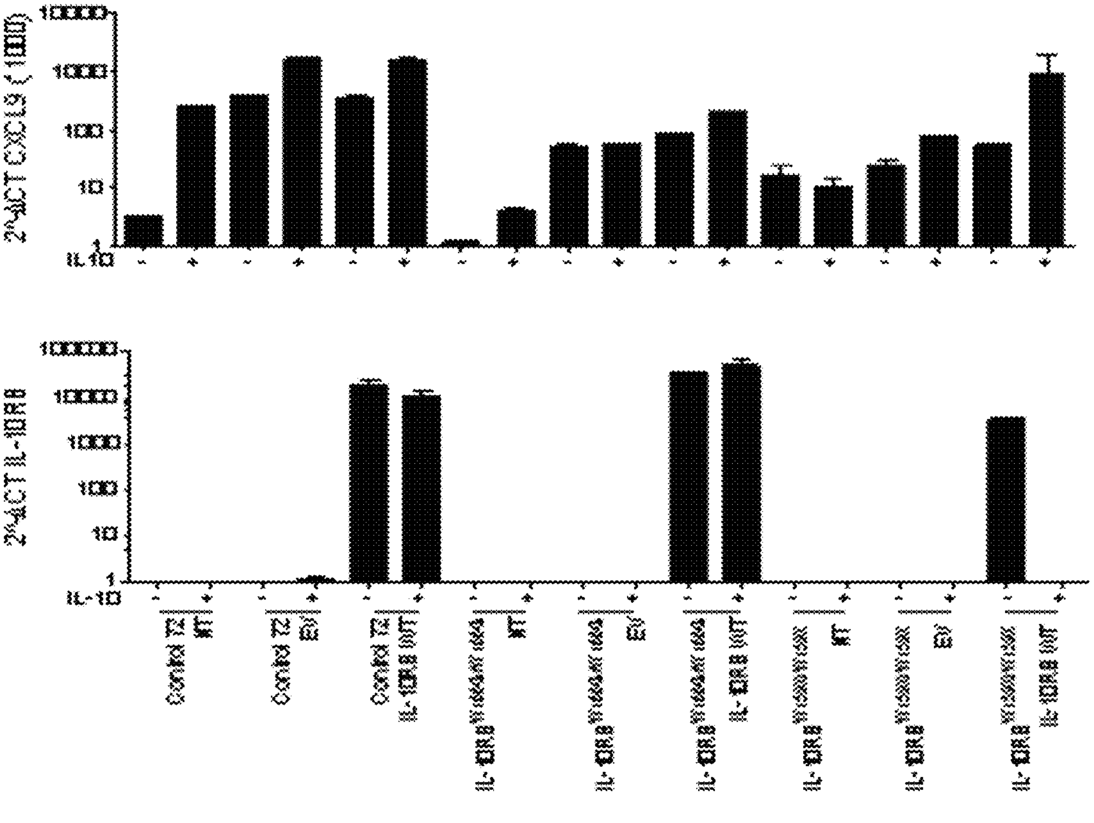
Figure 14C:
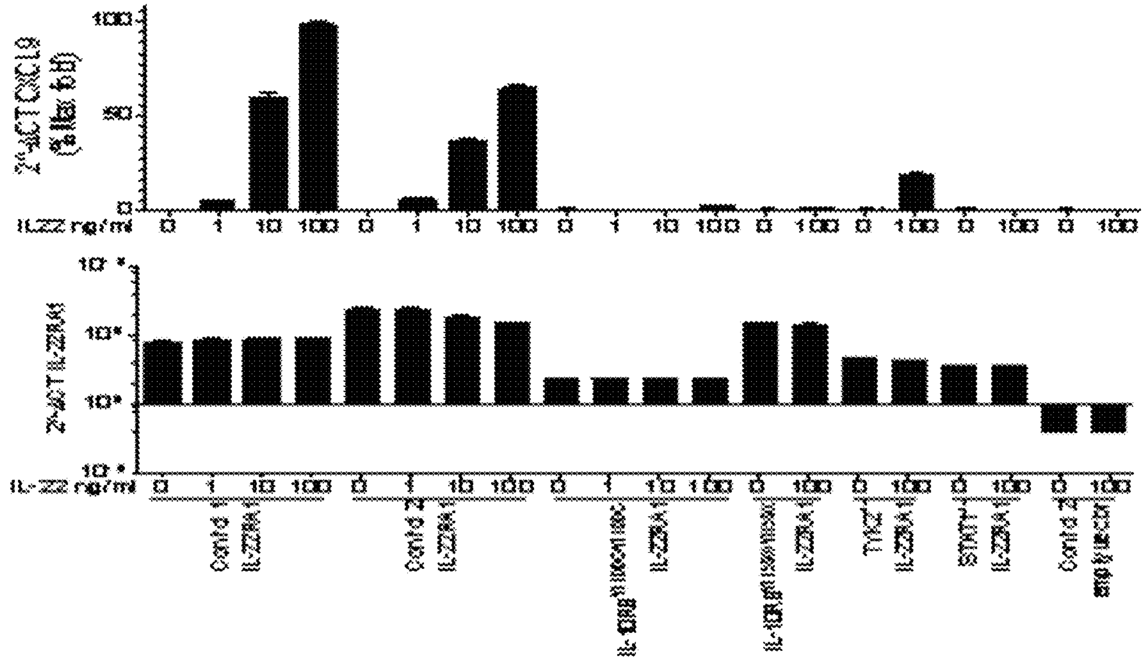
Figure 14D:
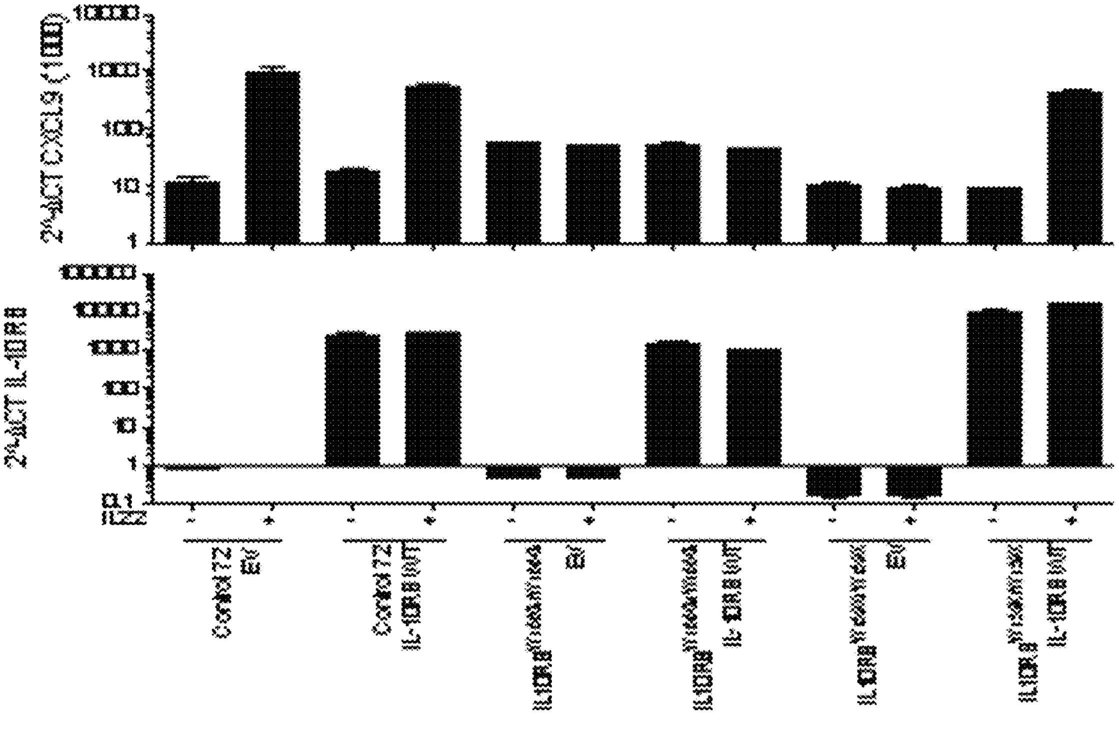
Figure 14E:
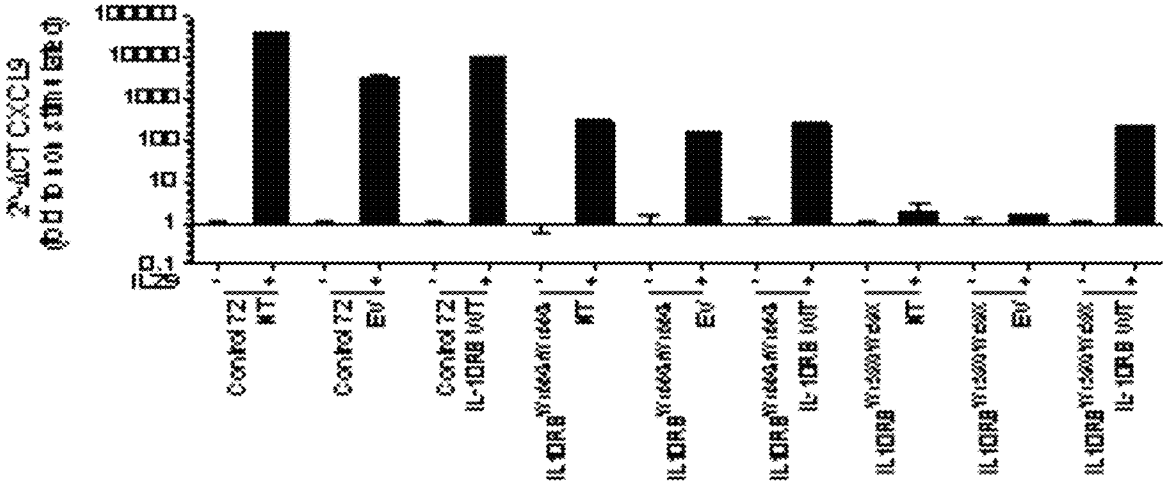
Figure 14F:
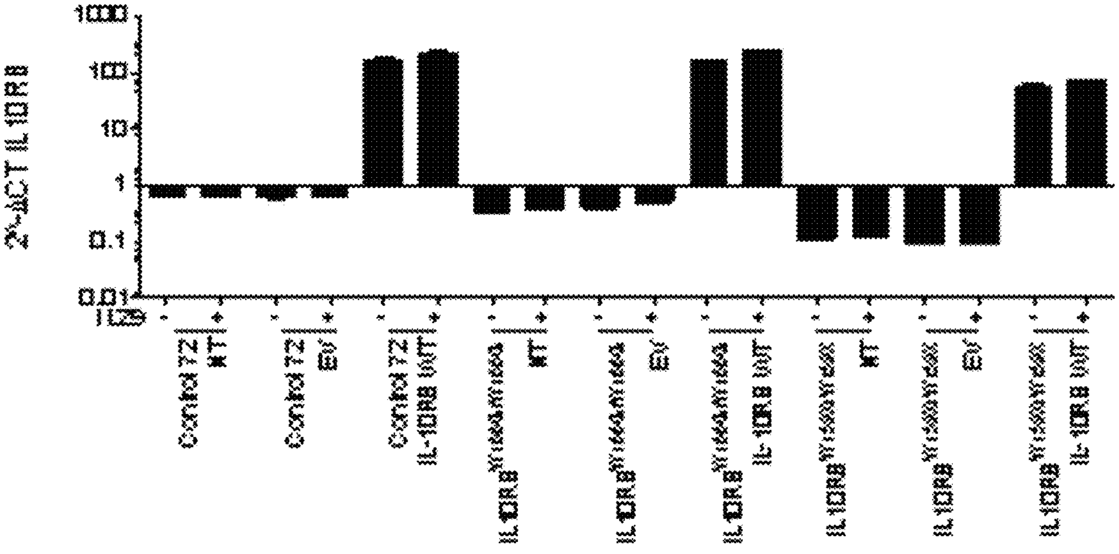

Further characterization of the instant W100G mutation and other reported IL10RB missense mutations was con- IL-10, IL-22 and IL-29 responses were further evaluated in different mutant alleles of IL-10RB by overexpression experiments. For these studies, IL10RB$^{KO}$ cells were transfected with different mutated alleles of IL10RB. Following treatment with one of the interleukins, CXCL9 or SOCS3 transcription was assessed by qPCR. In FIG. 13A, expression of CXCL9 and SOCS3 was determined with and without IL-10 stimulation on mutant or control cells transduced with IL-10RA. While SCLS3 expression was almost normal in the W100G mutant in contrast to the other mutants, CXCL9 transcription response was significantly reduced/nearly absent after IL-10 stimulation in the W100G mutant, as with the other mutants (FIG. 13A). With IL-22 stimulation of these cells, the W100G mutant, as well as mutants S58R and Y59C showed about normal (WT) levels of CXCL9 transcription (FIG. 13B). The W100G mutant showed similarly significant CXCL9 transcription and effectively near to the level of wild type (WT) CXCL9 transcription with IL-29 stimulation, as did the S58R mutant (FIG. 13C).

In further such studies, the control, patient W100G and IL-10RB$^{KO}$ cells, transduced with an empty or IL-10RB-WT vector were evaluated for response to IL-10, IL-22 or IL-29 treatment. Transcription levels of CXCL9, SOCS3 and IL-10RB were assessed by qPCR (FIG. 14). IL-10RB WT can at least partially complement certain IL-10RB mutants, including patient IL-10RB W100G.

Figure 15:
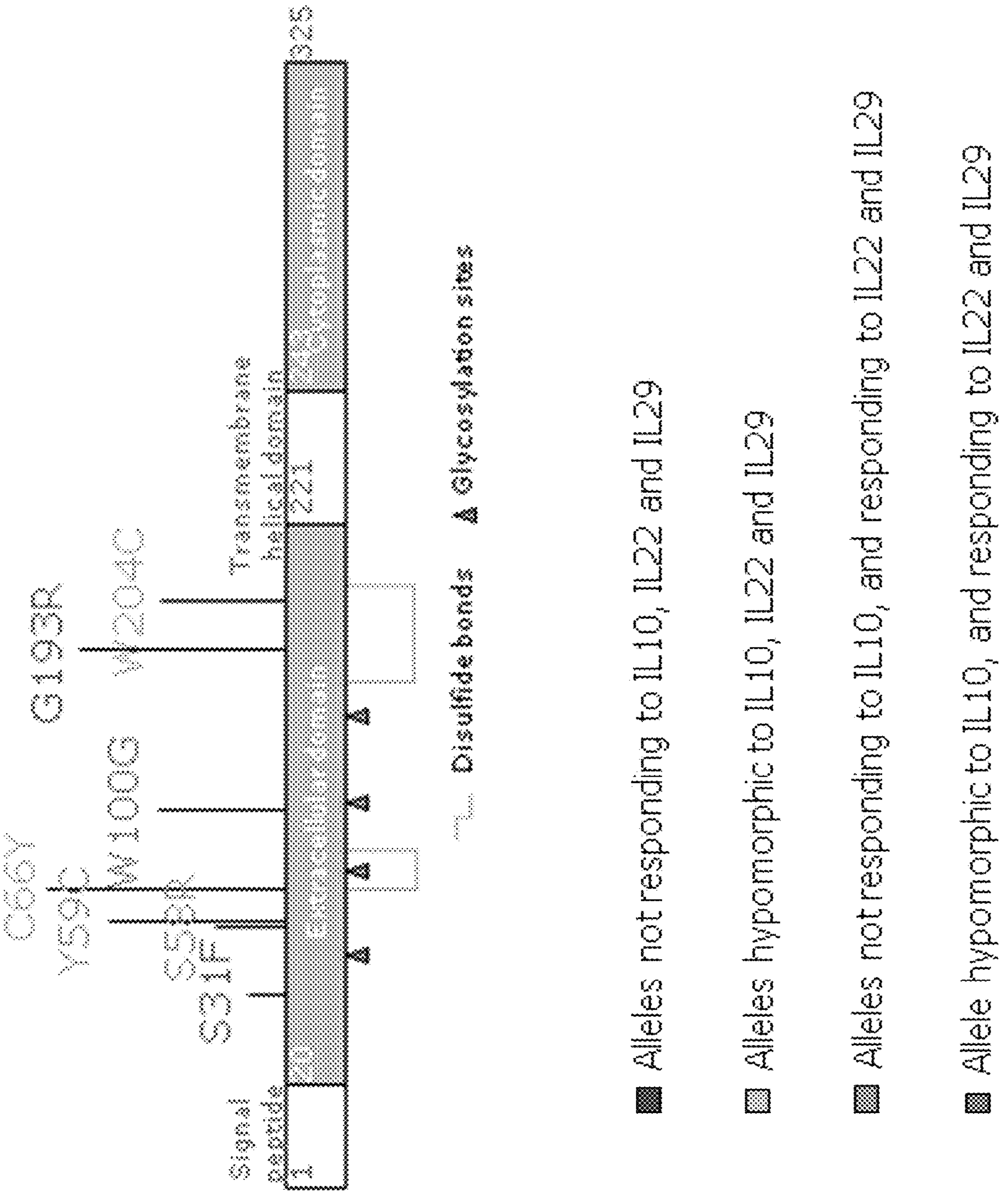
FIG. 15. Schematic representation of missense mutations in IL10RB and their response to the different IL10RB-dependent cytokines in overexpression.

The responses to IL-10, IL-22 and IL-29 of various IL-10RB alleles, mapped to the extracellular domain on the IL-10RB protein, are depicted in FIG. 15. The S31F and G193R alleles do not respond to IL-10, IL-22 and IL-29. The C66Y and W204C alleles are hypomorphic to IL-10, IL-22 and IL-29. Hypomorphic alleles show a partial loss of gene function, such as through reduced protein or RNA expression or reduced functional performance, but not a complete loss. Thus, some but reduced response is demonstrated. The S58R and Y59C alleles do not respond to IL-10 but do respond to IL-22 and IL-29. Uniquely, the patient W100G allele is hypomorphic to IL-10 and responds to IL-22 and IL-29.

These studies demonstrate that fulminant viral hepatitis can result following hepatitis virus infection in a patient or individual harboring mutation of IL-10 Receptor subunit, particularly IL-10RB, such that IL-10 mediated responses are blocked or significantly reduced. The instant patient IL-10 RB W100G mutation leads to altered IL-10 mediated responses, particularly demonstrating failure to generate CXCL9 response and phosphorylation of STAT 1 and STAT3. Altered IL-10 response as provided herein results in an altered and ineffective viral response and leads to fulminant viral hepatitis.

Whole-exome sequencing (WES) of the patient of this study (denoted patient 2) revealed numerous homozygous mutations in this patient, including the IL-10RB W100G mutation, as shown in Table 10.

REFERENCES

Engelhardt, K. R., Shah, N., Faizura-Yeop, I., Kocacik Uygun, D. F., Frede, N., Muise, A. M., Shteyer, E., Filiz, S., Chee, R., Elawad, M., Hartmann, B., Arkwright, P. D., Dvorak, C., Klein, C., Puck, J. M., Grimbacher, B., and E. O. Glocker. 2013. Clinical outcome in IL-10- and IL-10 receptor-deficient patients with or without hematopoietic stem cell transplantation. *Journal of allergy and clinical immunology* 131: 825-830.

Gong, Y. Z., Ning, H. J., Ma, X., Zhu, D., Wang, F. P., Zhang, R., Zhang, Y. L., Zhong, X. M. 2019. [Clinical and genotypic characteristics of infantile inflammatory bowel disease]. *Zhonghua Er Ke Za Zhi* 57: 520-525.

Kotlarz, D., Beier, R., Murugan, D., Diestelhorst, J., Jensen, O., Boztug, K., Pfeifer, D., Kreipe, H., Pfister, E. D., Baumann, U., Puchalka, J., Bohne, J., Egritas, O., Dalgic, B., Kolho, K. L., Sauerbrey, A., Buderus, S., Güngör, T., Enninger, A., Koda, Y. K., Guariso, G., Weiss, B., Corbacioglu, S., Socha, P., Uslu, N., Metin, A., Wahbeh, G. T., Husain, K., Ramadan, D., Al-Herz, W., Grimbacher, B., Sauer, M., Sykora, K. W., Kolezko, S., and C. Klein. 2012. Loss of interleukin-10 signaling and infantile inflammatory bowel disease implications for diagnosis and therapy. *Gastroenterology* 143:347-355.

Neven, B., Mamessier, E., Bruneau, J., Kaltenbach, S., Kotlarz, D., Suarez, F., Masliah-Planchon, J., Billot, K., Canioni, D., Frange, P., Redford-Weiss. I., Asnafi, V., Murugan, D., Bole, C., Nitschke, P., Goulet, O., Casanova, J. L., Blanche, S., Picard, C., Hermine, O., Rieux-Laucat, F., Brousse, N., Davi, F., Baud, V., Klein, C., Nadel, B., Ruemmele, F., and A. Fischer. 2013. A Mendelian predisposition to B-cell lymphoma caused by IL-10R deficiency. *Blood* 122:3713-3722.

Pigneur, B., Escher, J., Elawad, M., Lima, R., Buderus, S., Kierkus, J., Guariso, G., Canioni, D., Lambot, K., Talbotec, C., Shah, N., Begue, B., Rieux-Laucat, F., Goulet, O., Cerf-Bensussan, N., Neven. B., and F. M. Ruemmele. 2013. Phenotypic characterization of very early-onset IBD due to mutations in the IL10, IL10 receptor alpha or beta gene: A survey of the GENIUS working group. *Inflammatory bowel diseases* 19: 2820-2828.

Shouval, D. S., Biswas, A., Goettel, J. A., McCann, K., Conaway, E., Redhu, N. S., Mascanfroni, I. D., Al Adham, Z., Lavoie, S., Ibourk, M., Nguyen, D. D., Samsom, J. N., Escher, J. C., Somech, R., Weiss, B, Beier, R., Conklin, L. S., Ebens, C. L., Santos, F. G., Ferreira, A. R., Sherlock, M., Bhan, A. K., Müller, W., Mora, J. R., Quintana, F. J., Klein, C., Muise, A. M., Horwitz, B. H., and S. B. Snapper. 2014. Interleukin-10 receptor signaling in innate immune cells regulates mucosal immune tolerance and anti-inflammatory macrophage function. *Immunity* 40:706-719.

Shouval, D. S., Konnikova, L., Griffith, A. E., Wall, S. M., Biswas, A., Werner, L., Nunberg, M., Kammermeier, J., Goettel, J. A., Anand, R., Chen, H., Weiss, B., Li, J., Loizides, A., Yerushalmi, B., Yanagi, T., Beier, R., Conklin, L. S., Ebens, C. L., Santos, F. G. M. S., Sherlock, M., Goldsmith, J. D., Kotlarz, D., Glover, S. C., Shah, N., Bousvaros, A., Uhlig, H. H., Muise, A. M., Klein, C., and S. B. Snapper. 2017. Enhanced TH 17 Responses in Patients with IL10 Receptor Deficiency and Infantile-onset IBD. *Inflammatory bowel diseases* 23:1950-1961.

Yazdani, R., Moazzami, B., Madani, S. P., Behniafard, N., Azizi, G., Aflatoonian, M., Abolhassani, H., and A. Aghamohammadi. 2019. Candidiasis associated with very early onset inflammatory bowel disease: First IL10R B deficient case from the National Iranian Registry and review of the literature. *Clinical immunology* 205:35-42.

TABLE 10

Homozygous Mutations Present on Patient 2

| Chr | Pos | Ref | Alt | Function | Gene | AAChange | Sift_ Pred | Polyphen 2HVAR_ Pred | CADD_ Phred | MSC | GDI | Known PID? |
|---|---|---|---|---|---|---|---|---|---|---|---|---|
| 21 | 34649025 | T | G | missense | IL10RB | p.Trp100Gly | D, D | D, D, D, D | 29.8 | 23.8 | 10.34 | Yes |
| 2 | 208725979 | T | C | missense | PLEKHM3 | p.Glu653Gly | D, D | P | 29.7 | 2.31 | 3.26 | No |
| 16 | 88926306 | C | G | missense | TRAPPC2L | p.Phe100Leu | D | P, P | 25.9 | 23.84 | 5.19 | No |
| 6 | 41303876 | C | T | missense | NCR2 | p.Thr35Met | D, D, D | D, D, D | 23.3 | 2.31 | 1.78 | No |
| 20 | 47269910 | C | T | missense | PREX1 | p.Glu779Lys | T, T | B, B | 20.9 | 2.31 | 13.43 | No |
| 7 | 15725797 | ATGG | A | indel-inframe | MEOX2 | p.His77del | | | 20.5 | 4.78 | 5.44 | No |
| 4 | 8307852 | G | T | missense | HIRA3 | p.Val451Leu | T | B | 15.35 | 2.31 | 2.85 | No |
| 2 | 238737852 | T | A | splicing | RBM44 | | | | 10.96 | 2.31 | 4.67 | No |
| 2 | 238737860 | A | G | splicing | RBM44 | p.Arg868Arg | | | 10.79 | 2.31 | 4.67 | No |
| 13 | 38320594 | TA | T | splicing | TRPC4 | | | | 9.94 | 2.31 | 1.08 | No |
| 2 | 238737854 | T | G | splicing | RBM44 | | | | 8.267 | 2.31 | 4.67 | No |
| 16 | 12009530 | C | CCCG | indel-inframe | GSPT1 | p.Gly16dup | | | 7.76 | 2.31 | 10.44 | No |
| 7 | 131241029 | G | GGGCGAC | indel-inframe | PODXL | p.Ser29_Pro30dup | | | 5.726 | 2.31 | 3.35 | No |
| 20 | 32664864 | C | CCAG | indel-inframe | RALY | p.Ala230_Gly231insSer | | | 4.967 | 2.31 | 5.17 | No |
| 19 | 49657889 | T | TTCC | indel-inframe | HRC | p.Glu202dup | | | 4.004 | 2.31 | 10.86 | No |
| 13 | 25355965 | GT | G | splicing | RNF17 | | | | 3.637 | 2.31 | 9.75 | No |
| 3 | 158537415 | CTTTTT | C | splicing | MFSD1 | | | | 2.493 | 2.31 | 5.61 | No |
| 17 | 78081526 | A | AGCAGCGG | splicing | GAA | | | | 0.341 | 0.01 | 7.92 | No |

While there have been described what are presently believed to be the preferred embodiments of the present invention, those skilled in the art will realize that other and further changes and modifications may be made thereto without departing from the spirit of the invention, and it is intended to claim all such modifications and changes as come within the true scope of the invention.

The invention claimed is:

1. A method of treating or preventing fulminant viral hepatitis in a patient comprising administering an interleukin-18 (IL-18) antagonist comprising interleukin-18 binding protein (IL-18BP) to a patient in need thereof, wherein the patient comprises cells having a IL-18BP gene or protein variant wherein IL-18 binding of IL-18BP is absent or altered.

2. The method according to claim 1, wherein the IL-18BP gene or protein variant results in loss of function of IL-18BP.

3. The method according to claim 1, wherein the IL-18BP gene variant comprises at least one of: deletion of 10-25 nucleotides from the fourth and last intron, and deletion of 10-30 contiguous nucleotides from the fifth and last exon.

4. The method according to claim 3, wherein the IL-18BP gene variant comprises deletion of 19 nucleotides from the 4th and last intron, and deletion of 21 contiguous nucleotides from the 5th and last exon.

5. The method according to claim 1, wherein the patient comprises the following IL-18BP gene variant: NG_029021.1:g.7854_7893del; NM_173042.2:c.508-19_528del.

6. The method according to claim 1, wherein the patient is homozygous for the gene or protein variant.

7. The method according to claim 1, wherein the patient cells comprising the variant have at least 25%, 50%, or 75% more IL-18 as compared to cells from a person who is not suffering from fulminant viral hepatitis.

8. The method according to claim 1, wherein the patient cells comprising the variant have 10%-25%, 40%-60%, or 50-100% less IL-18BP or lower IL18BP mRNA levels as compared to cells from a person who is not suffering from fulminant viral hepatitis.

9. The method according to claim 1, wherein the cells are in the liver.

10. The method according to claim 1, wherein the patient is under the age of 30, 25, 20, 15, 10, or 5 years or is between the age of 5 and 25, 1 and 10, 10 and 20, or 10 and 15.

11. The method according to claim 1, wherein the patient has a primary infection comprising a liver-tropic virus.

12. The method according to claim 1, wherein the patient has a primary infection selected from the group consisting of: hepatitis A virus (HAV), hepatitis B virus (HBV), hepatitis C virus (HCV), and hepatitis E virus (HEV).

13. The method according to claim 1, further comprising administration of one or more antiviral therapies to the patient, wherein the antiviral therapies are selected from entecavir, tenofovir, lamivudine, adefovir, telbivudine, sofosbuvir, voxilapresvir, and pibrentasvir.

14. A method for evaluating and treating a patient with a liver tropic virus infection so as to alleviate, treat or prevent fulminant viral hepatitis comprising assessing the gene encoding interleukin-18 binding protein (IL-18BP) in the patient, or assessing the IL-18BP protein in the patient to determine whether IL-18BP is mutated to prevent IL-18 binding or result in loss of function of IL-18BP, the method further comprising administering to the patient an interleukin-18 (IL-18) antagonist comprising interleukin-18 binding protein (IL-18BP), whereby fulminant viral hepatitis is alleviated, treated or prevented in the patient.

* * * * *

SEQUENCE LISTING

```
<160> NUMBER OF SEQ ID NOS: 52

<210> SEQ ID NO 1
<211> LENGTH: 194
<212> TYPE: PRT
<213> ORGANISM: Homo sapiens

<400> SEQUENCE: 1

Met Thr Met Arg His Asn Trp Thr Pro Asp Leu Ser Pro Leu Trp Val
1               5                   10                  15

Leu Leu Leu Cys Ala His Val Val Thr Leu Leu Val Arg Ala Thr Pro
            20                  25                  30

Val Ser Gln Thr Thr Thr Ala Ala Thr Ala Ser Val Arg Ser Thr Lys
        35                  40                  45

Asp Pro Cys Pro Ser Gln Pro Pro Val Phe Pro Ala Ala Lys Gln Cys
    50                  55                  60

Pro Ala Leu Glu Val Thr Trp Pro Glu Val Glu Val Pro Leu Asn Gly
65                  70                  75                  80

Thr Leu Ser Leu Ser Cys Val Ala Cys Ser Arg Phe Pro Asn Phe Ser
                85                  90                  95

Ile Leu Tyr Trp Leu Gly Asn Gly Ser Phe Ile Glu His Leu Pro Gly
            100                 105                 110

Arg Leu Trp Glu Gly Ser Thr Ser Arg Glu Arg Gly Ser Thr Gly Thr
        115                 120                 125
```

```
Gln Leu Cys Lys Ala Leu Val Leu Glu Gln Leu Thr Pro Ala Leu His
    130                 135                 140

Ser Thr Asn Phe Ser Cys Val Leu Val Asp Pro Glu Gln Val Val Gln
145                 150                 155                 160

Arg His Val Val Leu Ala Gln Leu Trp Ala Gly Leu Arg Ala Thr Leu
                165                 170                 175

Pro Pro Thr Gln Glu Ala Leu Pro Ser Ser His Ser Ser Pro Gln Gln
            180                 185                 190

Gln Gly


<210> SEQ ID NO 2
<211> LENGTH: 325
<212> TYPE: PRT
<213> ORGANISM: Homo sapiens

<400> SEQUENCE: 2

Met Ala Trp Ser Leu Gly Ser Trp Leu Gly Gly Cys Leu Leu Val Ser
1               5                   10                  15

Ala Leu Gly Met Val Pro Pro Pro Glu Asn Val Arg Met Asn Ser Val
            20                  25                  30

Asn Phe Lys Asn Ile Leu Gln Trp Glu Ser Pro Ala Phe Ala Lys Gly
        35                  40                  45

Asn Leu Thr Phe Thr Ala Gln Tyr Leu Ser Tyr Arg Ile Phe Gln Asp
    50                  55                  60

Lys Cys Met Asn Thr Thr Leu Thr Glu Cys Asp Phe Ser Ser Leu Ser
65                  70                  75                  80

Lys Tyr Gly Asp His Thr Leu Arg Val Arg Ala Glu Phe Ala Asp Glu
                85                  90                  95

His Ser Asp Trp Val Asn Ile Thr Phe Cys Pro Val Asp Asp Thr Ile
            100                 105                 110

Ile Gly Pro Pro Gly Met Gln Val Glu Val Leu Ala Asp Ser Leu His
        115                 120                 125

Met Arg Phe Leu Ala Pro Lys Ile Glu Asn Glu Tyr Glu Thr Trp Thr
    130                 135                 140

Met Lys Asn Val Tyr Asn Ser Trp Thr Tyr Asn Val Gln Tyr Trp Lys
145                 150                 155                 160

Asn Gly Thr Asp Glu Lys Phe Gln Ile Thr Pro Gln Tyr Asp Phe Glu
                165                 170                 175

Val Leu Arg Asn Leu Glu Pro Trp Thr Thr Tyr Cys Val Gln Val Arg
            180                 185                 190

Gly Phe Leu Pro Asp Arg Asn Lys Ala Gly Glu Trp Ser Glu Pro Val
        195                 200                 205

Cys Glu Gln Thr Thr His Asp Glu Thr Val Pro Ser Trp Met Val Ala
    210                 215                 220

Val Ile Leu Met Ala Ser Val Phe Met Val Cys Leu Ala Leu Leu Gly
225                 230                 235                 240

Cys Phe Ala Leu Leu Trp Cys Val Tyr Lys Lys Thr Lys Tyr Ala Phe
                245                 250                 255

Ser Pro Arg Asn Ser Leu Pro Gln His Leu Lys Glu Phe Leu Gly His
            260                 265                 270

Pro His His Asn Thr Leu Leu Phe Phe Ser Phe Pro Leu Ser Asp Glu
        275                 280                 285

Asn Asp Val Phe Asp Lys Leu Ser Val Ile Ala Glu Asp Ser Glu Ser
    290                 295                 300
```

```
Gly Lys Gln Asn Pro Gly Asp Ser Cys Ser Leu Gly Thr Pro Pro Gly
305                 310                 315                 320

Gln Gly Pro Gln Ser
                325


<210> SEQ ID NO 3
<211> LENGTH: 19
<212> TYPE: DNA
<213> ORGANISM: Artificial Sequence
<220> FEATURE:
<223> OTHER INFORMATION: primer Seq-1 Fwd

<400> SEQUENCE: 3

cagcctgtga actaatgcc                                                19


<210> SEQ ID NO 4
<211> LENGTH: 20
<212> TYPE: DNA
<213> ORGANISM: Artificial Sequence
<220> FEATURE:
<223> OTHER INFORMATION: primer Seq-1 Rev

<400> SEQUENCE: 4

gaatttggtg agagaaggga                                               20


<210> SEQ ID NO 5
<211> LENGTH: 17
<212> TYPE: DNA
<213> ORGANISM: Artificial Sequence
<220> FEATURE:
<223> OTHER INFORMATION: primer Seq-2 Fwd

<400> SEQUENCE: 5

caaggagagg cctccag                                                  17


<210> SEQ ID NO 6
<211> LENGTH: 19
<212> TYPE: DNA
<213> ORGANISM: Artificial Sequence
<220> FEATURE:
<223> OTHER INFORMATION: primer Seq-2 Rev

<400> SEQUENCE: 6

actccaggta gacaggtag                                                19


<210> SEQ ID NO 7
<211> LENGTH: 20
<212> TYPE: DNA
<213> ORGANISM: Artificial Sequence
<220> FEATURE:
<223> OTHER INFORMATION: primer IL18BP SYBR Fwd*

<400> SEQUENCE: 7

cagctctggg ctgggctgag                                               20


<210> SEQ ID NO 8
<211> LENGTH: 20
<212> TYPE: DNA
<213> ORGANISM: Artificial Sequence
<220> FEATURE:
<223> OTHER INFORMATION: primer IL18BP SYBR Rev

<400> SEQUENCE: 8

ggggtgtgtt gcgcatccac                                               20
```

<210> SEQ ID NO 9
<211> LENGTH: 20
<212> TYPE: DNA
<213> ORGANISM: Artificial Sequence
<220> FEATURE:
<223> OTHER INFORMATION: primer M1 SYBR Fwd

<400> SEQUENCE: 9
ggaacgtggg agcacaggta 20

<210> SEQ ID NO 10
<211> LENGTH: 20
<212> TYPE: DNA
<213> ORGANISM: Artificial Sequence
<220> FEATURE:
<223> OTHER INFORMATION: primer M1 SYBR Rev

<400> SEQUENCE: 10
ttgagcgttc ccctgccaga 20

<210> SEQ ID NO 11
<211> LENGTH: 20
<212> TYPE: DNA
<213> ORGANISM: Artificial Sequence
<220> FEATURE:
<223> OTHER INFORMATION: primer M2 SYBR Fwd

<400> SEQUENCE: 11
ggaacgtggg agcacaggta 20

<210> SEQ ID NO 12
<211> LENGTH: 20
<212> TYPE: DNA
<213> ORGANISM: Artificial Sequence
<220> FEATURE:
<223> OTHER INFORMATION: primer M2 SYBR Rev

<400> SEQUENCE: 12
cttgagcgtt cccccagagc 20

<210> SEQ ID NO 13
<211> LENGTH: 21
<212> TYPE: DNA
<213> ORGANISM: Artificial Sequence
<220> FEATURE:
<223> OTHER INFORMATION: primer M3 SYBR Fwd

<400> SEQUENCE: 13
cctgcacagc accaacttct c 21

<210> SEQ ID NO 14
<211> LENGTH: 21
<212> TYPE: DNA
<213> ORGANISM: Artificial Sequence
<220> FEATURE:
<223> OTHER INFORMATION: primer M3 SYBR Rev

<400> SEQUENCE: 14
gagacatggg agtgggagcc a 21

<210> SEQ ID NO 15
<211> LENGTH: 21
<212> TYPE: DNA
<213> ORGANISM: Artificial Sequence
<220> FEATURE:
<223> OTHER INFORMATION: primer GAPDH SYBR Fwd

<400> SEQUENCE: 15
ggagcgagat ccctccaaaa t 21

<210> SEQ ID NO 16
<211> LENGTH: 23
<212> TYPE: DNA
<213> ORGANISM: Artificial Sequence
<220> FEATURE:
<223> OTHER INFORMATION: primer GAPDH SYBR Rev

<400> SEQUENCE: 16
ggctgttgtc atacttctca tgg 23

<210> SEQ ID NO 17
<211> LENGTH: 52
<212> TYPE: DNA
<213> ORGANISM: Artificial Sequence
<220> FEATURE:
<223> OTHER INFORMATION: primer AP-1

<400> SEQUENCE: 17
ccagtgagca gagtgacgag gactcgagct caagcttttt tttttttttt tt 52

<210> SEQ ID NO 18
<211> LENGTH: 18
<212> TYPE: DNA
<213> ORGANISM: Artificial Sequence
<220> FEATURE:
<223> OTHER INFORMATION: primer UAP-1

<400> SEQUENCE: 18
ccagtgagca gagtgacg 18

<210> SEQ ID NO 19
<211> LENGTH: 18
<212> TYPE: DNA
<213> ORGANISM: Artificial Sequence
<220> FEATURE:
<223> OTHER INFORMATION: primer AUAP

<400> SEQUENCE: 19
gaggactcga gctcaagc 18

<210> SEQ ID NO 20
<211> LENGTH: 22
<212> TYPE: DNA
<213> ORGANISM: Artificial Sequence
<220> FEATURE:
<223> OTHER INFORMATION: primer FEx1

<400> SEQUENCE: 20
atgaccatga gacacaactg ga 22

<210> SEQ ID NO 21
<211> LENGTH: 20
<212> TYPE: DNA
<213> ORGANISM: Artificial Sequence
<220> FEATURE:
<223> OTHER INFORMATION: primer FEx1-2

<400> SEQUENCE: 21
ctggacacca gacctcagcc 20

<210> SEQ ID NO 22
<211> LENGTH: 20

<212> TYPE: DNA
<213> ORGANISM: Artificial Sequence
<220> FEATURE:
<223> OTHER INFORMATION: primer FEx2-3

<400> SEQUENCE: 22
ccactgaatg gaacgctgag 20

<210> SEQ ID NO 23
<211> LENGTH: 19
<212> TYPE: DNA
<213> ORGANISM: Artificial Sequence
<220> FEATURE:
<223> OTHER INFORMATION: primer RIL18BPa

<400> SEQUENCE: 23
ttaaccctgc tgctgtgga 19

<210> SEQ ID NO 24
<211> LENGTH: 19
<212> TYPE: DNA
<213> ORGANISM: Artificial Sequence
<220> FEATURE:
<223> OTHER INFORMATION: primer RIL18BPbd

<400> SEQUENCE: 24
tcaaggttgt gctgctgct 19

<210> SEQ ID NO 25
<211> LENGTH: 18
<212> TYPE: DNA
<213> ORGANISM: Artificial Sequence
<220> FEATURE:
<223> OTHER INFORMATION: primer RIL18BPc

<400> SEQUENCE: 25
tcacaggctg ctctggca 18

<210> SEQ ID NO 26
<211> LENGTH: 28
<212> TYPE: DNA
<213> ORGANISM: Artificial Sequence
<220> FEATURE:
<223> OTHER INFORMATION: primer pTAG4-IL18BP Fwd

<400> SEQUENCE: 26
ctggaattcc ttctgcggcc ttctcatg 28

<210> SEQ ID NO 27
<211> LENGTH: 30
<212> TYPE: DNA
<213> ORGANISM: Artificial Sequence
<220> FEATURE:
<223> OTHER INFORMATION: primer pTAG4-IL18BP Rev

<400> SEQUENCE: 27
gcactcgagg atggatcttt tctaaatgtt 30

<210> SEQ ID NO 28
<211> LENGTH: 40
<212> TYPE: DNA
<213> ORGANISM: Artificial Sequence
<220> FEATURE:
<223> OTHER INFORMATION: primer AP-2

<400> SEQUENCE: 28

-continued gcggaattcg gatccctcga gttttttttt ttttttttt 40

<210> SEQ ID NO 29
<211> LENGTH: 23
<212> TYPE: DNA
<213> ORGANISM: Artificial Sequence
<220> FEATURE:
<223> OTHER INFORMATION: primer UAP2

<400> SEQUENCE: 29
gcggaattcg gatccctcga gtt 23

<210> SEQ ID NO 30
<211> LENGTH: 20
<212> TYPE: DNA
<213> ORGANISM: Artificial Sequence
<220> FEATURE:
<223> OTHER INFORMATION: primer FAD1-2

<400> SEQUENCE: 30
agggccagct gttgggctcg 20

<210> SEQ ID NO 31
<211> LENGTH: 22
<212> TYPE: DNA
<213> ORGANISM: Artificial Sequence
<220> FEATURE:
<223> OTHER INFORMATION: primer FAD2-Ex4

<400> SEQUENCE: 31
cgtcggcctc cgaacgccgg ga 22

<210> SEQ ID NO 32
<211> LENGTH: 28
<212> TYPE: DNA
<213> ORGANISM: Artificial Sequence
<220> FEATURE:
<223> OTHER INFORMATION: primer RUTR

<400> SEQUENCE: 32
ctccattgaa taatccttta tgaggacc 28

<210> SEQ ID NO 33
<211> LENGTH: 24
<212> TYPE: DNA
<213> ORGANISM: Artificial Sequence
<220> FEATURE:
<223> OTHER INFORMATION: primer HPRT1 Fwd

<400> SEQUENCE: 33
ctggcgtcgt gattagtgat gatg 24

<210> SEQ ID NO 34
<211> LENGTH: 24
<212> TYPE: DNA
<213> ORGANISM: Artificial Sequence
<220> FEATURE:
<223> OTHER INFORMATION: primer HPRT1 Rev

<400> SEQUENCE: 34
ttgagcacac agagggctac aatg 24

<210> SEQ ID NO 35
<211> LENGTH: 36
<212> TYPE: DNA
<213> ORGANISM: Artificial Sequence
<220> FEATURE:
<223> OTHER INFORMATION: primer IL18BP BamHI (Kozak)

<400> SEQUENCE: 35
gttggatccg ccaccatgag acacaactgg acacca 36

<210> SEQ ID NO 36
<211> LENGTH: 50
<212> TYPE: DNA
<213> ORGANISM: Artificial Sequence
<220> FEATURE:
<223> OTHER INFORMATION: primer IL18BP-His XbaI

<400> SEQUENCE: 36
atatctagat taatgatgat gatgatgatg accctgctgc tgtggactgc 50

<210> SEQ ID NO 37
<211> LENGTH: 33
<212> TYPE: DNA
<213> ORGANISM: Artificial Sequence
<220> FEATURE:
<223> OTHER INFORMATION: primer V23I SDM Fwd

<400> SEQUENCE: 37
ctcctgtgtg cccacatcgt cactctcctg gtc 33

<210> SEQ ID NO 38
<211> LENGTH: 33
<212> TYPE: DNA
<213> ORGANISM: Artificial Sequence
<220> FEATURE:
<223> OTHER INFORMATION: primer V23I SDM Rev

<400> SEQUENCE: 38
gaccaggaga gtgacgatgt gggcacacag gag 33

<210> SEQ ID NO 39
<211> LENGTH: 31
<212> TYPE: DNA
<213> ORGANISM: Artificial Sequence
<220> FEATURE:
<223> OTHER INFORMATION: primer R121Q SDM Fwd

<400> SEQUENCE: 39
aggggagcac cagccaggaa cgtgggagca c 31

<210> SEQ ID NO 40
<211> LENGTH: 31
<212> TYPE: DNA
<213> ORGANISM: Artificial Sequence
<220> FEATURE:
<223> OTHER INFORMATION: primer R121Q SDM Rev

<400> SEQUENCE: 40
gtgctcccac gttcctggct ggtgctcccc t 31

<210> SEQ ID NO 41
<211> LENGTH: 30
<212> TYPE: DNA
<213> ORGANISM: Artificial Sequence
<220> FEATURE:
<223> OTHER INFORMATION: primer P184L SDM Fwd

<400> SEQUENCE: 41
cacccaagaa gccctgctct ccagccacag 30

<210> SEQ ID NO 42
<211> LENGTH: 30
<212> TYPE: DNA
<213> ORGANISM: Artificial Sequence
<220> FEATURE:
<223> OTHER INFORMATION: primer P184L SDM Rev

<400> SEQUENCE: 42
ctgtggctgg agagcagggc ttcttgggtg 30

<210> SEQ ID NO 43
<211> LENGTH: 50
<212> TYPE: DNA
<213> ORGANISM: Artificial Sequence
<220> FEATURE:
<223> OTHER INFORMATION: primer Q192H-His XbaI

<400> SEQUENCE: 43
atatctagat taatgatgat gatgatgatg accctgatgc tgtggactgc 50

<210> SEQ ID NO 44
<211> LENGTH: 68
<212> TYPE: DNA
<213> ORGANISM: Artificial Sequence
<220> FEATURE:
<223> OTHER INFORMATION: primer M1-His XbaI

<400> SEQUENCE: 44
atatctagat taatgatgat gatgatgatg ggatgttttt tttttttttt tttctccatt 60
gaataatc 68

<210> SEQ ID NO 45
<211> LENGTH: 68
<212> TYPE: DNA
<213> ORGANISM: Artificial Sequence
<220> FEATURE:
<223> OTHER INFORMATION: primer M2-His XbaI

<400> SEQUENCE: 45
atatctagat taatgatgat gatgatgatg ggatgttttt tttttttttt tttctccatt 60
gaataatc 68

<210> SEQ ID NO 46
<211> LENGTH: 49
<212> TYPE: DNA
<213> ORGANISM: Artificial Sequence
<220> FEATURE:
<223> OTHER INFORMATION: primer M3-His XbaI

<400> SEQUENCE: 46
atatctagat taatgatgat gatgatgatg ctgaagaggc agcatttca 49

<210> SEQ ID NO 47
<211> LENGTH: 30
<212> TYPE: DNA
<213> ORGANISM: Artificial Sequence
<220> FEATURE:
<223> OTHER INFORMATION: primer M1 SDM Fwd

<400> SEQUENCE: 47
ccagctctgg caggggaacg ctcaagcctg 30

<210> SEQ ID NO 48
<211> LENGTH: 30

-continued

```
<212> TYPE: DNA
<213> ORGANISM: Artificial Sequence
<220> FEATURE:
<223> OTHER INFORMATION: primer M1 SDM Rev

<400> SEQUENCE: 48

cgttcccctg ccagagctgg gccaggacga                                        30


<210> SEQ ID NO 49
<211> LENGTH: 30
<212> TYPE: DNA
<213> ORGANISM: Artificial Sequence
<220> FEATURE:
<223> OTHER INFORMATION: primer M2 SDM Fwd

<400> SEQUENCE: 49

ccagctctgg gggaacgctc aagcctggtt                                        30


<210> SEQ ID NO 50
<211> LENGTH: 30
<212> TYPE: DNA
<213> ORGANISM: Artificial Sequence
<220> FEATURE:
<223> OTHER INFORMATION: primer M2 SDM Rev

<400> SEQUENCE: 50

gagcgttccc ccagagctgg gccaggacga                                        30


<210> SEQ ID NO 51
<211> LENGTH: 30
<212> TYPE: DNA
<213> ORGANISM: Artificial Sequence
<220> FEATURE:
<223> OTHER INFORMATION: primer M3 SDM Fwd

<400> SEQUENCE: 51

ccagctctgg ctcccactcc catgtctctg                                        30


<210> SEQ ID NO 52
<211> LENGTH: 30
<212> TYPE: DNA
<213> ORGANISM: Artificial Sequence
<220> FEATURE:
<223> OTHER INFORMATION: primer M3 SDM Rev

<400> SEQUENCE: 52

ggagtgggag ccagagctgg gccaggacga                                        30
```